US010463716B2

(12) United States Patent
Gong et al.

(10) Patent No.: US 10,463,716 B2
(45) Date of Patent: Nov. 5, 2019

(54) METHODS FOR TREATING CARDIOVASCULAR DYSFUNCTION AND IMPROVING FLUID HOMEOSTASIS WITH ELABELA PEPTIDE HORMONE

(71) Applicant: UNIVERSITY OF MARYLAND, BALTIMORE, Baltimore, MD (US)

(72) Inventors: Da-Wei Gong, Olney, MD (US); Daozhan Yu, Ellicott City, MD (US); Rongze Yang, Ellicott City, MD (US); Alan Shuldiner, Baltimore, MD (US); Ling Chen, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/519,021

(22) PCT Filed: Oct. 13, 2015

(86) PCT No.: PCT/US2015/055389
§ 371 (c)(1),
(2) Date: Apr. 13, 2017

(87) PCT Pub. No.: WO2016/061141
PCT Pub. Date: Apr. 21, 2016

(65) Prior Publication Data
US 2017/0224779 A1 Aug. 10, 2017

Related U.S. Application Data

(60) Provisional application No. 62/063,005, filed on Oct. 13, 2014.

(51) Int. Cl.
| | |
|---|---|
| *A61P 9/02* | (2006.01) |
| *A61P 9/04* | (2006.01) |
| *A61K 38/16* | (2006.01) |
| *C07K 14/47* | (2006.01) |
| *A61K 38/22* | (2006.01) |
| *A61K 45/06* | (2006.01) |
| *G01N 33/50* | (2006.01) |
| *C07K 14/575* | (2006.01) |
| *G01N 33/68* | (2006.01) |
| *A61P 9/10* | (2006.01) |
| *A61P 9/06* | (2006.01) |
| *A61P 9/00* | (2006.01) |
| *A61P 9/12* | (2006.01) |
| *C07K 19/00* | (2006.01) |
| *A61K 38/00* | (2006.01) |

(52) U.S. Cl.
CPC .............. *A61K 38/22* (2013.01); *A61K 38/16* (2013.01); *A61K 45/06* (2013.01); *A61P 9/00* (2018.01); *A61P 9/02* (2018.01); *A61P 9/04* (2018.01); *A61P 9/06* (2018.01); *A61P 9/10* (2018.01); *A61P 9/12* (2018.01); *C07K 14/47* (2013.01); *C07K 14/4722* (2013.01); *C07K 14/575* (2013.01); *G01N 33/5044* (2013.01); *G01N 33/6893* (2013.01); *A61K 38/00* (2013.01); *C07K 14/4705* (2013.01); *C07K 19/00* (2013.01); *C07K 2319/02* (2013.01); *C07K 2319/30* (2013.01); *G01N 2800/32* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,902,761 B2 * | 2/2018 | Reversade | ............ G01N 33/74 |
| 2008/0182779 A1 | 7/2008 | Euan et al. | |
| 2014/0155315 A1 | 6/2014 | Zecri et al. | |
| 2014/0275489 A1 | 9/2014 | Stevis | |

FOREIGN PATENT DOCUMENTS

WO 2015/084264 A1 6/2015

OTHER PUBLICATIONS

Pauli et al, 2014. Science, 343:6172; 19 pages.*
Deedwania, 1997. Am J Hypertens. 10:280S-288S (Year: 1997).*
Beck et al, 2011. mAbs: 3(5): 415-416 (Year: 2011).*
"Choosing Medicines for High Blood Pressure: A Review of the Research on ACEIs, ARBs and DRIs", published by the Agency for Healthcare Research and Quality (AHRQ), Oct. 2011, AHRQ Pub. No. 11(12)-EHC063-A, no author listed, pp. 1-14 (Year: 2011).*
International Search Report and Written Opinion for correspondence EP Application 15851315.0 dated Apr. 5, 2018, pp. 1-22.
Koguchi, W., et al., Cardioprotective effect of apelin-13 on cardiac performance and remodeling in end-stage heart failure, "Circulation journal", pp. 137-144, vol. 76 (2012).
Wang, M., et al., Acute intravenous infusion of an adenosine regulating agent improves left ventricular function in dogs with advanced heart failure, "cardiovasc drugs ther", pp. 489-498, vol. 27 (2013).
Yang, P., et al., Elabela/Toddler is an endogenous agonist of the apelin APJ Receptor in the adult cardiovascular system and exogenous administration of the peptide compensates for the downregulation of its expression in pulmonary arterial Hypertension Clinical perspective, "Circulation (baltimore)", pp. 1160-1173, vol. 135, Issue 12 (2017).

(Continued)

*Primary Examiner* — Zachary C Howard
(74) *Attorney, Agent, or Firm* — Beusse Wolter Sanks & Maire; Eugene J. Molinelli; Martha Cassidy

(57) ABSTRACT

The present invention generally to methods of treating subjects suffering from a cardiac condition or having a risk factor for developing a cardiac condition by administering an ELA peptide or fusion protein to a subject in need. The invention relates to fusion proteins of Fc-ELA-32 and Fc-ELA-21 that exhibit improved properties for use as therapeutic agents, e.g. in the treatment of cardiac conditions. In addition, the present invention relates to polynucleotides encoding such fusion proteins, and vectors and host cells comprising such polynucleotides. The invention further relates to methods for producing the fusion proteins of the invention, and to methods of using them in the treatment of disease.

10 Claims, 23 Drawing Sheets
Specification includes a Sequence Listing.

(56) References Cited

OTHER PUBLICATIONS

Ashley, E.A., et al., "The endogenous peptide apelin potently improves cardiac contractility and reduces cardiac loading in vivo," Cardiovasc Res 2005, pp. 73-82, vol. No. 65.

Charles, C.J., "Update on apelin peptides as putative targets for cardiovascular drug discovery," Expert Opinion on Drug Discovery 2011, pp. 633-644, vol. 6, No. 6.

Charo, D.N., et al., "Endogenous regulation of cardiovascular function by apelin-APJ," Am J Physiol Heart Circ Physiol 2009, pp. H1904-H1913, vol. No. 297.

Chng, S.C., et al.,"ELABELA: a hormone essential for heart development signals via the apelin receptor," Dev Cell 2013, pp. 672-680, vol. No. 27.

Falcao-Pires, I., "The apelinergic system: a promising therapeutic target," Expert Opin. Ther. Targets 2010, pp. 1-13, vol. 14, No. 5.

Hamada, J., et al.,"Evaluation of novel cyclic analogues of apelin," J Mol Med 2008, pp. 547-552, vol. No. 22.

Jia, Y.X., et al., "Apelin protects myocardial injury induced by isoproterenol in rats," Regul Pepi 2006, pp. 147-154, vol. No. 133.

Kasai, A., et al., "Apelin is a novel angiogenic factor in retinal endothelial cells," Biochem Biophys Res Commun 2004, pp. 395-400, vol. No. 325.

Kleinz, M.J. and Baxter, G.F., "Apelin reduces myocardial reperfusion injury independently of PI3K/Akt and P70S6 kinase," Regul Pepi 2008, pp. 271-277, vol. No. 146.

Laflamme, B., "ELABELA, a peptide hormone for heart development," Nature Genetics 2014, p. 7, vol. 46, No. 1.

Lee, D.K., et a., "Modification of the terminal residue of apelin-13 antagonizes its hypotensive action," Endocrinology 2005, pp. 231-236, vol. No. 146.

Pisarenko, O.I., "Limitation of myocardial infarction by a structural analog of the peptide apclin-12," Doklady Biol Sci 2012, pp. 65-67, vol. 443, Publisher: Pleiades Publishing, Ltd.

Szokodi, I., et al., "Apelin, the novel endogenous ligand of the orphan receptor APJ, regulates cardiac contractility," Circ Res. 2002, pp. 434-440, vol. 91, No. 5.

Tatemoto, K., et al., "Isolation and characterization of a novel endogenous peptide ligand for the human APJ receptor," Biochem Biophys Res Comm 1998, pp. 471-476, vol. 251.

Tatemoto, K., et al., "The novel peptide apelin lowers blood pressure via a nitric oxide-dependent mechanism," Regulatory Peptides 1999, pp. 87-92, vol. 99.

Wang, W., et al., "Loss of Apelin exacerbates myocardial infarction adverse remodeling and ischemia-reperfusion injury: therapeutic potential of synthetic Apelin analogues," J Am Heart Assoc 2013, pp. 1-17, e000249. doi: 10.1161/JAHA.113.000249.

Xie, F., et al., "ELABELA: a novel hormone in cardiac development acting as a new endogenous ligand for the APJ receptor," Acta Biochim Biophys Sin 2014, pp. 620-622, vol. 46.

Yu, et al., "Apelin and its receptor APJ in cardiovascular diseases," Clinica Chimica Acta 2014, pp. 1-4, vol. 428.

Zeng, H., "Apelin gene therapy increases myocardial vascular density and ameliorates diabetic cardiomyopathy via upregulation of sirtuin 3," Am J Physiol Heart Circ Physiol 2014, pp. H585-H597, vol. 306.

Zhong, J.C., et al., "Apelin modulates aortic vascular tone via endothelial nitric oxide synthase phosphorylation pathway in diabetic mice," Cardiovasc Res 2007, pp. 388-395, vol. 74.

ISA/KR, International Search Report and Written Opinion, International Patent Application No. PCT/US2015/055389, dated Dec. 21, 2015, 11 pages.

European Extended Search Report for correspondence EP Application 15851315.0 dated Jul. 8, 2018, pp. 1-18.

Xie, et al., Elabela: a novel hormone in cardiac development acting as a new endogenous ligand for the APJ receptor, "Acta Biochim BioPhys Sin", vol. 46 Issue 7, pp. 620-622 (2014).

Laflamme, Elabela a peptide hormone for heart fevelopment, "Nature Genetics", vol. 46, p. 7 (2014).

Chng, et al., Ebela: a hormone essential for heart development signals via the apelin receptor, "Developmental Cell", vol. 27, Issue 6, pp. 672-680 (2013).

\* cited by examiner

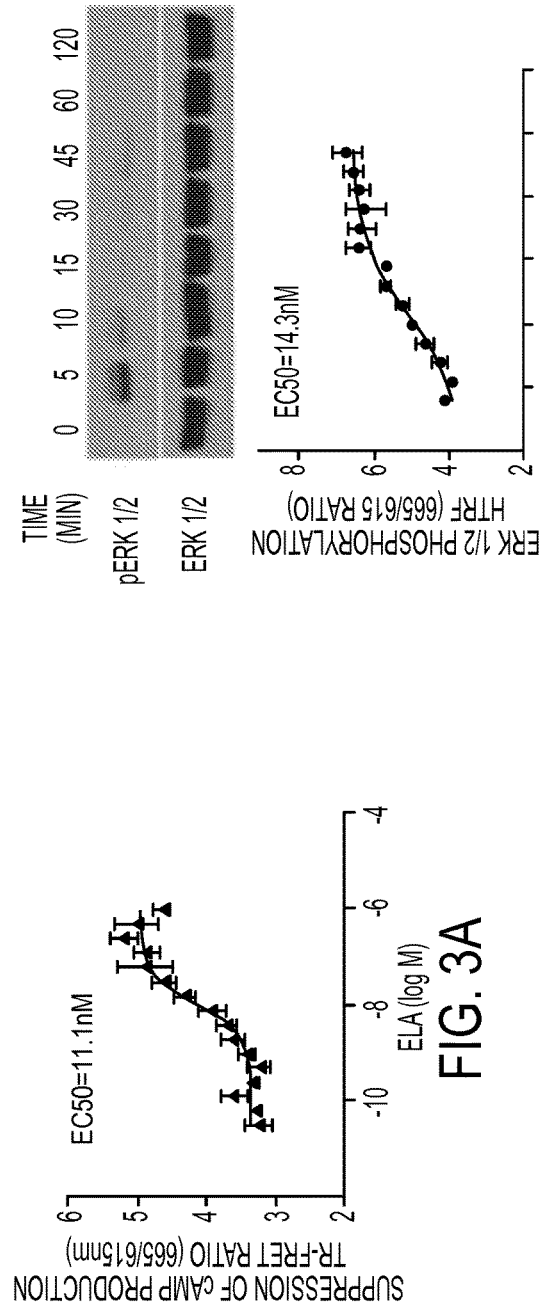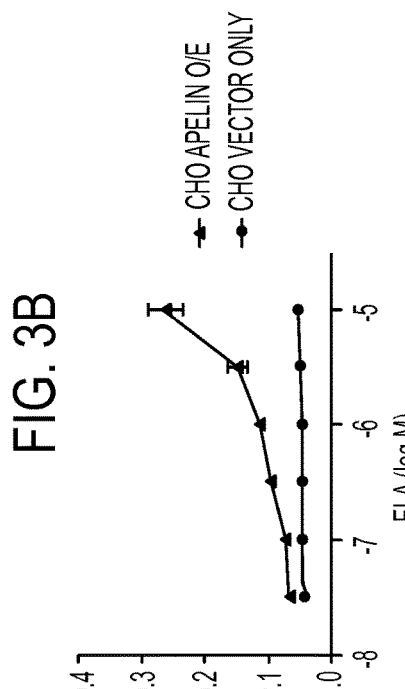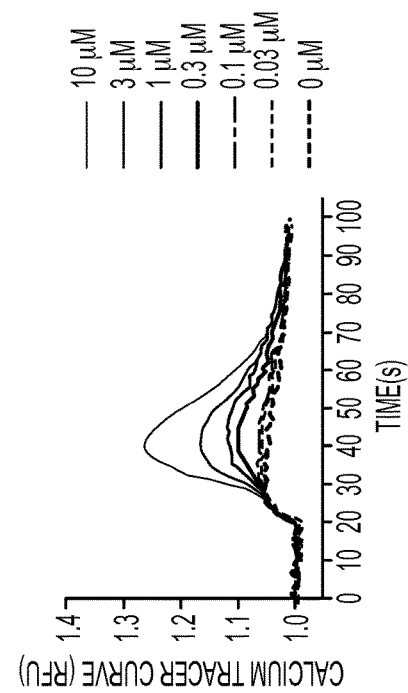

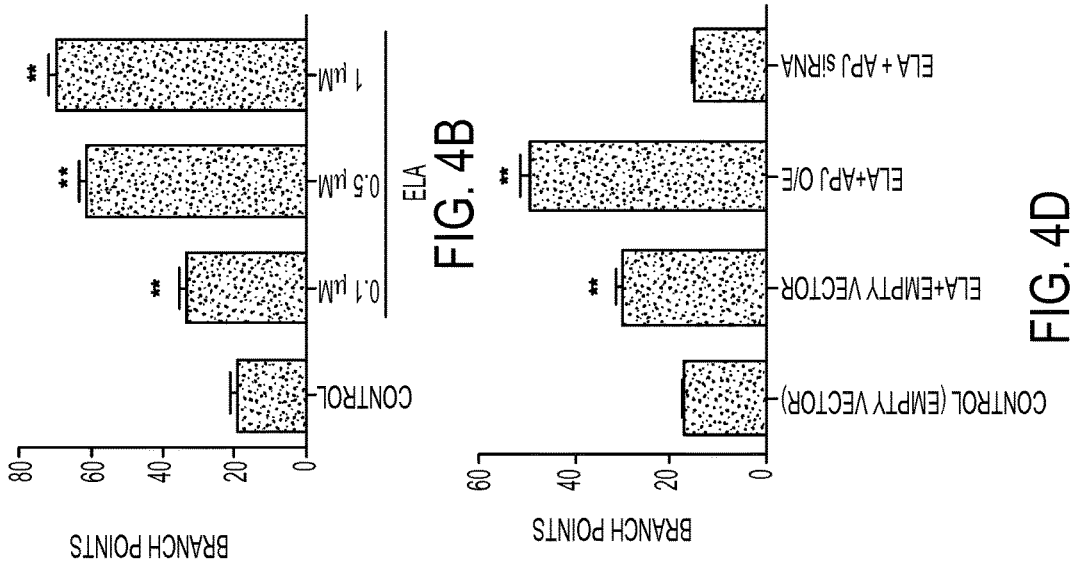
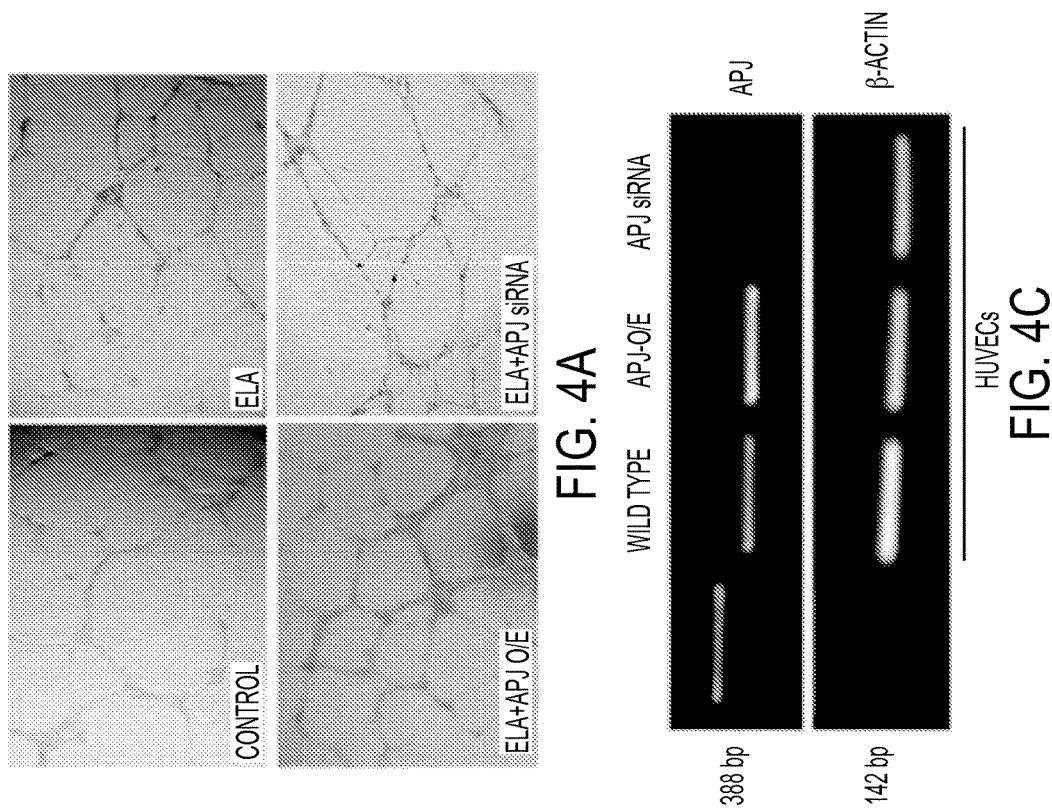

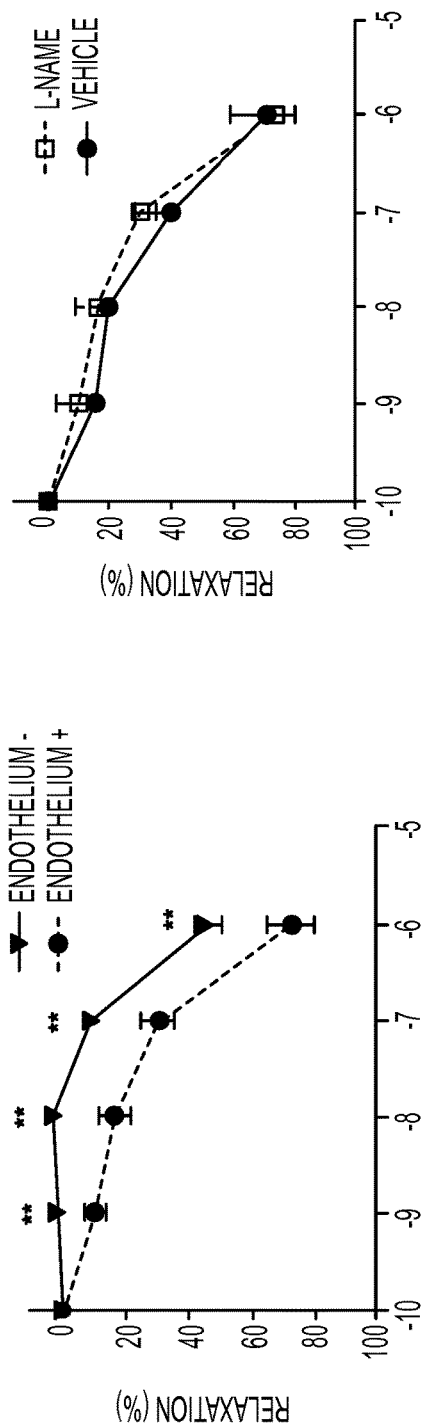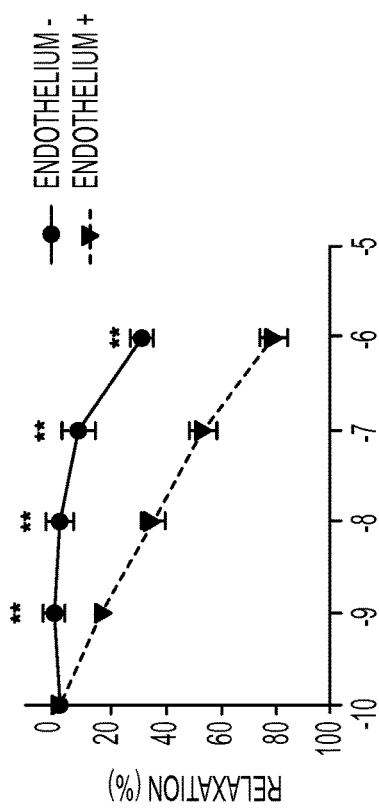
FIG. 5A
FIG. 5B
FIG. 5C

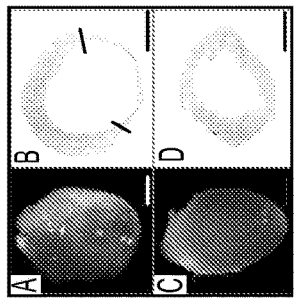
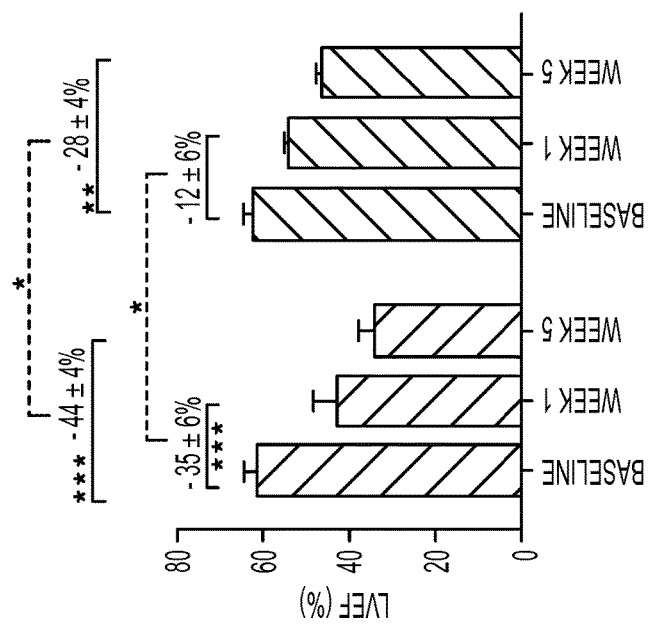
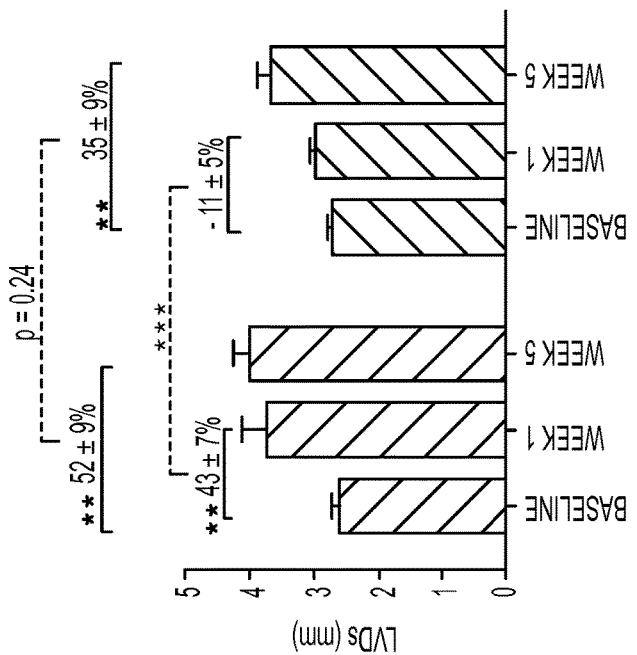
FIG. 7A
FIG. 7B
FIG. 7C

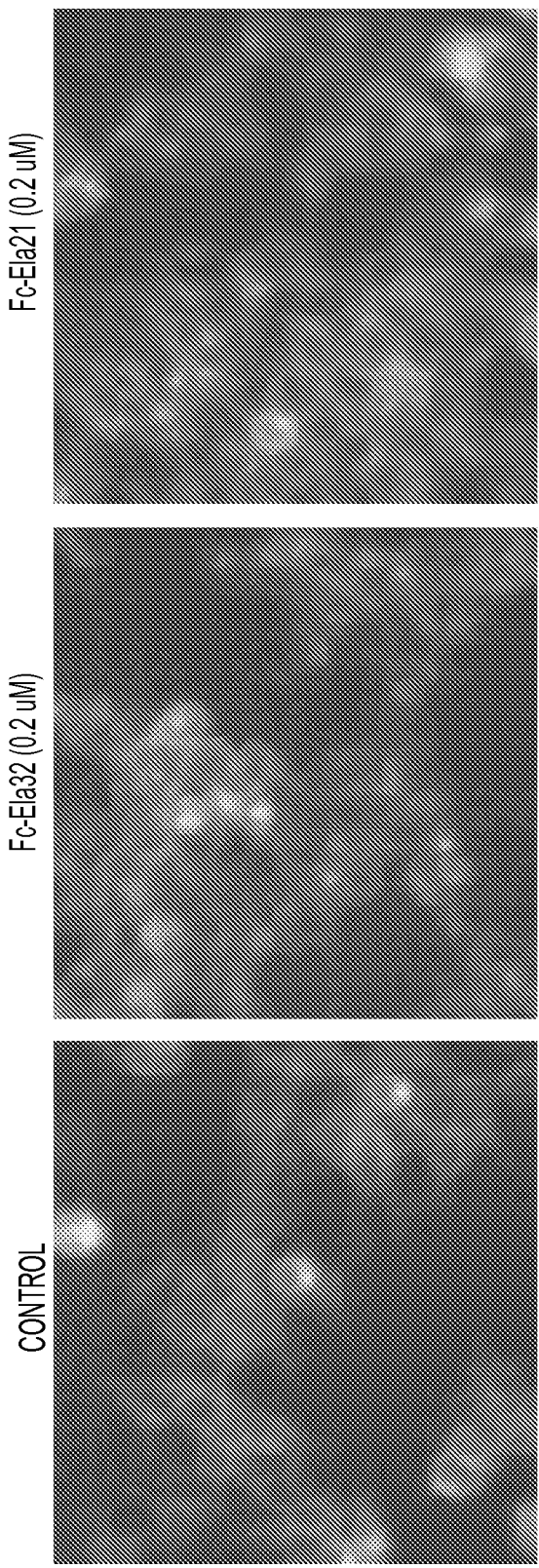

SEQUENCE LISTING

```
<160> NUMBER OF SEQ ID NOS: 16

<210> SEQ ID NO 1
<211> LENGTH: 32
<212> TYPE: PRT
<213> ORGANISM: Artificial Sequence
<220> FEATURE:
<223> OTHER INFORMATION: Synthetic: ELA-32

<400> SEQUENCE: 1

Gln Arg Pro Val Asn Leu Thr Met Arg Arg Lys Leu Arg Lys His Asn
1               5                   10                  15

Cys Leu Gln Arg Arg Cys Met Pro Leu His Ser Arg Val Pro Phe Pro
            20                  25                  30

<210> SEQ ID NO 2
<211> LENGTH: 21
<212> TYPE: PRT
<213> ORGANISM: Artificial Sequence
<220> FEATURE:
<223> OTHER INFORMATION: Synthetic: ELA-21

<400> SEQUENCE: 2

Leu Arg Lys His Asn Cys Leu Gln Arg Arg Cys Met Pro Leu His Ser
1               5                   10                  15

Arg Val Pro Phe Pro
            20

<210> SEQ ID NO 3
<211> LENGTH: 13
<212> TYPE: PRT
<213> ORGANISM: Artificial Sequence
<220> FEATURE:
```

-continued

<223> OTHER INFORMATION: Synthetic: Apelin-13

<400> SEQUENCE: 3

Gln Arg Pro Arg Leu Ser His Lys Gly Pro Met Pro Phe
1               5                   10

<210> SEQ ID NO 4
<211> LENGTH: 300
<212> TYPE: PRT
<213> ORGANISM: Artificial Sequence
<220> FEATURE:
<223> OTHER INFORMATION: Synthetic: Fc-ELA-32 or htPA-SS-Fc-ELA-32

<400> SEQUENCE: 4

Met Asp Ala Met Lys Arg Gly Leu Cys Cys Val Leu Leu Leu Cys Gly
1               5                   10                  15

Ala Val Phe Val Ser Pro Ser Gln Asp Ile Asp Lys Thr His Thr Cys
                20                  25                  30

Pro Pro Cys Pro Ala Pro Glu Leu Leu Gly Gly Pro Ser Val Phe Leu
            35                  40                  45

Phe Pro Pro Lys Pro Lys Asp Thr Leu Met Ile Ser Arg Thr Pro Glu
        50                  55                  60

Val Thr Cys Val Val Val Asp Val Ser His Glu Asp Pro Glu Val Lys
65                  70                  75                  80

Phe Asn Trp Tyr Val Asp Gly Val Glu Val His Asn Ala Lys Thr Lys
                85                  90                  95

Pro Arg Glu Glu Gln Tyr Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Ala Leu Pro Val Pro Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Arg Glu Glu Met Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Lys Gly Gly Gly
                245                 250                 255

Gly Ser Gly Gly Gly Gly Ser Gly Gly Gly Ser Gln Arg Pro Val
            260                 265                 270

Asn Leu Thr Met Arg Arg Lys Leu Arg Lys His Asn Cys Leu Gln Arg
        275                 280                 285

Arg Cys Met Pro Leu His Ser Arg Val Pro Phe Pro
    290                 295                 300

<210> SEQ ID NO 5
<211> LENGTH: 289
<212> TYPE: PRT
<213> ORGANISM: Artificial Sequence
<220> FEATURE:
<223> OTHER INFORMATION: Synthetic: Fc-ELA-21 or htPA-SS-Fc-ELA-21

<400> SEQUENCE: 5

```
Met Asp Ala Met Lys Arg Gly Leu Cys Cys Val Leu Leu Leu Cys Gly
1               5                   10                  15

Ala Val Phe Val Ser Pro Ser Gln Asp Ile Asp Lys Thr His Thr Cys
            20                  25                  30

Pro Pro Cys Pro Ala Pro Glu Leu Leu Gly Gly Pro Ser Val Phe Leu
        35                  40                  45

Phe Pro Pro Lys Pro Lys Asp Thr Leu Met Ile Ser Arg Thr Pro Glu
    50                  55                  60

Val Thr Cys Val Val Val Asp Val Ser His Glu Asp Pro Glu Val Lys
65                  70                  75                  80

Phe Asn Trp Tyr Val Asp Gly Val Glu Val His Asn Ala Lys Thr Lys
                85                  90                  95

Pro Arg Glu Glu Gln Tyr Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Ala Leu Pro Val Pro Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Arg Glu Glu Met Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Lys Gly Gly Gly
                245                 250                 255

Gly Ser Gly Gly Gly Ser Gly Gly Gly Ser Leu Arg Lys His
            260                 265                 270

Asn Cys Leu Gln Arg Arg Cys Met Pro Leu His Ser Arg Val Pro Phe
        275                 280                 285

Pro
```

<210> SEQ ID NO 6
<211> LENGTH: 6
<212> TYPE: PRT
<213> ORGANISM: Artificial Sequence
<220> FEATURE:
<223> OTHER INFORMATION: Synthetic: linker

<400> SEQUENCE: 6

```
Ser Gly Gly Gly Gly Ser
1               5
```

<210> SEQ ID NO 7
<211> LENGTH: 21
<212> TYPE: DNA
<213> ORGANISM: Artificial Sequence

```
<220> FEATURE:
<223> OTHER INFORMATION: Synthetic: APJ 5 forward primer
<220> FEATURE:
<221> NAME/KEY: misc_feature
<222> LOCATION: (14)..(14)
<223> OTHER INFORMATION: n is inosine

<400> SEQUENCE: 7
ctggtggtga cctntgccct g                                          21

<210> SEQ ID NO 8
<211> LENGTH: 44
<212> TYPE: DNA
<213> ORGANISM: Artificial Sequence
<220> FEATURE:
<223> OTHER INFORMATION: Synthetic: reverse primer

<400> SEQUENCE: 8
aaagctgggt ctagagtcga cctagtcaac cacaagggtc tcct                 44

<210> SEQ ID NO 9
<211> LENGTH: 25
<212> TYPE: DNA
<213> ORGANISM: Artificial Sequence
<220> FEATURE:
<223> OTHER INFORMATION: Synthetic: ELA forward primer
<220> FEATURE:
<221> NAME/KEY: misc_feature
<222> LOCATION: (8)..(8)
<223> OTHER INFORMATION: n is inosine

<400> SEQUENCE: 9
ctgaggtntg tcactagaat gtgaa                                      25

<210> SEQ ID NO 10
<211> LENGTH: 24
<212> TYPE: DNA
<213> ORGANISM: Artificial Sequence
<220> FEATURE:
<223> OTHER INFORMATION: Synthetic: reverse primer

<400> SEQUENCE: 10
taagcaatca cgctgttggc atca                                       24

<210> SEQ ID NO 11
<211> LENGTH: 20
<212> TYPE: DNA
<213> ORGANISM: Artificial Sequence
<220> FEATURE:
<223> OTHER INFORMATION: Synthetic: actin forward primer

<400> SEQUENCE: 11
agaaaatctg gcaccacacc                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic: reverse primer

<400> SEQUENCE: 12
ggggtgttga aggtctcaaa                                            20

<210> SEQ ID NO 13
<211> LENGTH: 4
<212> TYPE: PRT
```

```
<213> ORGANISM: Artificial Sequence
<220> FEATURE:
<223> OTHER INFORMATION: Synthetic: linker

<400> SEQUENCE: 13

Gly Gly Gly Ser
1

<210> SEQ ID NO 14
<211> LENGTH: 5
<212> TYPE: PRT
<213> ORGANISM: Artificial Sequence
<220> FEATURE:
<223> OTHER INFORMATION: Synthetic: linker

<400> SEQUENCE: 14

Gly Gly Gly Gly Ser
1               5

<210> SEQ ID NO 15
<211> LENGTH: 13
<212> TYPE: PRT
<213> ORGANISM: Artificial Sequence
<220> FEATURE:
<223> OTHER INFORMATION: Synthetic: linker

<400> SEQUENCE: 15

Gly Gly Gly Ser Gly Gly Gly Ser Gly Gly Gly Ser
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic: integrin-binding peptide

<400> SEQUENCE: 16

Cys Tyr Gly Gly Arg Gly Asp Thr Pro
1               5
```

METHODS FOR TREATING CARDIOVASCULAR DYSFUNCTION AND IMPROVING FLUID HOMEOSTASIS WITH ELABELA PEPTIDE HORMONE

CROSS REFERENCE TO RELATED APPLICATIONS

This application is a 371 national stage application of PCT Application No. PCT/US2015/055389, filed Oct. 13, 2015, and claims the benefit of provisional application 62/063,005, entitled "Methods for Treating Cardiovascular Disease and Improving Fluid Homeostasis with a Peptide Hormone," filed Oct. 13, 2014, the entire contents of which are incorporated herein.

STATEMENT OF GOVERNMENT INTEREST

This invention was made with government support under Grant Number DK072488 awarded by the National Institutes of Health. The government has certain rights in the invention.

BACKGROUND

Each year, heart disease is one of this country's most serious health problems. The direct and indirect costs of cardiovascular disease and stroke are about $315 billion. This figure is increasing every year. Statistics show that cardiovascular disease is America's leading health problem, and the leading cause of death. Considering the most recent statistics released by the American Heart Association, approximately 84 million people in this country suffer from some form of cardiovascular disease, causing about 2,200 deaths a day, averaging one death every 40 seconds. Almost one out of every three deaths results from cardiovascular disease. An estimated 15 million U.S. adults have coronary heart disease. Approximately 78 million U.S. adults have high blood pressure, and an estimated 20 million have diabetes. It is estimated that an additional 8 million adults have undiagnosed diabetes and 87 million have pre-diabetes. It is estimated that currently 5.8 million adults in the United States are living with heart failure and its prevalence is projected to increase to 25% by 2030. The increasing prevalence of heart disease is attributed to aging of the population, increases in obesity and diabetes, and improved survival from heart failure and other cardiac diseases and conditions.

Medications that work on many different levels are available to improve heart function and include: ACE inhibitors, aldosterone antagonists, angiotensin receptor blockers, beta-blockers, calcium channel blockers, cholesterol lowering drugs, digoxin, diuretics, glucose lowering drugs, potassium or magnesium, vasopressin antagonists, and warfarin. Therapeutic agents that can enhance and/or restore heart function with large safety margins are actively sought. Furthermore, it is desirable to maintain a patient at a constant drug level over an extended period of time.

There is an urgent need to identify strategies and methods to improve cardiovascular health, heart failure survival rate, and lifespan for this growing population of patients. The present invention addresses this need.

SUMMARY

Methods are provided for treating a subject, preferably a human, that is suffering from a cardiac condition or has a risk factor for developing a cardiac condition. Treatment involves administering to the subject an effective amount of a peptide in a pharmaceutically acceptable form that selected from the group consisting of: (a) a peptide of SEQ ID NO: 1, (ELA-32), (b) a peptide of SEQ ID NO: 2, (ELA-21), (c) an Apelin peptide of SEQ ID NO: 3 (Apelin-13), (d) a fragment, or variant, or derivative at least 95% identical to the peptides (a)-(c), (e) an Elabela fusion protein of SEQ ID NO: 5 (Fc-ELA-32), (f) an Elabela fusion protein of SEQ ID NO: 6 (Fc-ELA-21), and (g) an Elabela-Apelin fusion protein or a fragment, or variant, or derivative thereof that is at least 95% identical to the peptides (e)-(g).

In certain embodiments, the cardiac condition is a result of a condition selected from the group consisting of acute decompensated heart failure (ADHF), angina, arrhythmia, atherosclerosis, atrial fibrillation, Brugada syndrome, cardiac insufficiency, cardiomyocyte apoptosis, cardiovascular disease, carditis, constricted blood vessels, cardiomyopathy, chronic heart failure, congestive heart failure, damaged blood vessels, diabetes, elevated left ventricular end-diastolic pressure, electrolyte disorder, endocarditis, fibrosis, fluid retention, heart failure, high blood sugar, hyperlipidemia; hypertension, hypoxia-induced cardiomyocyte apoptosis, ischemia, hypertrophic cardiomyopathy, kidney disease, idiopathic cardiomyopathy, leaky blood vessels, lack of vascular endothelial cells, low ejection fraction, metabolic syndrome, myocardial infarction, myocardial infarction-induced cardiomyocyte apoptosis, myocardial-induced heart failure, myocardial-induced fibrosis, palpitations, peripheral arterial disease, obesity, pulmonary hypertension, reduced cardiac function, Raynaud's disease, rheumatic heart disease restenosis, stroke, ventricular tachycardia, and heart transplant.

In other embodiments, administration of the peptides or fusion proteins as described herein may be in an amount is alone, or in combination with, a therapeutic agent selected from the group consisting of: an ACE inhibitor, an aldosterone antagonist, an angiotensin receptor blocker, a beta-blocker, a calcium channel blocker, a cholesterol lowering drug, a digoxin, a diuretic, potassium or magnesium, a vasopressin antagonist, and warfarin.

Methods are also provided for a subject suffering from a cardiac condition or has a risk factor for developing a cardiac condition comprising: (i) identifying a subject a subject suffering from a cardiac condition or having a risk factor for developing a cardiac condition; (ii) measuring an amount of a peptide of SEQ ID NO: 1, (ELA-32) or SEQ ID NO: 2, (ELA-21) or an Apelin peptide of SEQ ID NO: 3, (Apelin-13) in the circulating bloodstream of the subject in a subject suffering from a cardiac condition or having a risk factor for developing a cardiac condition; (iii) measuring an amount of a peptide of SEQ ID NO: 1, (ELA-32) or SEQ ID NO: 2, (ELA-21) or a peptide of SEQ ID NO: 3, (Apelin-13) in the circulating bloodstream of a normal control subject; (iv) comparing amounts of the peptide of SEQ ID NO: 1, (ELA-32) or the peptide of SEQ ID NO: 2, (ELA-21) or the peptide of SEQ ID NO: 3, (Apelin-13) in the subject suffering from a cardiac condition or having a risk factor for developing a cardiac condition and those in the normal control subject; and (v) treating the subject with (a) an amount of a peptide in a pharmaceutically acceptable form of SEQ ID NO: 1 (ELA-32), or SEQ ID NO: 2, (ELA-21) or a peptide of SEQ ID NO: 3 (Apelin-13), or a fragment, or variant, or derivative thereof that is at least 95% identical to the peptides of (a); or (b) a an Elabela fusion protein of SEQ ID NO: 5 (Fc-ELA-32) or an Elabela fusion protein of SEQ ID NO: 6 (Fc-ELA-21), or an Elabela-Apelin fusion protein, or a fragment, or variant, or derivative thereof that is at least 95% identical to the peptides of (b).

Fusion proteins are provided in certain embodiments and comprise from N- to C-terminus, (i) a human tissue plasminogen secretion signal peptide, (ii) a Fc domain of an immunoglobulin molecule, (iii) a hinge region, and (iv) a peptide selected from the group consisting of a peptide of SEQ ID NO: 3, or SEQ ID NO: 4, or a fragment, or a variant, or a derivative thereof that is at least 95% identical to the peptides of (iv). The fusion protein may comprise a human immunoglobulin molecule and a hinge region. In certain embodiments, the hinge region comprises at least 5, preferably 16 amino acids, at most, 20 amino acids. In other embodiments, methods of producing these fusion proteins are provided.

Pharmaceutical compositions are provided in certain embodiments and comprise (a) a peptide of SEQ ID NO: 2 (ELA-21), or fragment, or variant, or derivative thereof that is at least 95% identical to the peptides (b) or the fusion protein of claim 7 and a pharmaceutically acceptable carrier. The pharmaceutical composition of claim 15 further comprising a therapeutic agent selected from the group consisting of: an ACE inhibitor, an aldosterone antagonist, an angiotensin receptor blocker, a beta-blocker, a calcium channel blocker, a cholesterol lowering drug, a digoxin, a diuretic, a glucose lowering drug, potassium or magnesium, a vasopressin antagonist, and warfarin.

In other embodiments, methods are provided for selectively activating cardiomyocytes in vitro or in vivo, comprising contacting the cardiomyocytes with fusion proteins as described therein. The activation comprises stimulation of proliferation of cardiomyocytes.

These and other features, aspects, and advantages of the present invention will become better understood with regard to the following description, appended claims, and accompanying figures.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 3A-3C are graphs representing down-stream signaling of APJ activation by ELA.

FIG. 4A-4D are photographs and graphs illustrating stimulation of vascular tubule-like structure by ELA-APJ signaling.

FIG. 5A-5C are graphs illustrating the relaxing effect of ELA and apelin-13 on blood vessels.

FIG. 7A-7C are bar graphs and a photograph illustrating administration of ELA improves post-MI heart functions as indicated by less increase in LVDs and less decrease in LVEF.

FIG. 15A-15C are photographs illustrating Fc-ELA-32 and Fc-ELA-21 fusion proteins as functional and inducing endocytosis in vitro.

DETAILED DESCRIPTION

1. Introduction

Figure 1:
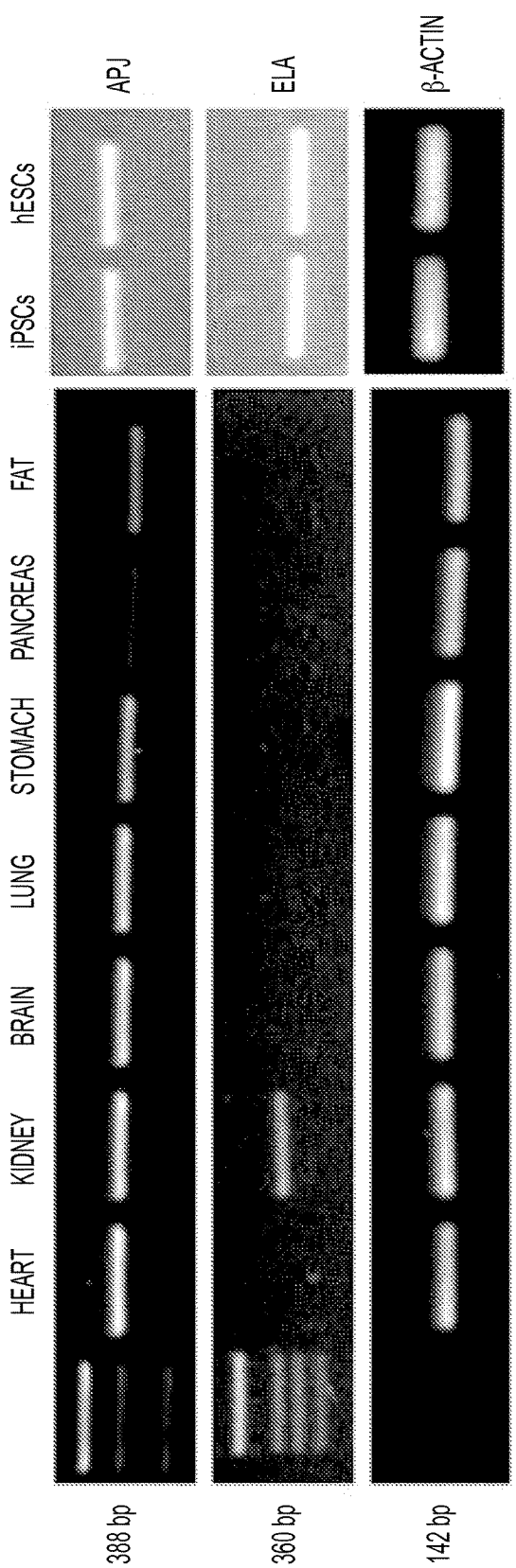
FIG. 1 is a photograph of a Western Blot showing tissue-restricted expression of ELA in the human.

Over a hundred therapeutic proteins and peptides approved by the U.S. Food and Drug Administration (FDA) are used for a wide variety of indications, ranging from rheumatoid arthritis pain, cardiovascular disease, diabetes, and depression. Many of these proteins and peptides have less than optimal pharmacokinetic properties, often because they are smaller than the kidney filtration cutoff. For virtually all of these proteins and peptides, dosing is parenteral, so each dose is represented by either a subcutaneous or intravenous injection. High dosing frequency, a small area under the curve (AUC), and patient inconvenience are limitations of short-acting peptides. Short plasma half-life times are commonly due to fast renal clearance as well as to enzymatic degradation occurring during systemic circulation. Thus, in many cases, second- or third-generation modifications of those protein or peptide drugs, intended to decrease their sensitivity to proteases and glomerular filtration by the kidney, are desired to improve pharmacokinetic profiles for more effective treatment options.

To address these shortcomings, in certain embodiments, genetic fusion of a pharmacologically active peptide or protein to a naturally long-half-life protein or protein domain (e.g., Fc fusion) provides a desired half-life. Due to the obvious advantages of long-acting peptide and protein drugs, strategies to prolong plasma half life time of such compounds are in demand. Therefore, efforts to seek these protein modifications in the development of therapeutic agents with more desirable properties are provided.

Of particular interest is the ELA peptide. ELA provides a cardiac protective function in mammals as deduced from its developmental role in cardiomyocyte formation in the zebrafish. The full-length 54-amino acid ELA peptide includes a secretory signal in its N-terminal region. After cleavage of the signal peptide which consists of the first 22 residues, the mature ELA hormone is 32 amino-acid long (ELA-32) (SEQ ID NO: 1) with an isoelectric point exceeding 12. Phylogenetic analysis revealed that the 32-amino acid mature peptide is evolutionarily highly conserved, with the last 13 residues being nearly invariant in all vertebrate species. Furthermore, the Elabela-Apelin receptor ("ELA-APJ") signaling pathways found in zebrafish are conserved and functional in mammalian cells. ELA binds and activates APJ and its activation results in cAMP suppression, ERK activation, and intracellular calcium mobilization in a dose-dependent manner, establishing that ELA acts on APJ in the human system and is required for normal cardiac development in zebrafish. The pivotal developmental role of ELA in zebrafish suggests that cardiovascular system is the main target of ELA action.

Therefore, in certain embodiments, methods are provided for treating those suffering from a cardiac condition or having a risk factor for developing a cardiac condition by administering to the subject an ELA peptide or fusion protein as described herein to a subject in need. More particularly, the embodiments relate to fusion proteins and methods of making them that assist in prolonging the half-life of ELA in the blood stream and have improved properties for use as therapeutic agents, e.g. in the treatment of cardiac conditions. The embodiments further relate to methods for producing the fusion proteins described herein, and to methods of using them in the treatment of diseases such as cardiovascular disease and diabetes.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

2. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques in certain embodiments are generally performed according to conventional methods well known in the art and as described in various general and more specific references that are cited and discussed throughout the present specification unless otherwise indicated. See, e.g., Sambrook, et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The terms "a," "an," "the" and similar terms as used herein in the context of certain embodiments (especially in the context of the claims) are to be construed to cover both the singular and plural unless otherwise indicated herein or clearly contradicted by the context.

The term "apelin," as used herein is a 77 residue pre protein (NCBI Reference Sequence: NP_0059109.3, and encoded by NCBI Reference Sequence: NM_017413.3), which is processed into biologically active forms of apelin peptides, such as apelin-36, apelin-17, apelin-16, apelin-13, (SEQ ID NO: 3) and apelin-12. The full length mature peptide, referred to as "apelin-36," comprises 36 amino acids, but the most potent isoform is the pyroglutamated form of a 13 mer of apelin (apelin-13), referred to as "Pyr-1-apelin-13 or Pyr$^1$-apelin-13," Different apelin forms are described, for instance, in U.S. Pat. No. 6,492,324B1, which is hereby incorporated by reference in its entirety.

The terms "apelin receptor," "angiotension-like-1 receptor," "angiotensin II-like-1 receptor," (APJ) as used herein refers to a 380 residue, 7 transmembrane domain, Gi coupled receptor whose gene is localized on the long arm of chromosome 11 in humans (NCBI Reference Sequence: NP_005152.1, and encoded by NCBI Reference Sequence: NM_005161). APJ was first cloned in 1993 from genomic human DNA using degenerate oligonucleotide primers (O'Dowd et al. Gene, 136: 355-60, 1993) and shares significant homology with angiotensin II receptor type 1. Despite this homology however, angiotensin II does not bind APJ. Although orphan for many years, the endogenous ligand has been isolated and named apelin (Tatemoto et al., Biochem Biophys Res Commun 251, 471-6 (1998)).

The term "has a risk factor for" as used herein means a subject is at risk of developing a cardiac condition because of a pre-existing genetic condition, family history, or lifestyle factors, including but not limited to, being postmenopausal for women, being older than 45 for men, diabetes or hyperglycemia, excess alcohol consumption, kidney disorders, obesity, smoking, stress, thyroid gland and adrenal gland dysfunction, total blood cholesterol above 250 mg/dL, LDL cholesterol above 130 mg/dL (3.0 mmol/L), HDL cholesterol below 35 mg/dL and lipoprotein(a) level greater than 30 mg/dL.

The term "cardiac disease" or "cardiac condition" as used herein means a condition or disease of the heart in a subject that is a result of or characterized by any one of or combination of the following: acute decompensated heart failure (ADHF), angina, arrhythmia, atherosclerosis, atrial fibrillation, Brugada syndrome, cardiac insufficiency, cardiomyocyte apoptosis, cardiovascular disease, carditis, congenital defect, constricted blood vessels, cardiomyopathy, chronic heart failure, congestive heart failure, damaged blood vessels, diabetes, elevated left ventricular end-diastolic pressure, endocarditis, fibrosis, fluid retention, heart failure, high blood sugar, hyperlipidemia; hypertension, hypoxia-induced cardiomyocyte apoptosis, ischemia, hypertrophic cardiomyopathy, idiopathic cardiomyopathy, leaky blood vessels, lack of vascular endothelial cells, low ejection fraction, metabolic syndrome, myocardial infarction, myocardial infarction-induced cardiomyocyte apoptosis, myocardial-induced heart failure, myocardial-induced fibrosis, palpitations, peripheral arterial disease, obesity, pulmonary hypertension, reduced cardiac function, Raynaud's disease, rheumatic heart disease restenosis, stroke, ventricular tachycardia and heart transplant.

The terms "effective amount" or "therapeutically effective amount" as used herein have the standard meanings known in the art and are used interchangeably herein to mean an amount sufficient to treat a subject afflicted with a condition or disease (e.g., heart failure, diabetes) or to halt the progression of the condition or disease, or alleviate a symptom or a complication associated with the condition or disease. The exact dose will depend on the purpose of the treatment, and will be ascertainable by one skilled in the art using known techniques (e.g., Ansel et al., Pharmaceutical Dosage Forms and Drug Delivery; Lieberman, Pharmaceutical Dosage Forms (vols. 1-3, 1992), Dekker, ISBN 0824770846, 082476918X, 0824712692, 0824716981; Lloyd, The Art, Science and Technology of Pharmaceutical Compounding (1999); and Pickar, Dosage Calculations (1999)). For example, in the case of an agent to treat heart failure, an effective amount may be an amount sufficient to result in clinical improvement of the patient, e.g., increased exercise tolerance/capacity, decreased blood pressure, decreased fluid retention, and/or improved results on a quantitative test of cardiac functioning, e.g., ejection fraction, exercise capacity (time to exhaustion).

The term Elabela ("ELA" or "Ela") as used herein refers a hormone or mature form consisting of 32 amino acid peptides (SEQ ID NO: 1) as well as 21 amino acids (SEQ ID NO: 2) found in humans as well as other vertebrates and is considered to play an important role in the circulatory system through the apelin receptor (APJ).

The term "immunoglobulin molecule" as used herein means a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each immunoglobulin heavy chain has a variable region (VH), also called a variable heavy domain or a heavy chain variable domain, followed by three constant domains (CH1, CH2, and CH3), and also called a heavy chain constant region. Similarly, from N- to C-terminus, each immunoglobulin light chain has a variable region (VL), also called a variable light domain or a light chain variable domain, and followed by a constant light (CL) domain, also called a light chain constant region. The heavy chain of an immunoglobulin may be assigned to one of five classes, called α, (IgA), Δ, ε, γ, and μ, (IgD), ε, (IgE), γ, (IgG), or μ, (IgM), some of which may be further divided into subclasses, e.g. γ1 (IgG1), γ2 (IgG2), γ3 (IgG3), γ4 (IgG4), α1 (IgA1) and α2 (IgA2). The light chain of an immunoglobulin may be assigned to one of two types, called kappa (κ) and lambda (λ) based on the amino acid sequence of its constant domain. An immunoglobulin essentially consists of two Fab molecules and an Fc domain, linked via the immunoglobulin hinge region.

The terms "Fc domain" or "Fc region" as used herein refer to a C-terminal region of an immunoglobulin heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG).

The term "fusion protein" as used herein refers to a polypeptide molecule which contains two or more peptide sequences that are not naturally linked together, but which have been linked to each other by peptide bonds, either directly or through peptide linkers or hinge regions. The individual peptide chains of the immunoglobulin component of the fusion protein may be linked non-covalently, e.g. by disulfide bonds. Fusion proteins can be created through the joining of two or more genes that originally coded for separate proteins or of two or more of artificially designed peptides or proteins. In certain embodiments, fusion proteins may include an ELA peptide linked to an Fc region or ELA linked to Apelin, including but not limited to Fc-ELA-32 (SEQ ID NO: 4), Fc-ELA-21 (SEQ ID NO: 5) and an Elabela-Apelin fusion protein.

The term "fused" as used herein refers to components that are linked by peptide bonds, either directly or via one or more peptide linkers or a hinge region.

The terms "host cell," "host cell line," and "host cell culture," as used herein are interchangeable and refer to cells into which exogenous nucleic acid has been introduced, including the progeny of such cells. A host cell is any type of cellular system that can be used to generate the fusion proteins in certain embodiments. Host cells include cultured cells, e.g. mammalian cultured cells, such as HEK293, HEK293T, CHO cells, BHK cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

The terms "myocardial infarction" (MI) or "heart attack" as used herein are characterized by the death of myocytes, coagulative necrosis, myocytolysis, contraction band necrosis, or apoptosis, resulting from a critical imbalance between the oxygen supply and demand of the myocardium. The most common cause of MI is coronary artery thrombosis following the rupture of atheromatous plaques. Though once strictly defined as a lack of blood flow, the modern definition of ischemia emphasizes the imbalance between oxygen supply and demand as well as the inadequate removal of metabolic waste products. The terms "heart failure after acute MI" or "post-infarct heart failure" or "post-MI heart failure" refer to the patients who survived from acute MI but progress with heart failure later. An increasing pool of survivors of AMI might fuel an "epidemic" of heart failure and cardiovascular death). Rats and mice with permanent ligation of left anterior descending coronary artery are generally used animal models of post-MI heart failure in humans.

The term "modification" as used herein refers to any manipulation of the peptide backbone (e.g. amino acid sequence) or the post-translational modifications (e.g. glycosylation) of a polypeptide.

The terms "peptide linker" or "hinge region" as used herein refers to a peptide comprising one or more amino acids, typically about 2-20 amino acids which are placed between other peptides in a sequence. Peptide linkers are known in the art or are described herein.

The term "pharmaceutical composition" as used herein refers to a preparation which is in such form as to permit the biological activity of an active ingredient contained therein to be effective, and which contains no additional components which are unacceptably toxic to a subject to which the formulation would be administered.

The term "pharmaceutically acceptable carrier" as used herein refers to an ingredient in a pharmaceutical composition, other than an active ingredient, which is nontoxic to a subject. A pharmaceutically acceptable carrier includes, but is not limited to any solid, liquid or gaseous vehicle, including, for example, a buffer, excipient, stabilizer, or preservative.

The terms "polypeptide" and "protein" as used herein are used interchangeably, unless specified to the contrary, and according to conventional meaning, mean a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring.

The term "subject" as used herein refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. A subject in need is a subject that is suffering from a cardiac condition or disease or that has a risk factor for developing a cardiac condition or cardiac disease.

The term "therapeutic agent" as used herein is a compound capable of producing an desired and beneficial effect.

The terms "treat," "treating" or "treatment" of any disease or disorder as used herein refer in one embodiment, to halting the progression of the condition or disease, or to ameliorating the disease or disorder (i.e., slowing or arresting or reducing the development of the disease or at least one of the clinical symptoms thereof). In another embodiment "treat," "treating" or "treatment" refers to alleviating or ameliorating at least one physical parameter including those which may not be discernible by the patient. In yet another embodiment, "treat," "treating" or "treatment" refers to modulating the disease or disorder, either physically, (e.g., stabilization of a discernible symptom), physiologically, (e.g., stabilization of a physical parameter), or both. In yet another embodiment, "treat," "treating" or "treatment" refers to preventing or delaying the onset or development or progression of the disease or disorder. As used herein, a subject is "in need of" a treatment if such subject would benefit biologically, medically or in quality of life from such treatment.

The term "vector" as used herein refers to any molecule or entity (e.g., nucleic acid, plasmid, bacteriophage or virus) used to transfer protein coding information into a host cell. Certain vectors are capable of directing the expression of nucleic acids to which they are operatively linked. Such vectors are referred to herein as "expression vectors." An "expression vector" or "expression construct" as used herein refers to a recombinant DNA molecule containing a desired coding sequence and appropriate nucleic acid control sequences necessary for the expression of the operably linked coding sequence in a particular host cell.

3. Overview

ELA plays an essential role for normal cardiovascular system development during embryonic development in mice as it does in zebrafish. In human adults, ELA transcripts are found only in the kidney and prostate. RT-PCR analysis directly demonstrated that ELA is selectively expressed in human kidney as well as in pluripotent stem cells. Therefore, the predominant expression of ELA in kidney is in line with the essential role of ELA in cardiovascular system development because the kidney, together with the heart, function to maintain fluid balance and blood pressure. Thus, ELA can act as a paracrine or endocrine hormone regulating the circulation system. In additions to methods of treating a subject suffering from or a subject at risk of a cardiac condition, embodiments can be used to promote angiogenesis, relax blood vessels, regulate fluid homeostasis, improve cardiac performance in an infarcted heart, improve diuresis, mitigate cardiac damage induced by MI, reduce fibrosis in an infarcted heart, increase cardiomyocyte proliferation, and reduce apoptosis, all of which are desirable effects.

4. Detailed Description of the Embodiments

It is therefore desirable to provide methods of treating cardiac conditions by administering a peptide (e.g., ELA-32, ELA-21, or Apelin-13) or fusion protein (e.g., Fc-ELA-32, Fc-ELA-21) to a subject in need (e.g., SEQ ID NOs: 1-5) in certain embodiments as set forth below.

```
ELA-32
                                             (SEQ ID NO: 1)
QRPVNLTMRRKLRKHNCLQRRCMPLHSRVPFP

ELA-21
                                             (SEQ ID NO: 2)
SLRKHNCLQRRCMPLHSRVPFP

Apelin-13
                                             (SEQ ID NO: 3)
QRPRLSHKGPMPF Fc-ELA-32 or "htPA-SS-Fc-ELA-32"
                                             (SEQ ID NO: 4)
MDAMKRGLCCVLLLCGAVFVSPSQDIDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPVPIEKTISKAKGQPR
```

-continued
EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGKGGGGSGGGGSGGGGSQRPVNLTMRRKLRKHNCLQRRCMPLHSRVPFP

Fc-ELA-21 or "htPA-SS-Fc-ELA-21"
(SEQ ID NO: 5)
MDAMKRGLCCVLLLCGAVFVSPSQDIDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPVPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGKGGGGSGGGGSGGGGSLRKHNCLQRRCMPLHSRVPFP

More particularly, embodiments relate to ELA fusion proteins of, compositions, and kits comprising them. The fusion proteins exhibit improved properties for use as therapeutic agents, e.g. in the treatment of cardiac conditions. In addition, certain embodiments relate to polynucleotides encoding such fusion proteins, vectors, and host cells comprising such polynucleotides. Embodiments further relate to methods for producing the fusion proteins described herein as well as methods of using them in the treatment of disease.

A. Methods of Treatment a. Cardiac Conditions

In certain embodiments, methods are provided for treating cardiac conditions in a subject or in a subject (preferably a mammal such as a human) having a risk factor for developing a cardiac condition by administering an ELA peptide (ELA-32, ELA-21), an Apelin peptide (e.g., Apelin-13) or ELA fusion protein (e.g., Fc-ELA-32, Fc-ELA-21, Elabela-Apelin) as described herein. The cardiac condition or risk factor for the cardiac condition includes, but is not limited to acute decompensated heart failure (ADHF), angina, arrhythmia, atherosclerosis, atrial fibrillation, Brugada syndrome, cardiac insufficiency, cardiomyocyte apoptosis, cardiovascular disease, carditis, constricted blood vessels, cardiomyopathy, chronic heart failure, congestive heart failure, damaged blood vessels, diabetes, elevated left ventricular end-diastolic pressure, electrolyte disorder, endocarditis, fibrosis, fluid retention, heart failure, high blood sugar, hyperlipidemia; hypertension, hypoxia-induced cardiomyocyte apoptosis, ischemia, hypertrophic cardiomyopathy, kidney disease, idiopathic cardiomyopathy, leaky blood vessels, lack of vascular endothelial cells, low ejection fraction, metabolic syndrome, myocardial infarction, myocardial infarction-induced cardiomyocyte apoptosis, myocardial-induced heart failure, myocardial-induced fibrosis, palpitations, peripheral arterial disease, obesity, pulmonary hypertension, reduced cardiac function, Raynaud's disease, rheumatic heart disease restenosis, stroke, ventricular tachycardia, and heart transplant.

In certain embodiments, a subject suffering from a cardiac condition or having a risk factor for developing a cardiac condition is identified. Amounts of a peptide of SEQ ID NO: 1 (ELA-32), or a peptide of SEQ ID NO: 2 (ELA-21), or a peptide of SEQ ID NO: 3 (Apelin-13), in the bloodstream of the subject suffering from a cardiac condition or having a risk factor for developing a cardiac condition are measured. Then, amounts of a peptide of SEQ ID NO: 1, or a peptide of SEQ ID NO: 2, or a peptide of SEQ ID NO: 3, in the bloodstream of a normal control subject are measured. Both the amounts of the peptide of SEQ ID NO: 1, or SEQ ID NO: 2, or SEQ ID NO: 3, in the subject suffering from a cardiac condition or having a risk factor for developing a cardiac condition are compared with those in the normal control subject. If it is determined that the amount of peptide can be significantly decreased from that of the control subject, then the is treated with (a) a peptide of SEQ ID NO: 1, a peptide of SEQ ID NO: 2, or a peptide of SEQ ID NO: 3, a fragment, or variant, or derivative thereof that is at least 95% identical to the peptides of (a) or (b) a composition comprising an ELA fusion protein of SEQ ID NO: 5, of SEQ ID NO: 6, and Elabela-Apelin fusion protein or a fragment, or variant, or derivative thereof that is at least 95% identical to the peptides of (b).

In other embodiments, an ELA peptide or fusion protein described herein improves heart performance in subjects with MI-induced heart failure. As seen in Example 8, coronary artery ligation (CAL) is a well-used procedure to create a mouse model of acute myocardial infarction (MI) and consequent heart failure (HF). ELA peptide was infused. High-frequency echocardiography was conducted to measure heart geometry and function before and post-MI. As expected, MI resulted in left ventricular dilation and contractile dysfunction, hallmarks in development of congestive heart failure following MI, which were indicated by an increase of the left ventricle chamber size (LVDs and LVDd) and a decrease of left ventricular ejection fraction (LVEF) and fractional shortening (see Table 1 and FIG. 7A-FIG. 7C). ELA administration mitigates the development of left ventricular dilation and contractile dysfunction (see Table 1 and FIG. 7A-FIG. 7C), suggesting a novel cardioprotective strategy in mice with post-MI heart failure.

In addition, administration of a ELA peptide or fusion protein as described herein can be used to promote angiogenesis, dilate blood vessels, regulate fluid homeostasis, improve diuresis, mitigate cardiac damage induced by MI, reduce fibrosis in an infarcted heart, increase cardiomyocyte proliferation, and reduce apoptosis, all of which are desirable effects.

For example, in other embodiments, an ELA peptide (e.g., ELA-32, ELA-21, Apelin-13) or fusion protein (Fc-ELA-32, Fc-ELA-21, Elabela-Apelin) described herein improves diuresis. During heart failure, the decrease in left ventricular (LV) systolic and diastolic function results in reduced cardiac output, stroke volume and intra-arterial blood volume leads to a compensatory activation of the sympathoadrenal system and release of a cascade of neurohormones. The overall results in fluid retention and volume increase, which in turn overloads heart and constitutes a vicious cycle to heart and kidney dysfunction and failure. Vasopressin and aldosterone are two major hormones to increase water and sodium retention during heart failure. New diuretics of anti-vasopressin and anti-aldosterone are being developed for treatment of heart failure by reducing fluid overload. Since ELA is specifically expressed in the kidney and can suppress the production of cAMP, a cellular signaling molecule, whereas vasopressin increases cAMP.

Aldosterone is a hormone produced in the adrenal gland and functions to cause renal sodium reabsorption and water retention in response to angiotensin II (Ang II) stimulation. Anti-aldosterone is a therapeutic approach for heart failure. Since the activation of apelin reception is found to antagonize Ang II effects, ELA affects Ang II-mediated aldosterone synthesis. Human HAC15 cells, a line of adrenal cortical carcinoma. As shown in Example 11, treatment with ELA, apelin-13 and angiotensin II alone or in combination, significantly suppressed the Ang II-induced gene expression of aldosterone synthase. Without being bound by theory, ELA may exert anti-heart activity by reducing aldosterone levels.

In certain embodiments, ELA-Fc fusion proteins (Fc-ELA-32, Fc-ELA-21, Elabela-Apelin) mitigates heart damage induced by MI. Like most short peptides, ELA is likely to have a short half-life in circulation because of tissue absorption, degradation and renal elimination. Protein fusion is a method to prolong the half-life of a peptide or protein. Thus, fusion proteins as described in Example 8 are administered. Fc-ELA-32 fusion protein has cardioprotective effects in heart failure caused by MI. A failing heart induced by CAL in laboratory animals exhibits alterations in morphological structure and biochemical sequelae as seen in humans with post-MI heart failure, including cardiomyocyte death, formation of the scar tissue, and ventricular remodeling. Cardiac performances and tissue responses change during the course of remodeling in the acute and remodeling phase.

ELA reduces left ventricular end-diastolic pressure (LVEDP), which indicates improved left ventricular compliance, and global performance. Following myocardial infarction (MI), indeed, LVEDP elevation was associated with larger infarct size and increased circulatory volume. In certain embodiments, Fc-ELA-32 administration decreased LVEDP, indicating an improvement of the dysfunctional heart (See Example 12). ELA also reduces heart fibrosis as further described in Example 13. One common features of the failing heart is myocardial fibrosis. Myocardial fibrosis is associated with worsening ventricular systolic function, cardiac remodeling, and increased ventricular stiffness in animals and patients. In certain embodiments, Collagen volume fraction (CVF) is significantly decreased in Fc-ELA-32-treated subjects indicating that Fc-ELA suppresses fibrosis of the infarcted heart.

In certain embodiments, ELA reduces apoptosis. As described in Example 14, cardiomyocytes treated with Fc-ELA-32 can increase cardiomyocyte proliferation near the infarct region and reduce apoptosis. Apoptosis is a main mechanism of cell death caused by ischemia during myocardial infarction. An ELA-treated subject is protected against MI-induced cardiomyocyte apoptosis.

b. Diabetes

Methods for treating diabetes are also contemplated in certain embodiments. The subject suffering diabetes or having a risk factor for developing a cardiac condition due to diabetes is treated with administration of an ELA peptide fusion protein (Fc-ELA-32, Fc-ELA-21, Elabela-Apelin) as described herein. The ELA peptide or fusion protein upon administration can lower glucose levels and improve insulin sensitivity. Thus, heart stroke volume in obese subjects without heart failure can be increased.

B. Fusion Proteins

Provided below are Fc-based fusion proteins that are composed of an immunoglobin Fc domain that is directly linked to ELA peptide (i.e., Fc-ELA-32, Fc-ELA-21). In other embodiments, the fused partner can be any other proteinaceous molecule of interest, such as a ligand that activates upon interaction with a cell-surface receptor, a peptidic antigen against a challenging pathogen or a protein to identify binding partners assembled in a protein microarray. Most frequently though, and as is the case here, the fused partner has significant therapeutic potential, and is attached to an Fc-domain to armor the hybrid with a number of additional beneficial biological and pharmacological properties.

The primary reason for fusion of a binding moiety with Fc is half-life extension. Therapeutic agents (e.g., drugs) vary in how long it takes to clear them from the body. Some are metabolized fairly quickly, while others can take a long time before they are eliminated. This is quantitated with the use of the term "half-life." The half-life of a given therapeutic agent is how long it takes for the body to metabolize or excrete half of the dose. When the patient is taking a drug on a regular basis, there is an ongoing process of drug absorption in the form of each dose of the drug and, concurrently, an ongoing process of drug removal with the drug's metabolism and clearance. Eventually, an equilibrium or steady-state occurs. Generally, it takes somewhere between 5 and 6 half-lives for a drug to reach steady state. Medications with short half-lives reach steady state relatively quickly, while those with long half-lives take a long time to reach steady state. Many biologically active proteins and peptides have very short serum half-lives due to fast renal clearance, which limits their exposure in the target tissue and, consequently, their pharmacological effects. The Fc domain prolongs the serum half-life of antibodies, and Fc-fusion proteins, due to pH-dependent binding to Fc receptors, which salvage the protein from being degraded in endosomes. As an additional benefit, the Fc portion of Fc-fusion proteins allows easier expression and protein A-affinity purification, which confers practical advantages in the production of antibody and Fc-fusion therapeutics.

In certain embodiments, the presence of the Fc domain markedly increases the plasma half-life, which prolongs therapeutic activity, as well as to the slower renal clearance for larger sized molecules. In certain embodiments, from a biological perspective, the Fc domain folds independently and can improve the solubility and stability of the partner molecule both in vitro and in vivo, while from a technological viewpoint, the Fc region allows for easy cost-effective purification by protein-G/A affinity chromatography during manufacture. Thus an increase in avidity, and with it potency, from an isolated fused partner is also a significant advantage of Fc-fusion proteins.

Fc-fusions are usually homodimers in which an Fc domain of an antibody is covalently linked to another protein (i.e., an Elabela protein). The fusion partner is usually directly attached to the flexible hinge region, the length and sequence of which varies between different IgG subclasses.

A number of specific changes to a fusion protein can be made to improve efficacy. For example, Fc-fusions can also be polymerized through engineered disulphide bridges localized to the CH2-CH3 junction and 18 amino-acid carboxy-terminal extensions known as tailpieces. Modifications to the Fc-domain can generally improve therapeutic function, and subtle binding properties also make a dominating contribution to the ultimate activity of the compound in the clinical setting. In certain embodiments, identification of the optimal binding properties of the fused protein for its intended receptor may prove an essential step in the development of the drug for a desired clinical activity. In addition, whether or not the fused protein even retains its biological activity when attached to an Fc domain depends on many factors that need to be determined for each molecule. In order to improve the chances for a stable fused protein, for some proteins, it may be necessary to include a 'chaperone' protein whose presence stabilizes the desired protein. In other embodiments, it is important that the target molecule can bind with sufficient affinity to its cognate protein when situated in the homodimeric Fc-fusion architecture. One way this may be overcome is by engineering multiple specificities and/or avidity into the Fc-fusion construct. The development of heterodimeric Fc platforms based on strand-exchange engineered domains (SEED) CH3 heterodimers composed of alternating segments of human IgA and IgG CH3 sequences may allow for the development of multiple specificities within the existing homodimeric Fc-fusion platform.

Other than genetic fusion to the Fc-domain of IgG, a number of protein half-life extension strategies can be employed in other embodiments including chemical conjugation, or genetic fusion to high molecular weight polymers, and genetic fusion to albumin. Fc- and albumin fusion increase protein half-life by increasing the size (e.g. hydrodynamic radius) of the modified protein and in turn reducing renal clearance.

In one particular embodiment, Fc-fusion proteins comprise an ELA peptide as described herein to extend the half-life of ELA. The fusion protein, Fc-ELA-32 of SEQ ID NO: 4, comprises the 32-amino acid ELA peptide. The fusion protein, Fc-ELA-21 of SEQ ID NO: 5, comprises the 21-amino acid ELA peptide. Also, the Elabela-Apelin fusion protein comprises an Elabela peptide and an Apelin peptide.

In certain embodiments, the immunoglobulin molecule and ELA-32 and ELA-21 peptides are human and are fused to the immunoglobulin molecule through a short flexible peptide linker or hinge region at their N-terminal amino acids to the C-terminal amino acid of one of the immunoglobulin heavy chains. In one embodiment, each of ELA-32 or ELA-21 peptides is fused to the immunoglobulin molecule through a peptide linker or hinge region having an identical amino acid sequence. In other embodiments, the peptide linker or hinge region comprises at least 5 amino acids. In a particular embodiment, the peptide linker comprises at least 10 amino acids. Without wishing to be bound by theory, a peptide linker or hinge region of this length may provide the flexibility for optimal binding of the ELA peptides to the APJ receptor.

The "hinge region," "linker," or "linker moiety," as used interchangeably herein, refers to a biologically acceptable peptidyl or non-peptidyl organic group that is covalently bound to an amino acid residue of a polypeptide chain (e.g., Fc domain) contained in the inventive composition, which linker moiety covalently joins or conjugates the polypeptide chain to another peptide or polypeptide chain in the molecule, or to a therapeutic moiety. The presence of any hinge region in the immunoglobulins in certain embodiments may be optional. When present, the chemical structure is not critical, since it serves primarily as a spacer to position, join, connect, or optimize presentation or position of one functional moiety in relation to one or more other functional moieties of a molecule of the inventive immunoglobulin. The presence of a hinge region can be useful in optimizing pharmacological activity of some embodiments of the immunoglobulin (including antibodies and antibody fragments). The hinge region is preferably made up of amino acids linked together by peptide bonds. If present, it can be independently the same or different from any other hinge region, or hinge regions, that may be present in the inventive immunoglobulin.

In certain embodiments, the hinge region if present (whether within the primary amino acid sequence of the immunoglobulin, or as a linker for attaching a therapeutic moiety or half-life extending moiety to the inventive immunoglobulin), can be made up of amino acids linked together by peptide bonds and made up in length, preferably, of from 1 up to about 40 amino acid residues, more preferably, of from 1 up to about 20 amino acid residues, and most preferably of from 1 up to about 10 amino acid residues. Preferably, but not necessarily, the amino acid residues in the linker are cysteine, glycine, alanine, proline, asparagine, glutamine, and/or serine. Even more preferably, a peptidyl linker is made up of a majority of amino acids that are sterically unhindered, such as glycine, serine, and alanine, linked by a peptide bond. In other embodiments, the 1 to 40 amino acids of the peptidyl linker moiety are selected from glycine, alanine, proline, asparagine, glutamine, and lysine. Preferably, a linker is made up of a majority of amino acids that are sterically unhindered, such as glycine and alanine. Thus, preferred linkers include polyglycines, polyserines, and polyalanines, or combinations of any of these.

In a specific embodiment, the peptide linker or hinge region comprises 15 amino acids. In a particular embodiment, the peptide linker or hinge region comprises the sequence SGGGGS (SEQ ID NO: 6). One of ordinary skill in the art has a variety to choose from including, but not limited to the following as provided by the HTML document Linker in folder Protein domains at subdomain parts of the domain igem of the super domain org.

| | |
|---|---|
| BBa_J176131 | PLrigid |
| BBa_J18920 | 2aa GS linker |
| BBa_J18921 | 6aa [GS]x linker |
| BBa_J18922 | 10aa [GS]x linker |
| BBa_K105012 | 10 aa flexible protein domain linker |
| BBa_K133132 | 8 aa protein domain linker |
| BBa_K1486003 | Flexible linker 2x (GGGS) (SEQ ID NO:13) |
| BBa_K1486004 | flexible linker 2x (GGGGS) (SEQ ID NO:14) |
| BBa_K1486037 | 13 amino acids linker (GGGS GGGGS GGGS) (SEQ ID NO: 15) |

Fusion of the ELA-32 and ELA-21 peptides to an immunoglobulin molecule provides for favorable pharmacokinetic properties, including a long serum half-life, as compared to free (unfused) ELA-32 or ELA-21. Furthermore, the presence of an immunoglobulin molecule also enables simple purification of fusion proteins by e.g. affinity chromatography. Fusion to an immunoglobulin molecule, i.e. a naturally occurring type of molecule, may also minimize toxicity of the fusion protein through the formation of anti-drug antibodies.

As shown in the Examples, the fusion protein of certain embodiments selectively activates the APJ receptor. Thus, in one aspect certain embodiments provide a fusion protein comprising an immunoglobulin molecule and an ELA-32 peptide or ELA-21 peptide, for use in selective activation of APJ and protection of cardiomyocytes in vitro or in vivo. Immunofluorescent staining in heart tissue slides provides a method for examining cardiomyocyte responses to ELA treatment. APJ-expressing HEK293 cells are contacted with fusion protein in vitro. In one embodiment, the use is in vitro and the fusion protein is used at a concentration of about 0.2 M or less. In another embodiment, the use is in vivo and the fusion protein is used at a dose of about 300 μg/kg body weight or less, (wherein "body weight" refers to the body weight of the individual to whom the fusion protein is administered). Cardiomyocytes that respond to Fc-ELA-32 treatment proliferate in an infarct region. (See, e.g., Example 14).

C. Methods of Producing Fusion Proteins

Strategies for producing fusion proteins that may be used include: (i) genetic fusion of the pharmacologically active peptide or protein to a naturally long-half-life protein or protein domain (e.g., Fc fusion, transferrin [Tf] fusion, or albumin fusion), (ii) genetic fusion of the pharmacologically active peptide or protein to an inert polypeptide, which is also known as recombinant PEG or "rPEG", or a homo-amino acid polymer (HAP; HAPylation), a proline-alanine-serine polymer (PAS; PASylation), or an elastin-like peptide (ELP; ELPylation). Increasing the hydrodynamic radius by chemical conjugation of the pharmacologically active peptide or protein to repeat chemical moieties, e.g., to PEG (PEGylation or hyaluronic acid are other options. Significantly increasing the negative charge of fusing the pharmacologically active peptide or protein by polysialylation or, alternatively, fusing a negatively charged, highly sialylated peptide (e.g., carboxy-terminal peptide (CTP; of chorionic gonadotropin (CG) β-chain), known to extend the half-life of natural proteins such as human CG β-subunit, to the biological drug candidate. Binding non-covalently, via attachment of a peptide or protein-binding domain to the bioactive protein, to normally long-half-life proteins such as HSA, human IgG, or possibly transferrin is an option. Chemical conjugation of peptides or small molecules to long-half-life proteins such as human IgGs, Fc moieties, or HAS is a further option.

Certain embodiments provide methods for preparing these ELA peptide fusion proteins using Fc fusion. The fusion proteins may be made in a variety of ways. Since many of the compounds will be peptides, or will include a peptide, methods for synthesizing peptides are of particular relevance here. For example, solid phase synthesis techniques may be used. Suitable techniques are well known in the art, and include those described in Merrifield, in Chem. Polypeptides, pp. 335-61 (Katsoyannis and Panayotis eds. 1973); Merrifield, J. Am. Chem. Soc. 85:2149 (1963); Davis et al., Biochem. Intl. 10:394-414 (1985); Stewart and Young, Solid Phase Peptide Synthesis (1969); U.S. Pat. No. 3,941,763; Finn et al., The Proteins, 3rd ed., vol. 2, pp. 105-253 (1976); and Erickson et al., The Proteins, 3rd ed., vol. 2, pp. 257-527 (1976). Solid phase synthesis is the preferred technique of making individual peptides since it is the most cost-effective method of making small peptides.

The peptides may also be made in transformed host cells using recombinant DNA techniques. To do so, a recombinant DNA molecule coding for the peptide is prepared. Methods of preparing such DNA and/or RNA molecules are well known in the art. For instance, sequences coding for the peptides could be excised from DNA using suitable restriction enzymes. The relevant sequences can be created using the polymerase chain reaction (PCR) with the inclusion of useful restriction sites for subsequent cloning. Alternatively, the DNA/RNA molecule could be synthesized using chemical synthesis techniques, such as the phosphoramidite method. Also, a combination of these techniques could be used.

Certain embodiments also include a vector encoding the peptides in an appropriate host. The vector comprises the DNA molecule that encodes the peptides operatively linked to appropriate expression control sequences. Methods of affecting this operative linking, either before or after the peptide-encoding DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector comprising the peptide-encoding DNA molecule is used to transform an appropriate host. This transformation may be performed using methods well known in the art.

Any of a large number of available and well-known host cells may be used in the practice of these embodiments. The selection of a particular host is dependent upon a number of factors recognized by the art. These factors include, for example, compatibility with the chosen expression vector, toxicity to the host cell of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence.

Next, the transformed host is cultured under conditions so that the desired peptides are expressed. Such conditions are well known in the art. Finally, the peptides are purified from the fermentation culture or from the host cells in which they are expressed. These purification methods are also well known in the art. Fusion proteins prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the fusion protein binds. For example, for affinity chromatography purification of fusion proteins in certain embodiments, a matrix with protein A or protein G may be used. Sequential Protein A or G affinity chromatography and size exclusion chromatography can be used to isolate a fusion protein essentially as described in the Example 1.

In a preferred embodiment, a method of producing a fusion protein in certain embodiments is provided, wherein the method comprises culturing a host cell comprising a polynucleotide encoding the fusion protein, as provided herein, under conditions suitable for expression of the fusion protein, and recovering the fusion protein from the host cell (or host cell culture medium). In the fusion proteins of certain embodiments, the components (immunoglobulin molecule and ELA-32 peptide or ELA-21 peptide) are genetically fused to each other. For example, from N- to C-terminus, a human tissue plasminogen activator (tPA) secretion signal ("htPA-ss") peptide is fused with an Fc domain of an immunoglobulin molecule. Then, the htPA-ss-Fc portion is fused with ELA-21 peptide or a fragment, or variant, or derivative thereof that is at least 95% identical to the peptides to arrive at a htPA-ss-Fc-ELA-32 having SEQ ID NO: 4 or fusion protein or htPA-ss-Fc-ELA-21 fusion protein of SEQ ID NO: 5. In other embodiments, fusion proteins can be designed such that its components are fused directly to each other or indirectly through a linker sequence. As discussed above, the composition and length of the linker may be determined in accordance with methods well known in the art and may be tested for efficacy. Additional sequences may also be included to incorporate a cleavage site to separate the individual components of the fusion protein if desired, for example an endopeptidase recognition sequence. In each of the above cases Fc is preferably the Fc region of the human immunoglobulin IgG1 heavy chain or a biologically active fragment, derivative, or dimer thereof.

The Fc fusions may be at the N or C terminus or at both the N and C termini of the peptides. It has been surprisingly discovered that peptides in which an Fc moiety is ligated to the N terminus is more bioactive than the other possibilities, so the fusion having an Fc domain at the N terminus is preferred. When the Fc chain is fused at the N-terminus of the peptide or linker, such fusion will generally occur at the C-terminus of the Fc chain, and vice versa.

Any animal species of immunoglobulin can be used in embodiments to obtain the Fc region. Non-limiting immunoglobulins useful in the certain embodiments can be of murine, primate, or human origin. If the fusion protein is intended for human use, a chimeric form of immunoglobulin may be used wherein the constant regions of the immunoglobulin are from a human.

The purity of the fusion protein can be determined by any of a variety of well-known analytical methods including gel electrophoresis, high pressure liquid chromatography, and the like. For example, the fusion proteins expressed as described in the Examples were shown to be intact and properly assembled as demonstrated by reducing and non-reducing SDS-PAGE.

D. Fragments, Variants, and Derivatives Thereof

The skilled artisan will readily appreciate that the embodiments are not limited to the sequences depicted herein, but also includes variants of ELA. Such variants are well known in the art. They may contain deletions, substitutions or additions of one or more amino acids in the above depicted amino acid sequences while maintaining the biological activity of naturally occurring ELA.

A peptide fragment, or variant, or derivative may differ from a naturally occurring peptide in one or more substitutions, deletions, additions and/or insertions. Such fragments or variants may be naturally occurring or may be synthetically generated, for example, by modifying one or more of the above peptide sequences used in the methods of certain embodiments and evaluating their effects using any of a number of techniques well known in the art.

As used herein, a peptide fragment or variant has amino acid sequences that are at least about 70-75%, typically at least about 80-85%, and most typically at least about 90-95%, 97%, 98% or 99% or more homologous with the ELA peptides. In certain embodiments, a fragment or variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of certain embodiments and still obtain a functional molecule that encodes a variant or derivative polypeptide with desirable characteristics, e.g., with an ability to modulate, induce and/or maintain pluripotency as described herein.

In a ELA peptide or fusion protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). One of skill in the art could determine which amino acid residues can be substituted, inserted, or deleted without abolishing biological activity. Assistance can be found using computer programs well known in the art, such as DNASTAR™ software. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

Fragments, or variants, or derivatives of the peptides of certain embodiments include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and mutants. Truncations or deletions of regions which change functional activity of the proteins are also variants.

Furthermore, variants, analogs or derivatives of the Fc portion may be constructed by, for example, making various substitutions of residues or sequences. Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertional variants with additional residues at either or both termini can include for example, fusion proteins and proteins including amino acid tags or labels. For example, the Fc molecule may optionally contain an N-terminal Met, especially when the molecule is expressed as a recombinant protein in a bacterial cell such as *E. coli*.

In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence.

In Fc substitution variants, one or more amino acid residues of an Fc polypeptide are removed and replaced with alternative residues. In one aspect, the substitutions are conservative in nature, however, certain embodiments embrace substitutions that ore also non-conservative.

For example, cysteine residues can be deleted or replaced with other amino acids to prevent formation of some or all disulfide crosslinks of the Fc sequences. One may remove each of these cysteine residues or substitute one or more such cysteine residues with other amino acids, such as Ala or Ser. As another example, modifications may also be made to introduce amino acid substitutions to (1) ablate the Fc receptor binding site; (2) ablate the complement (Clq) binding site; and/or to (3) ablate the antibody dependent cell-mediated cytotoxicity (ADCC) site. Such sites are known in the art, and any known substitutions are within the scope of Fc as used herein. For example, see Molecular Immunology, Vol. 29, No. 5, 633-639 (1992) with regards to ADCC sites in IgG1.

Likewise, one or more tyrosine residues can be replaced by phenylalanine residues as well. In addition, other variant amino acid insertions, deletions (e.g., from 1-25 amino acids) and/or substitutions are also contemplated and are within the scope of the present embodiments. Conservative amino acid substitutions will generally be preferred. Furthermore, alterations may be in the form of altered amino acids, such as peptidomimetics or D-amino acids.

E. Vectors

Polynucleotides of certain embodiments may be obtained, for example, by solid-state peptide synthesis or using recombinant production. For recombinant production one or more polynucleotides encoding the fusion protein, e.g., as described above, is isolated and inserted into one or more vectors for further cloning and/or expression in a host cell. This polynucleotide may be isolated and sequenced using conventional procedures. All the DNA fragments were assembled by DNA ligation and infusion cloning into pEntra vector.

Many vectors are known in the art. Vector components may include one or more of the following: a signal sequence, an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

An "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto.

Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. Nos. 6,022,952 and 6,335,178; Uemura et al., Protein expression vector and utilization thereof, U.S. Pat. No. 7,029,909; Ruben et al., 27 human secreted proteins, US 2003/0104400 A1), the contents of which are hereby incorporated by reference.

A "secreted" protein refers to those proteins capable of being directed to the ER, secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In one embodiment, a vector, preferably an expression vector, comprising one or more of the polynucleotides encoding the fusion proteins of certain embodiments is provided. In other embodiments, the vector is introduced into mammalian cells, e.g., HEK293 cells to produce the fusion protein in supernatant for purification by Protein A affinity chromatography. The resulting fusion protein (i.e., Fc-ELA-32 or Fc-ELA-21) was used for treatment.

Methods are well known to one of skill in the art and can be used to construct lentiviral expression vectors containing the coding sequence with appropriate transcriptional and translational control signals. In certain embodiments, and as described in Example 1, lentiviruses are produced in HEK293T cells with cotransfection of packaging vectors, and used to infect HEK293 cells to establish a Fc-ELA-32 or Fc-Ela-21 cell lines that permanently secrete the fusion protein into culture medium. A lentiviral expression vector containing the cDNA cassette encoding the human tPA-ss-Fc-hinge-Elabela was made by Gateway cloning of the pEntra vector (Invitirogen, Carlsbad, Calif.) with a fragment of CMV promoter-ccdB was cloned into the universal lentiviral vector pSMPUW-CMV (Cell Biolabs, San Diego, Calif.)-IRES (Internal Ribosome Entry Site)-EGFP. Lentiviruses containing the cassette sequence were made in HEK293T cells by transfection and were used to make HEK293 cells stably producing the recombinant protein in cell culture medium, which was purified into homogeneity by affinity purification of Protein A. All lentiviral vector plasmids were amplified in STBL3 bacteria.

These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989).

Typically, the vectors are derived from virus, plasmid, prokaryotic or eukaryotic chromosomal elements, or some combination thereof, and may optionally include at least one origin of replication, at least one site for insertion of heterologous nucleic acid, and at least one selectable marker. Embodiments are also contemplated that express the polypeptides using artificial chromosomes, e.g., bacterial artificial chromosomes (BACs), yeast artificial chromosomes (YACs), mammalian artificial chromosomes (MACs), and human artificial chromosomes (HACs), e.g., when it is necessary to propagate nucleic acids larger than can readily be accommodated in viral or plasmid vectors. The polypeptides may be expressed using any suitable vector. Typically, the vectors are derived from virus, plasmid, prokaryotic or eukaryotic chromosomal elements, or some combination thereof, and may optionally include at least one origin of replication, at least one site for insertion of heterologous nucleic acid, and at least one selectable marker. Certain embodiments also contemplates expressing the using artificial chromosomes, e.g., bacterial artificial chromosomes (BACs), yeast artificial chromosomes (YACs), mammalian artificial chromosomes (MAs), and human artificial chromosomes (HACs), e.g., when it is necessary to propagate nucleic acids larger than can readily be accommodated in viral or plasmid vectors.

Furthermore, any vector may contain a single coding region, or may comprise two or more coding regions, e.g. a vector of the certain embodiments may encode one or more polypeptides, which are post- or co-translationally separated into the final proteins via proteolytic cleavage. In addition, a vector, polynucleotide, or nucleic acid of embodiments may encode heterologous coding regions, either fused or unfused to a polynucleotide encoding the fusion protein (fragment) of certain embodiments, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed.

Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit a-globin, as well as other sequences capable of controlling gene expression in eukaryotic cells. Additional suitable transcription control regions include tissue-specific promoters and enhancers as well as inducible promoters (e.g. promoters inducible tetracyclines).

It is possible for the expression vector to be part of a plasmid, virus, or it may even be a nucleic acid fragment. The expression vector includes an expression cassette into which the polynucleotide encoding the fusion protein (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors.

F. Host Cells

The term "host cell" means a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. Any of a large number of available and well-known host cells may be used in the practice of these embodiments. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK-293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art.

The polynucleotides encoding the fusion proteins for therapeutic use may be expressed in any appropriate host cell, preferably a mammalian cell. The host cell can be prokaryotic (bacteria) or eukaryotic (e.g., yeast, insect, plant and animal cells). A host cell strain may be chosen for its ability to carry out desired post-translational modifications of the expressed protein. Such post-translational modifications of the polypeptide include, but are not limited to, acetylation, carboxylation, glycosylation, phosphorylation, hydroxylation, sulfation, lipidation, and acylation.

Exemplary mammalian host cells are COS1 and COS7 cells, NSO cells, Chinese hamster ovary (CHO) cells, NIH 3T3 cells, HEK293 cells, HEPG2 cells, HeLa cells, L cells, MDCK, W138, murine ES cell lines (e.g., from strains 129/SV, C57/BL6, DBA-1, 129/SVJ), K562, Jurkat cells, BW5147 and any other commercially available human cell lines. Other useful mammalian cell lines are well known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA).

In a further embodiment, a host cell comprising one or more polynucleotides is provided. In certain embodiments, a host cell comprising one or more vectors is provided. The polynucleotides and vectors may incorporate any of the features, singly or in combination, described herein in relation to polynucleotides and vectors, respectively. In one such embodiment, a host cell comprises (e.g. has been transformed or transfected with) a vector comprising a polynucleotide that encodes (part of) a fusion protein of certain embodiments. As used herein, the term "host cell" refers to any kind of cellular system which can be engineered to generate the fusion proteins of certain embodiments or fragments thereof. Host cells suitable for replicating and for supporting expression of fusion proteins are well known in the art.

Such cells may be transfected or transduced as appropriate with the particular expression vector and large quantities of vector containing cells can be grown for seeding large scale fermenters or cultured in suspension to obtain sufficient quantities of the fusion protein for clinical applications. Suitable host cells include mammalian cells, including preferred cells such as HEK 293 cells. For example, useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Rep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr– CHO cells (Urlaub et al., Proc Natl Acad Sci USA 77, 4216 (1980)); and myeloma cell lines such as YO, NSO, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003).

Host cells are transformed or transfected with the above-described nucleic acids or vectors for production immunoglobulins and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of immunoglobulins.

The host cells used to produce the immunoglobulins of other embodiments may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin.™. drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the immunoglobulin can be produced intracellularly, in the periplasmic space, or directly secreted into the medium. If the immunoglobulin is produced intracellularly, as a first step, the particulate debris, either host cells or lysed fragments, is removed, for example, by centrifugation or ultrafiltration.

G. Pharmaceutical Compositions, Formulations, and Routes of Administration

In a further aspect, certain embodiments provide pharmaceutical compositions comprising an ELA-21 peptide or any of the fusion proteins described herein, e.g., for use in any of the therapeutic methods used for treatment of cardiac conditions. In one embodiment, a pharmaceutical composition comprises an ELA-21 peptide provided herein and a pharmaceutically acceptable carrier. In another embodiment, a pharmaceutical composition comprises the ELA-32 peptide provided herein and at least one additional therapeutic agent, e.g. as described below. ELA-expressing cardiomyocytes or other types of cells for cell transplant therapy. Viral vector expressing ELA fusion proteins may be used for gene therapy or cell therapy of a cardiovascular condition.

In other embodiments, a pharmaceutical composition comprises any of the fusion proteins provided herein and a pharmaceutically acceptable carrier. In another embodiment, a pharmaceutical composition comprises any of the fusion proteins provided herein and at least one additional therapeutic agent, e.g. as described below.

Further provided is a method of producing a fusion protein of certain embodiments in a form suitable for administration in vivo, the method comprising (a) obtaining a fusion protein according to various embodiments, and (b) formulating the fusion protein with at least one pharmaceutically acceptable carrier, whereby a preparation of fusion protein is formulated for administration in vivo.

Pharmaceutical compositions of embodiments comprise a therapeutically effective amount of one or more fusion protein dissolved or dispersed in a pharmaceutically acceptable carrier. The preparation of a pharmaceutical composition that contains at least one fusion protein and optionally an additional active ingredient will be known to those of skill in the art in light of the present disclosure, as exemplified by Remington's Pharmaceutical Sciences, 18th Ed. Mack Printing Company, 1990. For human administration, it will be understood that preparations should meet sterility, pyrogenicity, general safety and purity standards as required by FDA Office of Biological Standards or corresponding authorities in other countries. Preferred compositions are lyophilized formulations or aqueous solutions.

As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it needs to be sterile for such routes of administration as injection. Fusion proteins of certain embodiments (and any additional therapeutic agent) can be administered by any method or any combination of methods as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the fusion proteins of certain embodiments. Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Parenteral compositions include those designed for administration by injection, e.g. subcutaneous, intradermal, intra-lesional, intravenous, intra-arterial, intramuscular, intrathecal or intraperitoneal injection. For injection, the fusion proteins may be formulated in aqueous solutions, preferably in physiologically compatible buffers such as Hanks'solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins in the required amount in the appropriate solvent with various other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi.

Pharmaceutical compositions comprising the ELA-21 peptide or fusion proteins (e.g., Fc-ELA-32, Fc-ELA-21, Elabela-Apelin) may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The ELA-21 peptide or fusion proteins (e.g., Fc-ELA-32, Fc-ELA-21, Elabela-Apelin) may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The pharmaceutical preparation of certain embodiments is a liquid composition, e.g. an aqueous solution. For injection purposes, the use of pure water as solvent is preferred. Other solvents which are suitable and conventional for pharmaceutical preparations can, however, also be employed. In a preferred embodiment, the pharmaceutical compositions are isotonic solutions.

Further, there is no need for reconstitution at any stage of the preparation of the liquid solution formulation of these embodiments. The solution is a ready-to-use formulation.

The pharmaceutical composition of certain embodiments has a pH in the range of 4.5 to 5.5. In a preferred embodiment, the pH value is from a range of 4.7 to 5.3, more preferably, between 4.8 to 5.2, and most preferably between 4.9 and 5.1.

If an adjustment is required in order to achieve the desired pH range, the pH value is adjusted by means of suitable solutions; with acidic solutions in case a reduction of the pH value is indicated and with alkaline solutions in case an increase of the pH value is indicated. Suitable acidic solutions are e.g. hydrochloric acid, phosphoric acid, citric acid and sodium or potassium hydrogen phosphate. Suitable alkaline solutions are alkali and alkali earth hydroxides, alkali carbonates, alkali acetates, alkali citrates and dialkali hydrogen phosphates, e.g. sodium hydroxide, sodium acetate, sodium carbonate, sodium citrate, disodium or dipotassium hydrogen phosphate or ammonia.

The delivery of a therapeutic immunoglobulin to appropriate cells can occur via gene therapy ex vivo, in situ, or in vivo by use of any suitable approach known in the art. For example, for in vivo therapy, a nucleic acid encoding the desired immunoglobulin or antibody, either alone or in conjunction with a vector, liposome, or precipitate may be injected directly into the subject, and in some embodiments, may be injected at the site where the expression of the immunoglobulin compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

A variety of techniques are available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, chemical treatments, DEAE-dextran, and calcium phosphate precipitation. Other in vivo nucleic acid transfer techniques include transfection with viral vectors (such as adenovirus, Herpes simplex I virus, adeno-associated virus or retrovirus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL))(Felgner et al, (1987) Proc. Natl. Acad. Sci. USA 84, 7413-7417; Malone et al. (1989) Proc. Natl Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES)(J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP)(Boehringer Mannheim), polyethyleneimine (PEI), dioleoyl esters, ChoTB, ChoSC, DOSC)(Leventis et al. (1990) Biochim. Inter. 22, 235-241); 3 beta [N—(N', N'-dimethylaminoethane)-carbamoyl] cholesterol (DC-Chol), dioleoylphosphatidyl ethanolamine (DOPE)/3beta [N—(N', N'-dimethylaminoethane)-carbamoyl] cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1, 1, 3, 3-tetramethylbutyl) cre-soxy] ethoxy] ethyl] dimethylbenzylammonium hydroxide (DEBDA hydroxide) with excess phosphatidylcholine/cholesterol (Ballas et al., (1988) Biochim. Biophys. Acta 939, 8-18), cetyltrimethyl-ammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP (SEQ ID NO:16), linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

In some situations it may be desirable to deliver the nucleic acid with an agent that directs the nucleic acid-containing vector to target cells. Such "targeting" molecules include antigen binding proteins specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antigen binding proteins for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455460 (1992).

H. Dosage and Administration

Any of the ELA peptides and fusion proteins provided herein may be used in therapeutic methods described herein. For use in the therapeutic methods described herein, ELA peptides and fusion proteins of certain embodiments would be formulated, dosed, and administered in a fashion consistent with good medical practice. Factors for consideration in this context include the particular disorder being treated, the particular subject being treated, the clinical condition of the subject, the cause of the disease or condition, the site of delivery of the agent, the method of administration, the scheduling of administration, and other factors known to medical practitioners or those of skill in the art.

In certain embodiments the method further comprises administering to the individual a therapeutically effective amount of at least one additional therapeutic agent, e.g. a statin the cardiac condition or cardiac disease to be treated is hyperlipidemia. A "subject" or "individual" according to any of the above embodiments is a mammal, preferably a human.

For the treatment of a cardiac disease or cardiac condition, the appropriate dosage of a fusion protein of the embodiment (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The ELA peptides (e.g., ELA-32, ELA-21, Apelin-13) or fusion proteins (e.g., Fc-ELA-32, Fc-ELA-21, Elabela-Apelin) are suitably administered to the patient at one time or over a series of treatments subcutaneously, intravenously, intramuscularly, locally or via airway or under tongue. Depending on the type and severity of the disease, about 1 mg to 100 mg of fusion protein or peptide can be an initial dosage for administration to the patient, whether, for example, by one or more separate administrations, or by continuous infusion. One typical daily dosage might range from about 50 mg or more, depending on the factors mentioned above. For repeated administrations over several days or longer, depending on the condition, the treatment would generally be sustained until a desired suppression of disease symptoms occurs.

One preferred dosage would be in the range from about 1 mg. In other non-limiting examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein.

In non-limiting examples of a derivable range from the numbers listed herein, a range of about 5 mg/kg body weight to about 100 mg/kg body weight, about 5 µg/kg body weight to about 500 mg/kg body weight, can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The ELA peptides (e.g., ELA-32, ELA-21, Apelin-13) and fusion proteins (e.g., Fc-ELA-32, Fc-ELA-21, Elabela-Apelin) of certain embodiments will generally be used in an amount effective to achieve the intended purpose. For use to treat or prevent a disease condition, the ELA peptides and fusion proteins of these embodiments, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the IC.sub.50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

The inventive compound may be administered by an initial bolus followed by a continuous infusion to maintain therapeutic circulating levels of drug product. As another example, the inventive compound may be administered as a one-time dose. Those of ordinary skill in the art will readily optimize effective dosages and administration regimens as determined by good medical practice and the clinical condition of the individual patient.

Sustained-release preparations may be prepared. Suitable examples of sustained-release preparations include semipermeable matrices of solid hydrophobic polymers containing the immunoglobulin, which matrices are in the form of shaped articles, e.g., films, or microcapsule. Examples of sustained-release matrices include polyesters, hydrogels (for example, poly (2-hydroxyethyl-methacrylate), or poly (vinyl alcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot.™. (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of other embodiments may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of certain embodiments.

The dosage may vary within this range depending upon a variety of factors, e.g., the dosage form employed, the route of administration utilized, the condition of the subject, and the like. The exact formulation, route of administration and dosage can be chosen by the individual physician in view of the patient's condition. Dosage amount and interval may be adjusted individually to provide plasma levels of the fusion proteins which are sufficient to maintain therapeutic effect. Usual patient dosages for administration by injection range from about 0.1 to 50 mg/kg/day, typically from about 0.5 to 10 mg/kg/day. Therapeutically effective plasma levels may be achieved by administering multiple doses each day. Levels in plasma may be measured, for example, by HPLC.

The attending physician for patients treated with fusion proteins of certain embodiments would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

I. Therapeutic Agents

The ELA peptides (e.g., ELA-32, ELA-21, Apelin-13) and fusion proteins (e.g., Fc-ELA-32, Fc-ELA-21, Elabela-Apelin) described herein may be administered in combination with one or more other agents or "therapeutic agents" for use in treatment of cardiac diseases, cardiac conditions, diabetes, or at risk factors. An ELA peptide (e.g., ELA-32 or ELA-21) or fusion protein (e.g., Fc-ELA-32 or Fc-ELA-21) may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is a medication selected from the group consisting of: an ACE inhibitor, an aldosterone antagonist, an angiotensin receptor blocker, a beta-blocker, a calcium channel blocker, a cholesterol lowering drug, a digoxin, a diuretic, a glucose lowering drug, potassium or magnesium, a vasopressin antagonist, and warfarin.

There are a variety of drugs prescribed for patients with heart disease. It's important for both patients living with heart disease and those who care for them to understand the prescribed medication, to follow the directions of usage, and to be able to recognize the possible side effects associated with the medicine. The drugs most commonly prescribed for heart disease include:

ACE Inhibitors: Angiotensin converting enzyme (ACE) inhibitors are heart medications that widen or dilate your blood vessels to improve the amount of blood your heart pumps and lower blood pressure making it easier for the heart to pump blood. They also block some of the harmful actions of the endocrine system that may occur with heart failure. ACE inhibitors also increase blood flow, which helps to decrease the amount of work your heart has to do.

Examples of ACE inhibitors include but are not limited to: Accupril® (quinapril), Aceon® (perindopril), Altace® (ramipril), Capoten® (captopril), Lotensin® (benazepril), Mavik® (trandolapril), Monopril® (fosinopril), Prinivil®, Zestril® (lisinopril), Univasc® (moexipril), and Vasotec® (enalapril).

Aldosterone Inhibitor: Examples include but are not limited to: Inspra®, (eplerenone) and Aldactone® (spironolactone). They are potassium-sparing diuretics. They can be prescribed to reduce the swelling and water build-up caused by heart failure. Diuretics cause the kidneys to send unneeded water and salt from the tissues and blood into the urine. They may improve heart failure symptoms that are still present despite use of other treatments. These drugs protect the heart by blocking a chemical (aldosterone) in the body that causes salt and fluid build-up. This medication is used to treat patients with certain types of severe heart failure.

Angiotensin II Receptor Blocker (ARBs): ARBs inhibit a substance that causes blood vessels to narrow (constrict). As a result, blood vessels relax and widen (dilate), making it easier for blood to flow through the vessels, which reduces blood pressure. These medicines also increase the release of water and salt (sodium) to the urine, which in turn lowers blood pressure as well. Preventing the blood vessels from constricting helps improve blood flow, which reduces the backup of blood in the heart and lungs. It also decreases the pressure that the left ventricle of the heart must pump against. Examples include but are not limited to: Atacand® (candesartan), Teveten® (eprosartan), Avapro® (irbesartan), Cozaar® (losartan), Benicar® (olmesartan), Micardis® (telmisartan), and Diovan® (valsartan). ARBs combined with a diuretic include Avalide®, (irebesartan and hydrochlorothiazide) and Hyzaar® (losartan and hydrochlorothiazide).

Beta-Blockers: Beta blockers, also known as beta-adrenergic blocking agents, are medications that reduce blood pressure. Beta blockers work by blocking the effects of the hormone epinephrine, also known as adrenaline. When you take beta blockers, the heart beats more slowly and with less force, thereby reducing blood pressure. They improve the heart's ability to perform. They also decrease the production of harmful substances produced by the body in response to heart failure. Examples of beta-blockers include but are not limited to: Sectral® (acebutolol), Zebeta® (bisoprolol), Brevibloc® (esmolol), Inderal® (propranolol), Tenormin® (atenolol), Normodyne®, Trandate® (labetalol), Coreg® (carvedilol), Lopressor®, and Toprol-XL® (metoprolol).

Calcium Channel Blockers: Calcium channel blockers are prescribed to treat angina (chest pain) and high blood pressure. Calcium channel blockers affect the movement of calcium in the cells of the heart and blood vessels. As a result, the drugs relax blood vessels and increase the supply of blood and oxygen to the heart, while reducing its workload. Calcium channel blockers are only used to treat heart failure caused by high blood pressure when other medications to lower blood pressure are ineffective. Certain calcium channel blockers are used for certain types of heart failure. Examples include but are not limited to: Norvasc (amlodipine), Plendil® (felodipine), Cardizem®, Cardizem CD®, Cardizem SR®, Dilacor XR®, Diltia XT®, Tiazac® (diltiazem), Calan®, Calan SR®, Covera-HS®, Isoptin®, Isoptin SR®, Verelan®, Verelan PM® (verapamil), Adalat®, Adalat CC®, Procardia®, Procardia XL® (nifedipine), Cardene®, Cardene SR® (nicardipine), Sular® (nisoldipine), and Vascor® (bepridil). Caduet is a combination of a statin cholesterol drug and amlodipine (above).

Cholesterol-Lowering Drugs: Cholesterol helps your body build new cells, insulate nerves, and produce hormones. But inflammation may lead to cholesterol build-up in the walls of arteries, increasing the risk of heart attack and stroke. Some people have a genetic predisposition to high cholesterol levels. These people may need drug therapy such as statins in addition to a healthier diet to reduce their risk of atherosclerosis. Examples of statins include: atorvastatin (Lipitor®), fluvastatin (Lescol®), lovastatin (Altoprev®, Mevacor®), pravastatin (Pravachol®), rosuvastatin Calcium (Crestor®), and simvastatin (Zocor®). Some statin medications include an adjunct drug to help lower triglycerides or boost HDL cholesterol. These include: atorvastatin with amlodipine (Caduet®), lovastatin with niacin (Advicor®), and simvastatin with ezetimibe (Vytorin®).

Bile acid sequestrants: These are resins that help the body dispose of LDL cholesterol. The body uses cholesterol to create bile, which is used in the digestive process. As the name suggests, this class of drugs binds to bile so that it can't be used during digestion. The body responds by making even more bile, which requires more cholesterol. The more bile it makes, the more cholesterol the body uses, thereby lowering the amount of cholesterol in your bloodstream. People with liver or gallbladder problems should avoid using these medications. Examples of bile-acid-binding resins include: cholestyramine (Locholest®, Locholest Light®, Prevalite®, Questran®, and Questran Light®), colesevelam HCl (WelChol®), and colestipol (Colestid®).

Fibrates: Used alone or in combination with other drugs, fibrates work by lowering triglycerides and, in some cases, by raising "good" HDL cholesterol. Examples of fibrates include: clofibrate (Atromid-S®), and gemfibrozil (Lopid®), fenofibrate (Antara®, Lofibra®, Tricor®, and Triglide®).

Omega-3 Fatty Acids: A prescription-strength fish oil (omega-3 fatty acid) called Lovaza® is FDA-approved for the treatment of very high blood triglycerides (above 500 ml/dL). Omega-3 fatty acids are also available as supplements, but in lower doses. Prescription-strength niacin, also known as vitamin B3, helps improve cholesterol by boosting HDL and lowering LDL and triglycerides. When used in combination with statins, niacin could raise HDL levels by 50 percent or more. Examples of prescription-strength niacin include: Niacor®, Niaspan®, and Slo-Niacin®.

Digoxin: Digoxin helps an injured or weakened heart to work more efficiently and to send blood through the body. It strengthens the force of the heart muscle's contractions and may improve blood circulation. It may also be prescribed if the patient has atrial fibrillation (irregular heart beat rhythm) to help slow down the heart rate. Examples include but are not limited to: Lanoxin®, Lanoxincaps®, and Crystodigin.®

Diuretics: Diuretics, commonly known as "water pills," cause the kidneys to get rid of unneeded water and salt from the tissues and bloodstream into the urine. Getting rid of excess fluid makes it easier for your heart to pump. Diuretics are used to treat high blood pressure and reduce the swelling and water build-up caused by various medical problems, including heart failure. They also helps make breathing easier. Examples of diuretics include but are not limited to Aqua-Ban®, Osmitrol®, Diamox® and MZM®.

Glucose-lowering Drugs: Glucose-lowering drugs work by stimulating the pancreas to make insulin to bring down elevated blood glucose levels. Examples include but are not limited to the following:
(i) Sulfonylureas (Gliclazide, Glimepiride, Glyburide (also known as glibenclamide) which work to stimulate the pancreas to make insulin;

(ii) Metformin (biguanide) which works primarily by reducing how much glucose the liver releases;
(iii) Glinides (Repaglinide or GlucoNorm® and Nateglinide (Starlix®), which work by stimulating the pancreas to make insulin;
(iv) Alpha-glucosidase Inhibitors (GlucoBay®) which work by slowing down absorption of glucose from the intestine;
(v) Thiazolidinediones (TZDs) (pioglitazone and rosiglitazone) which work by increasing the amount of glucose taken up by muscle and fat cells;
(vi) DPP-4 Inhibitors (Saxagliptin (Onglyza®), Sitaliptin (Januvia®), and Vildagliptin®) which work by stimulating the pancreas to make insulin and reducing how much glucose the liver releases; and (vii) GLP-1 Analogues Liraglutide (Victoza®) and Exenatide (Byetta®) and pramlinitide (Symlin®)) which work by stimulating the pancreas to make insulin, reducing how much glucose the liver makes, slowing down how quickly the stomach empties food into the intestine, and by reducing appetite.

Inotropic Therapy: Inotropic therapy is used to stimulate an injured or weakened heart to pump harder to send blood through the body. It helps the force of the heart muscle's contractions and relaxes constricted blood vessels so blood can flow more smoothly. Inotropic therapy may also speed up the heart's rhythm. Inotropic therapy is used in end-stage heart failure to help relieve and control heart failure symptoms. These medications are only used when others no longer control heart failure symptoms.

Potassium or Magnesium: Potassium and magnesium are minerals that can be lost because of increased urination when taking diuretics. Low levels in the body can be associated with abnormal heart rhythms. Some patients take them as supplements as directed by their doctor.

Vasodilators: Vasodilators are used to treat heart failure and control high blood pressure by relaxing the blood vessels so blood can flow more easily through the body. Vasodilators are prescribed for patients who cannot take ACE inhibitors. Examples include but are not limited to amyl nitrite (Vapotole®), erythrityl tetranitrate (Cardilate®), isosorbide dinitrate (Iso-Bid®, Isordil®, Sorbide®, Sorbitrate®), mannitol hexanitrate (Nitranitol®), and nitroglycerin (Nitro-Bid®).

Warfarin: Warfarin is an anticoagulant medication, which helps prevent clots from forming in the blood. A person is prescribed warfarin because the body is making blood clots or the person has a medical condition known to promote unwanted blood clots. Blood clots can move to other parts of the body and cause serious medical problems. Warfarin will not dissolve a blood clot; over time, however, the blood clot may dissolve on its own. Warfarin may also prevent other clots from forming.

These therapeutic agents are suitably present in combination in amounts that are effective for the purpose intended. The effective amount of these other agents depends on the amount of fusion protein used, the type of disease or condition, or treatment, and other factors discussed above. The fusion proteins are generally used in the same dosages and with administration routes as described herein, or about from 1 to 99% of the dosages described herein, or in any dosage and by any route that is empirically/clinically determined to be appropriate. Dosing is dependent on the severity and responsiveness of the condition to be treated, with course of treatment lasting from several days to several months. Persons of ordinary skill can easily determine optimum dosages, dosing methodologies, and repetition rates. Therapeutically or prophylactically effective amounts (dosages) may vary depending on the relative potency of individual compositions, and can generally be calculated routinely based on molecular weight and EC50s in in vitro and/or animal studies.

Such combination therapies noted above encompass combined administration (where two or more therapeutic agents are included in the same or separate compositions), and separate administration, in which case, administration of the fusion protein of certain embodiments can occur prior to, simultaneously, and/or following, administration of the additional therapeutic agent and/or adjuvant.

J. Kits

In another aspect of the embodiment, an article of manufacture (e.g., a kit) containing materials useful for the treatment of the cardiac diseases or cardiac conditions described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle).

The label or package insert indicates that the composition is used for treating the condition of choice. The article of manufacture may comprise (a) a first container with a composition contained therein, wherein the composition comprises an ELA-32 fusion protein or ELA-21 fusion protein; and (b) a second container with a composition contained therein, wherein the composition comprises a further therapeutic agent.

Kits in certain embodiments may further comprise a package insert indicating that the compositions can be used to treat a particular condition. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

5. Summary of Experimental Results

The following is a summary of results of experiments described in the Examples of this application:
- ELA-32 activates APJ signaling pathways, induces angiogenesis of human HUVECs and relaxes mouse aortic blood vessels thus establishing that ELA-APJ signaling pathways are conserved and functional in vertebrates.
- ELA-32 is expressed only in adult kidney tissue and embryonic and induced adult pluripotent stem cells.
- ELA-32 induces APJ internalization.
- ELA-32 inhibits cAMP production, induces phosphorylation of ERK ½, and caused a rapid calcium mobilization in a dose-dependent manner proving ELA's effects on intracellular signaling were APJ-dependent.
- ELA-32 targets blood vessels and exerts an angiogenic effect directly through activation of APJ.
- ELA-32 relaxes blood vessels in a concentration-dependent manner with maximum relaxation of 73.7% in endothelium-intact vessels. Nitrous oxide production is not required for ELA-mediated relaxation.

ELA-32 significantly mitigated the degree of heart dysfunction and improves cardiac performance in a MI-induced heart failure model.

ELA-32 treatment increases diuresis.

ELA-32 treatment protects against MI-induced cardiomyocyte apoptosis.

ELA-32 induces endothelium-dependent and endothelium-independent relaxation in mouse aorta (in vivo).

ELA-32 significantly suppressed Ang II-induced aldosterone synthase gene expression resulting in a reduction of aldosterone levels and improvement of diuresis in mice.

ELA-32 treatment protects against MI-induced cardiomyocyte apoptosis.

Fc-ELA-32 fusion protein mitigates MI-induced heart damage by reducing LFEDP and heart fibrosis.

Fc-Ela-32 and Fc-apelin-13 have a half-life in serum ranging between 24 and 50 hours.

Fc-ELA-32 fusion protein mitigates MI-induced heart damage by reducing LFEDP and heart fibrosis.

Fc-ELA-32 fusion protein reduces heart fibrosis in an infarcted heart.

Fc-ELA-32 increases cardiomyocyte proliferation and reduces apoptosis.

In functional studies, Fc-Apelin-13 lowered glucose levels and improves insulin sensitivity in obese mice.

6. EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Materials and Methods

Chemicals

The mature form of the 54 amino acid ELA peptide, a 32-amino acid, QRPVNLTMRRKLRKHNCLQRRCMPLHSRVPFP (SEQ ID NO: 1) and apelin-13, QRPRLSHKGPMPF (SEQ ID NO: 3), were purchased by GenScript (Piscataway, N.J.), at more than 98% purity. Other chemicals were from Sigma (St. Louis, Mo.) unless otherwise stated.

Cell Culture

Chinese hamster ovary (CHO) cells were obtained from ATCC (Manassas, Va.) and grown in Ham's F12 medium supplemented with 10% fetal bovine serum (FBS), 100 µg/mL streptomycin and 100 U/mL penicillin. Human umbilical vein endothelial cells (HUVECs) were purchased from Lonza (Walkersville, Md.) and cultured in basal medium supplemented with 0.2% endothelial cell growth supplement (EnGS), 5 ng/mL recombinant human EGF, 50 µg/mL ascorbic acid, 10 mM L-Glutamine, 1 µg/mL hydrocortisone hemisuccinate, 0.75 U/mL heparin sulfate and 2% FBS. HUVECs between passage 3 and 5 were used for all experiments.

Plasmid Construction

The human APJ cDNA was amplified from human fat tissue by PCR with NotI/SalI restriction sites at the 3'-end and cloned into a Gateway pENTRa vector (Invitrogen, Carlsbad, Calif.). EGFP-APJ fusion construct was made by assembling PCR amplified-APJ and EGFP fragments into pENTRa by Infusion cloning (Clontech, Mountain View, Calif.). To make lentiviral destination vector pSMPUW-CMV-DEST, a fragment of CMV promoter-ccdB was cloned into the universal lentiviral vector pSMPUW (Cell BioLabs, San Diego, Calif.). Standard Gateway LR cloning protocol was used to generate pLenti-APJ or EGFP-tagged APJ by using LR Clonase II according to the manufacturer's instructions (Invitrogen). All lentiviral vector plasmids were amplified in STBL3 bacteria (Invitrogen). The cDNA inserts of all constructs were confirmed by restriction enzyme digestion and DNA sequence analysis.

Production of Lentivirus

HEK293T cells were cultured in Dulbecco's modified Eagle's medium (DMEM) containing 10% FBS, 100 µg/mL streptomycin and 100U/mL penicillin. Cells were allowed to reach 90% confluence at which point they were transfected in the presence of DMEM with 1.2 ug of transfer vector, 1.2 ug of pCD/NL-BH*DDD (Addgene plasmid 17531) and 0.2 µg of pVSVG (Cell Biolabs) for each well of a 6-well plate using Lipo0293 (Signal). Lipo0293/DNA complex-containing medium was removed and replaced with fresh medium 16 hours post transfection. The supernatant containing the viral particles was collected at 48 hours and 72 hours following initial transfection, combined and aliquoted for storage at $-80°$ C. Lentiviruses used for all experiments had a minimum titer of $5\times10^5$ IFU/ml.

Stable CHO Cell Lines Expressing APJ or EGFP-Tagged APJ

CHO cells at about 100% confluence were plated onto 6-well plates and infected by exposure to lentiviral supernatant and polybrene (0.8 µg/mL, Millipore, Billerica, Mass.). The CHO cells were incubated for 16 hours, then viral supernatant was replaced with CHO growth medium for 8 hours. The viral infection was conducted twice. Twenty four hours after the second infection, the cells were fed with growth medium supplemented with 1 µg/mL puromycin and puromycin-resistant cells were expanded for further studies.

Semi-Quantitative RT-PCR

Total RNA was extracted using TRJzol reagent (Invitrogen) according to the manufacturer's instructions. cDNA was synthesized using AMV Reverse Transcriptase kit (Promega, Madison, Wis.) from 1 µg of total RNA, and used for detection of gene expression. The primer sequences and expected fragment sizes were as follows: APJ 5' forward primer 5'-CTGGTGGTGACCTITGCCCTG-3' (SEQ ID NO: 7) and reverse primer 5'-AAAGCTGGGTCTAGAGTCGACCTAGTCAACCACAAGGGTCTCCT-3' (388 bp) (SEQ ID NO: 8), ELA forward primer 5'-CTGAGGTITGTCACTAGAATGTGAA-3 ' (SEQ ID NO: 9) and reverse primer 5'-TAAGCAATCACGCTGTTGGCATCA-3' (360 bp), (SEQ ID NO: 10)-actin forward primer 5'-AGAAAATCTGGCACCACACC-3 ' (SEQ ID NO: 11) and reverse primer 5'-GGGGTGTTGAAGGTCT CAAA-3' (142 bp) (SEQ ID NO: 12).

cAMP Assay

Intracellular cAMP levels were measured using a time-resolved fluorescence resonance energy transfer (TR-FRET) assay with an HTRF cAMP kit (Cisbio), as described before (10). Briefly, CHO cells expressing APJ were seeded at 20 µl/well with 10,000 cells in white, tissue-culture-treated 384-well plates (Greiner BioOne). After overnight incubation at 37° C. with 5% $CO_2$, various concentrations of synthetic ELA in assay buffer were added, followed by forskolin stimulation solution (final concentration of 10 µM). The assay plate was determined in a TR-FRET mode using the Evision plate reader (PerkinElmer). The amount of cAMP is reversely correlated with the ratio of 665/615 nm.

ERK ½ Phosphorylation Assay

Intracellular pERK½ levels were measured using TR-FRET assay by a HTRF Cellular kit (Cisbio) according to the manufacturer's instructions and reported before (10). Briefly, following overnight incubation of APJ over-expressing or wide type CHO cells, the growth medium was replaced with 100 µl/well Opti-MEM medium (ATCC) and incubated for additional 4 h. The various concentrations of ELA were added to assay plate and incubated 20 min at 37° C. with 5% $CO_2$, then the medium was aspirated and the plates placed on ice for 5 min followed by the addition of cell lysis solution (Triton X 100). The plates were then incubated at room temperature with gently rocking (for mixing) for 15 min. An aliquot of 16 µl/well of cell lysate was transferred to a 384-well Greiner white half-well plate and 2 ul/well of the $d^2$-dye-conjugated anti-ERK ½ antibody added, incubated in the dark for 2 hours, followed by an addition of 2 µl/well of the europium cryptate-conjugated anti-ERK ½ antibody. After overnight incubation at room temperature in the dark, the plates were measured using the EnVision plate reader in TR-FRET mode (excitation~320 nm; emission=615/665).

Intracellular Calcium Assay

Intracellular calcium was measured using the non-wash calcium assay Fluo8 kit (AAT Bioquest) according to the manufacturer's instructions (10). Briefly, CHO cells stably expressing APJ or empty vector were seeded as above and incubated overnight at 37° C. with 5% $CO_2$. Next day, growth media was aspirated and calcium dye added. Following incubation for 30 minutes at 37° C. and 30 minutes at room temperature, ELA at various concentrations in assay buffer was added and assay plates incubated at room temperature for 10 minutes. Then the plates were placed into a fluorescence kinetic plate reader (uCell, Hamamatsu). The basal fluorescence intensity was recorded 10 times at 1 Hz for 10 seconds. The results were normalized to the average basal fluorescence intensity in ratio and the peak response was used for the result calculation.

Western Blot Analysis

CHO cells were homogenized in lysis buffer containing 50 mM Tris-HCl (pH 6.8) and 2% SDS with freshly added protease/phosphatase inhibitor cocktail (Cell Signaling Technology, USA). The protein content was determined using a protein assay kit (Thermo Fisher Scientific, Waltham, Mass.). Each sample with equal amount of proteins was mixed with 5×SDS samples buffer, boiled for 5 min, and separated on 10% sodium dodecyl sulphate-polyacrylamide electrophoresis (SDS-PAGE) before transferring the proteins onto a PVDF membrane. The membranes were then blocked at room temperature for 1 hr with 5% milk in Tris-buffered saline-Tween (TBST), followed by subsequent incubation at 4° C. overnight in TBST containing the different primary antibodies (1:1000 dilution). After washing three times with TBST, the membranes were incubated for 2 hours in TBST containing the horseradish peroxidase-conjugated secondary antibodies (1:2000 dilution), followed by washing again with TBST for 3 times, then underwent detection by the chemiluminescence system. Extracellular signal-regulated kinase (ERK ½, Cat. #9102) and phosphor-ERK ½ (Cat. #9101) were purchased from Cell Signaling Technology (Danvers, Mass.), and HRP-conjugated GAPDH monoclonal antibody (Cat.# HRP-6004) from ProteinTech Corporation (Chicago, Ill.).

Internalization Assay

HEK293 cells stably expressing EGFP-tagged APJ receptor were serum starved for 24 hours, and treated with ELA (500 nM), and analyzed by live fluorescent microscopy at time intervals following the treatment. For washout experiment, the cells were incubated with ELA for 1 hour and then replaced with serum-free basal medium, and images were taken 1 hour and 4 hour after washout. Confocal imaging was performed with a Zeiss LSM510 microscope.

In Vitro Angiogenesis Assay

Tube formation assay for angiogenesis was conducted in 24-well plates were coated with 50 µl of Geltrex (Life Technologies, A14133-02) and left for polymerization by incubation for 1 hour at 37° C. HUVECs (10,000/well, 3-5 passages) in basal medium (Lifeline, LM-0002) containing endothelial cell growth supplement (EnGS, Lifeline, LS-1018) with FGF (50 ng/mL) and/or different concentration of ELA (0.1, 0.5, 1 µM) were then plated on the Geltrex and incubated overnight at 30° C. with 5% $CO_2$. Quantification of tube formation was performed after 10 hours of culture by calculating the number of branching point formed in each well under an inverted phase contrast photomicroscope (Olympus IX5O) as described[37].

Assays of Endothelium-Dependent and -Independent Vasorelaxation

Aortas were isolated from 8-10 weeks male wild-type C57BL/6 mice, cut into 3-mm rings and mounted in organ chambers (PowerLab, AD Instruments, CO, USA) in Kreb's buffer as described previously (11, 12). The contractile response was elicited by vasoconstrictor U46619 (30 nM) to produce contraction. At the plateau of contraction, accumulative ELA or apelin-13 ($10^{-8}$ 10 M to $10^{-5}$ 6 M) were added into the organ bath to induce relaxation. In some preparations, the endothelium was mechanically removed from denuded arteries by gentle rubbing off the intimal surface with a wooden stick. To determine whether nitric oxide participates in relaxation, aorta was pretreated with 1 mM L-ng-nitroarginine methyl ester (L-NAME) for 30 min, then induced to contraction by U46619, followed by ELA as described above. The effectiveness of endothelium removal and NOS inhibition were confirmed later by an inability of acetylcholine to relax the arteries.

Statistical Analysis

Data were expressed as means±the standard error of the mean (SEM). Statistical analyses were performed by using of two-way ANOVA or Student's t-test. $P<0.05$ was considered statistically significant.

Example 2

Tissue Distribution of ELA and APJ in Humans

RT-PCR analyses of ELA and APJ on cDNAs derived from multiple human tissues including the heart, kidney, brain, lung, stomach, pancreas, and fat was conducted with primers specific for ELA or APJ and was conducted to determine ELA tissue distribution in humans, in comparison with APJ. As shown in FIG. 1, APJ is widely distributed and expressed in tissues of heart, brain, kidney, stomach, lung, adipose tissues and pancreas. In contrast, ELA was expressed only in adult kidney tissue and embryonic and induced adult pluripotent stem cells (ESCs and iPSCs).

Example 3

ELA Induction of Human APJ Endocytosis

Figure 2A:
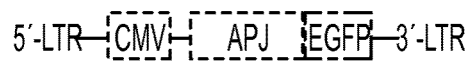
FIG. 2A is a schematic of an APJ-GFP fusion protein.
Figures 2B, 2C, 2D, 2E, 2F, 2G:
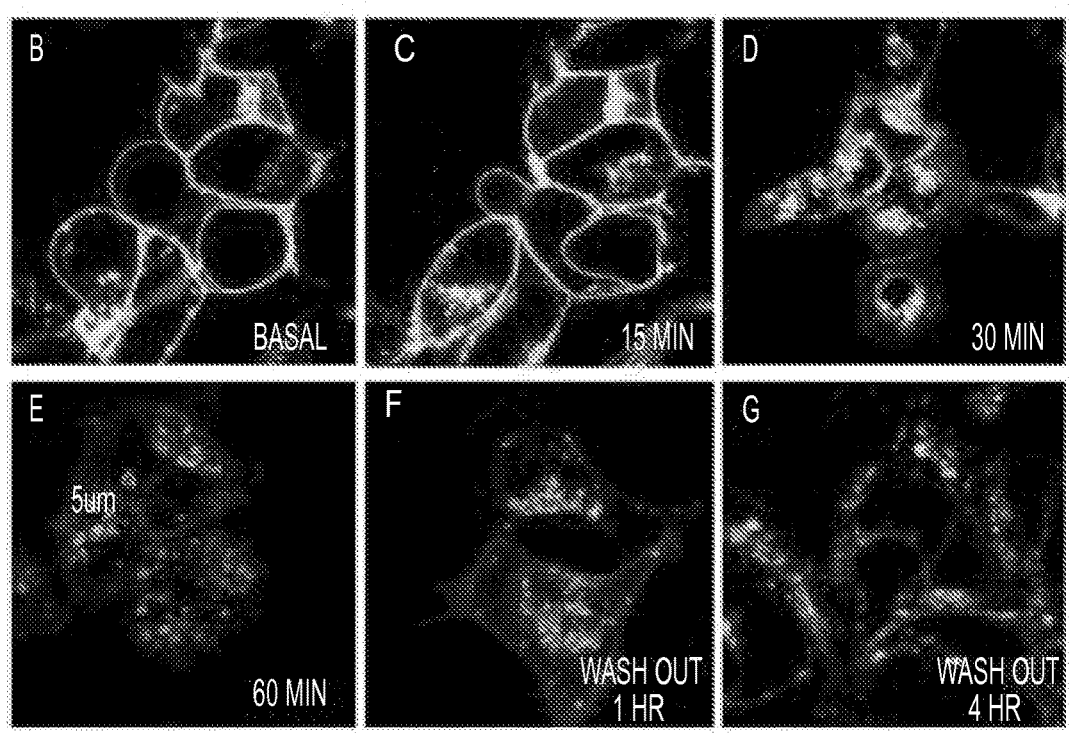
FIG. 2B-2G are photographs of internalization of APJ-EGFP fusion protein stimulated by ELA.

To investigate whether ELA would induce APJ internalization, APJ was over-expressed as a fusion protein with enhanced green fluorescent protein (APJ-GFP, FIG. 2B) through lentiviral infection in HEK293 cells. Its intracellular localization in response to ELA treatment was examined. At the basal level, the fusion protein was localized largely at the cell surface, with some perinuclear expression detected (FIG. 2C). Following ELA treatment, intracellular dot-like vesicles appeared by 15 min (FIG. 2C) and became more apparent by 30 min (FIG. 2D). By 60 min (FIG. 2E), large and hollow intracellular vesicles (3-5 µm in diameter) were clearly visible in the cytoplasm. The fluorescent vesicles remained in the cytoplasm 1 hour (FIG. 2F) and appeared to return to the cell surface 4 hours (FIG. 2G) after the washout in cells previously treated with ELA for 60 minutes.

Example 4

Suppression of cAMP Production, Activation of ERK½ and Calcium Mobilization by ELA Activation of APJ is known to result in a decrease of cAMP production, stimulation of ERK and increase in intercellular calcium mobilization (13). It was investigated whether ELA could activate these signaling pathways. APJ-over-expressing and empty vector control CHO-K 1 cells were used in the studies. APJ expression was confirmed by RT-PCR. For cAMP assays, the CHO-K1 cells were pre-treated with increasing concentrations of ELA and then with adenylate cyclase agonist forskolin to assess the biological activity of ELA to suppress cAMP production. As shown in FIG. 3A, ELA inhibited cAMP production in a dose-dependent manner with an $EC_{50}$ of 11.1 nM. In addition, it was determined in the same cell system that ELA was able to induce the phosphorylation of ERK ½ within 5 minutes of treatment. This effect lasted for 45 minutes as revealed by Western analysis (FIG. 3B, upper panel). It was confirmed quantitatively the effect of ELA on ERK ½ phosphorylation by time-resolved fluorescence resonance energy transfer (TR-FRET) assay. FIG. 3B shows that ELA stimulated ERK ½ in a dose-dependent manner at the tested concentration range from $10^{-10}$ to $10^{-6}$ M, with an EC50 of 14.3 nM. Finally, the ELA effect on intracellular calcium mobilization was investigated. ELA treatment caused a rapid calcium mobilization, peaked at 40 milliseconds in a dose-dependent manner (FIG. 3C, upper panel). The response was dose-dependent up to the concentration of $10^{-5}$M (FIG. 3C, lower panel). Most importantly, no meaningful changes in parallel control experiments were observed in the above assays for cells transduced with empty vector control viruses. Thus, ELA effects on intracellular signaling were APJ-dependent.

Example 5

Angiogenetic Effects of ELA In Vitro

ELA is a secreted hormone and expressed in adult kidney and prostate, and may, therefore, circulate in blood. It is required for normal development of cardiovascular system, suggesting that blood vessel could be a target of ELA action. Vascular tube formation assay is a well-used in vitro study to assess angiogenic factors and conditions in which vascular cells, e.g., human umbilical vascular endothelial cells (HUVECs), can form tube-like structures under proangiogenic conditions in culture wells coated with Geltrex containing extra-cellular matrix. The number of branch points was an indicator of the strength of angiogenic stimuli. As illustrated in FIG. 4, ELA treatment (0.5 µM) stimulated the formation of tubular structure (FIG. 4A). Quantitatively, the number of branch points was increased in a concentration-dependent manner by 71.9%, 222.8% and 266.7% in the presence of ELA at the concentrations of 0.1, 0.5 and 1 µM, respectively (FIG. 4B). To determine whether APJ mediated the angiogenic effect of ELA, APJ expression levels were modulated by over-expressing or knocking-down APJ (FIG. 4C) in HUVECs. In cells over-expressing APJ, ELA (0.1 µM) increased the tubular formation by 190.2% and 63.3%. Conversely, ELA was not effective in inducing the formation of tubular structures in APJ-knock down cells (FIG. 4D). Together, the results indicate that ELA exerts angiogenic effect directly through activation of APJ.

Example 6

Relaxation of Blood Vessels by ELA

Apelin is reported to relax vascular tone (14) and lower blood pressure. It was investigated whether ELA would regulate vascular tone using mouse endothelium-intact or endothelium-depleted (denuded) aortic rings. The aortic rings were induced to contraction with vasoconstrictor U46619 (final concentration, 30 nM). At the plateau of contraction, ELA or apelin-13 ($10^{-9}$ to $10^{-6}$ M) was added to induce relaxation. As depicted in FIG. 5A, incubation with ELA relaxed the blood vessel in a concentration-dependent manner with maximum relaxation of 73.7% in endothelium-intact vessels. Notably, only about 20% less relaxation was observed in denuded vessels at the corresponding concentrations, indicating an endothelium-independent relaxation by ELA.

To further determine whether nitric oxide (NO) participated in the relaxation, the blood vessels were pretreated with L-NAME, an NO production inhibitor. No significant difference was observed between the L-NAME-treated and none-treated vessels, indicating that NO production was not required for ELA-mediated relaxation (FIG. 5B). The effect of apelin-13 on blood vessels was studied in parallel for comparison. Apelin-13 induced blood vessel relaxation in endothelium-intact vessels with maximum relaxation of 79% at $10^{-6}$ M, but the removal of endothelium blunted its relaxing effect greatly by 48% to 31% (FIG. 5C), indicating that apelin-13 induced vessel relaxation largely in an endothelium-dependent manner than ELA did.

Example 7

ELA Expression in the Kidney and Role in Regulating Body Fluid Homeostasis

The question of whether ELA-APJ promotes human pluripotent stem cells (PSCs) into mesoderm derivatives including mesenchymal stem cells, adipocytes and cardiomyocytes was studied. It was found that ELA is a potent inducer of cardiomyocyte differentiation from PSCs (data not shown). Interestingly, ELA was selectively and highly expressed in the kidney. Without being bound by theory, the kidney is a crucial organ that maintains circulation homeostasis. ELA is a paracrine and/or endocrine hormone regulating the circulation system. Preliminary studies indicated that ELA expression localizes in cortical collecting duct cells and its ELA expression is about 100-fold higher than apelin in the kidney. Moreover, ELA treatment of HAC15 cells, a cell line of adrenocortical cells suppressed and antagonized angiotensin-induced aldosterone synthase CYP11B2. The data indicated that ELA was likely a diuretic hormone. It was found that exogenous infusion of ELA improves post-MI heart function. Thus, ELA is a kidney hormone that regulates the circulation system.

Systemically, heart, kidney, and vasculature comprises a closed system and maintains fluid homeostasis and blood pressure through hormonal regulation on fluid volume, vasculature tension and the heart contractility. For example, the heart secretes atrial natriuretic peptide (ANP) to dilate blood vessels and reduce water and sodium load to reduce blood pressure (13), whereas kidney cells secrete renin, which converts angiotensinogen to angiotensin to raise blood pressure and modulate heart function (14). The apelin receptor is reported to inhibit angiotensin II receptor via allosteric trans-inhibition (15). It was found that ELA suppressed angiotensin II induced aldosterone synthase in adrenocorticoid cell lines. This new kidney hormone acts in opposition to angiotensin in the kidney.

Chronic administration of ELA mitigates the changes in LV end-systolic dimension (LVDs) and LV ejection fraction (LVEF) at week 1 and 5 following chronic coronary ligation in mice, indicating its cardioprotective effects against post-infarct remodeling and dysfunction. In this aim, we propose to conduct a thorough studies to determine (1) the time course of the cardioprotective effects following coronary ligation. It was investigated if exogenous ELA protects the heart in acute ischemia phase and/or in chronic remodeling phase and (2) the underlying cellular mechanisms. It was hypothesized that exogenous ELA protects heart through its beneficial effects on myocardial inflammation, cell death, hypertrophy, and angiogenesis. Previous studies have shown that apelin-13 activates myocardial APJ. Therefore, apelin-13 was included for comparison.

Figure 6C:
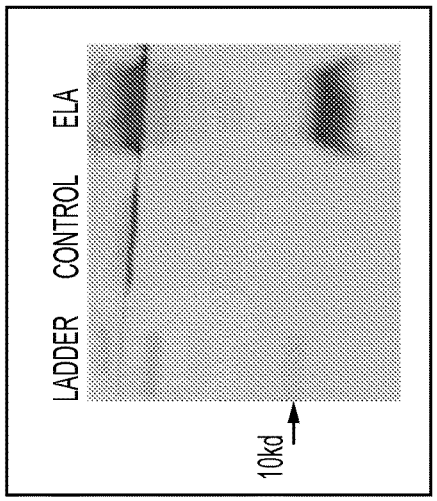
FIG. 6A-6C are photographs and bar graphs illustrating expression and endocrine function of ELA in the kidney.
Figure 6B:
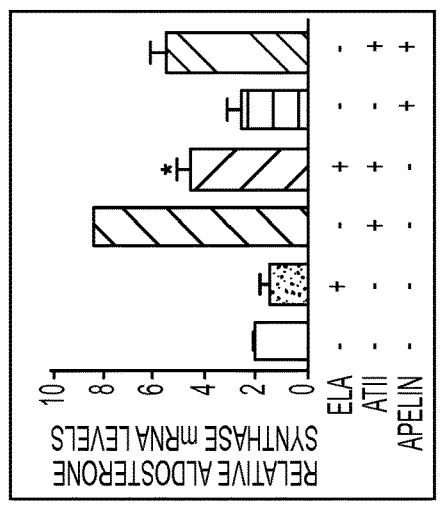
Figure 6A:
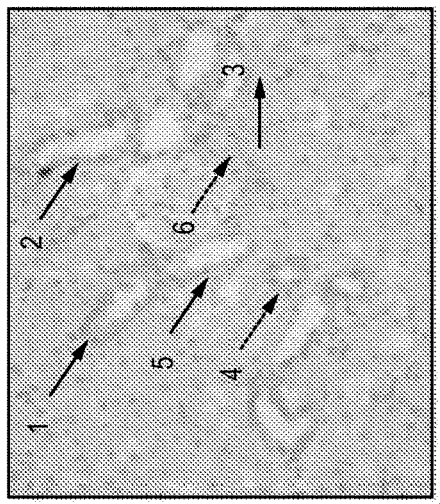

Myocardial infarction (MI) was induced by coronary artery ligation in mice. The sham operation (sham op) was used as a control. Each group of the animals received ELA, vehicle, or apelin-13 infusion via mini-pump. Echocardiography was conducted during the studies and pressure-volume loop (pv-loop) analysis, histology, tissue collections were conducted at the end of the animal studies. To analyze ELA's peptide protein expression, polyclonal antibodies were raised in rabbits (AbboMax, San Jose, Calif.). IHC studies showed that the antibodies cross-reacted with mouse, rat and human kidney tissue slides and stain the tubule structures. To investigate ELA's possible endocrine function, human adrenal cortical carcinoma cell line HAC15 was treated with ELA, apelin-13 and angiotensin II alone or in combination. FIG. 6A-6C show the expression and endocrine function of ELA in the kidney. In FIG. 6A, ELA immunohistochemistry in the rat kidney shows positively stained cells include cortical collecting tubules and distal convoluted tubules not in proximal tubules. In FIG. 6B, the gene expression was analyzed by qPCR in human adrenal cortical carcinoma cell line HAC15, which had been treated with ELA (50 nM), apelin-13 (50 nM) or angiotensin II (Ang II, 10 nM) alone or in combination for 47 hours. *, $p<0.05$. ELA significantly suppressed the Ang II-induced gene expression of aldosterone synthase, suggesting that an antagonism of ELA to Ang II in the adrenal gland. FIG. 6C reveals Western blot analysis of recombinant ELA secreted into the medium of 293 HEK cells over-expressing human ELA.

Example 8

ELA Improves Heart Performance in the Model of Heart Failure Induced by Cardiomyocyte Infarction (MI)

C57/BL wild type mice at age of 14-16 months old were used. Mice were subjected to either MI by permanent ligation or sham treatment with a loose suture of the proximal left anterior descending (LAD) coronary artery under general anesthesia by 2% isoflurane inhalation, and mechanical ventilation via oral intubation. Left thoracotomy in the 3-4 intercostal space was performed and the pericardium was opened to expose the LV and the LAD. The artery was circled a 8-0 silk suture, and then either ligated permanently or remained loose (sham).

Twelve to 14 mice were used in each group. ELA was infused at the same dose and rate as applied previously and the same mole amount of apelin-13 was used to compare cardioprotective equivalence. The peptides or vehicle (PBS) was loaded with a minipump (Model 1007D, Alzet), which was replaced every week.

Four time points were studied, including either 24 hours, weeks 1, 4, and 12 following the survival surgeries. This length of period generally spans the entire natural history of the post-infarct remodeling. All mice received echocardiography at the four time points. Pressure-volume loop analysis was performed immediately following the last echocardiography. At the end of PV loop analysis, blood and tissue samples were collected and animals euthanized. Hearts were quickly excised, dissected into infarct, peri-infarct, and noninfarct regions, and then flash-frozen separately for further histology, protein and RNA analyses. For immunohistochemical analysis, whole hearts were arrested in diastole with 1 mol/L KCl and then fixed in 10% formalin or embedded in optimal cutting temperature compound (OCT) and flash frozen.

Echocardiography

Animals were lightly sedated with 1.2-1.5% isoflurane, and transthoracic 2D-guided M-mode images of the LV and the ascending aorta, as well as pulse-wave Doppler images of the ascending aortic flow and mitral valve inflow were obtained using high-frequency ultrasound system (Vevo 2100, VisualSonics, Toronto, Canada), respectively via parasternal long or short views, superior sternal notch view, and apical 4-chamber view. Data were calculated with the accepted formulae, which have been validated in mice.

Histology for Infarct Size and Fibrosis

Hearts were cut into 5-μm slices following 10% formalin fixation and paraffin embedding. The sections were deparaffinized, rehydrated, and stained with Masson-trichrome. Digital images of the LV free wall were obtained using a Zeiss microscope equipped with AxioVision software (Carl Zeiss Imaging Solutions). The images were used for the measurement of cardiomyocyte cross-sectional area and fibrosis area using ImageJ software. At least 100 randomly selected cardiomyocytes per heart were measured and averaged over the cell number. The fibrosis area was measured over more than 20 randomly selected square of field (1 mm$^2$) per heart and is presented as a percentage of total area.

Figure 10:
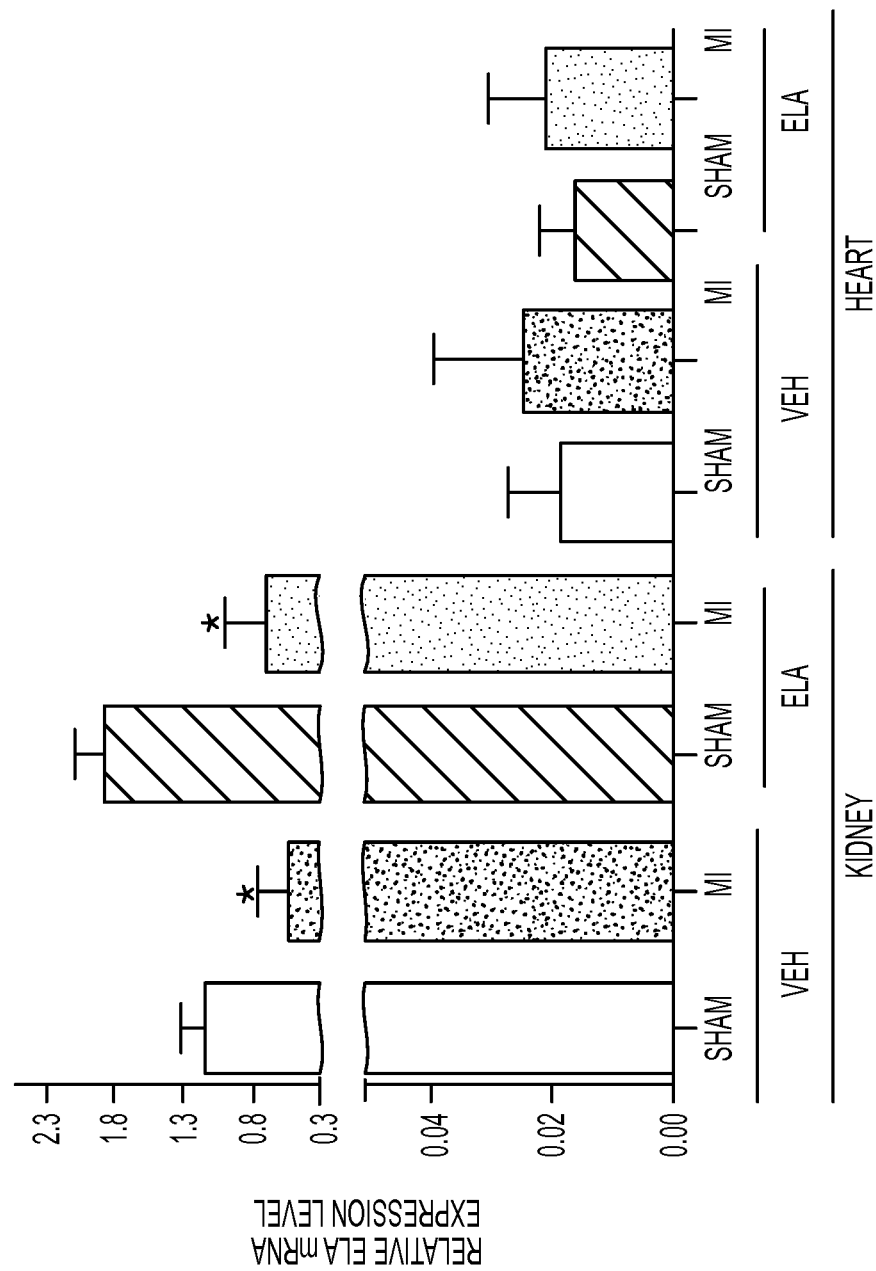
FIG. 10 is a bar graph illustrating kidney and heart ELA mRNA expression in mouse without (Sham) or with MI infused with ELA or vehicle measured by qRT-PCR adjusted to beta actin levels.
Figure 11B:
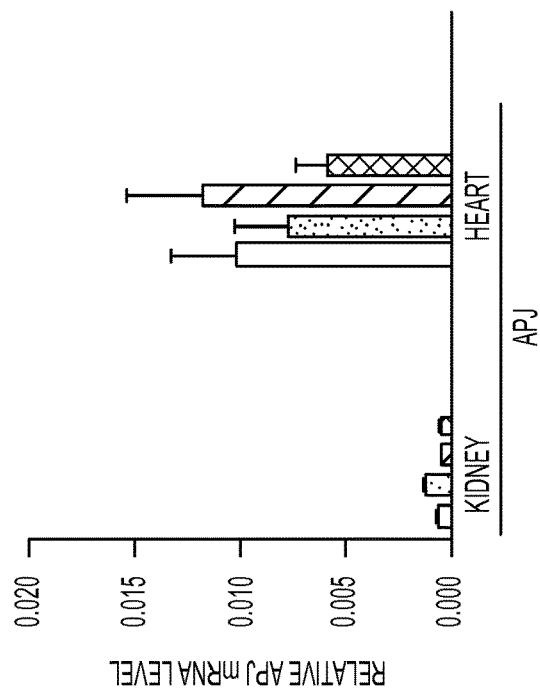
FIG. 11A-11B are bar graphs illustrating Apelin and APJ mRNA expression in mouse kidney and heart after infused ELA or vehicle.
Figure 11A:
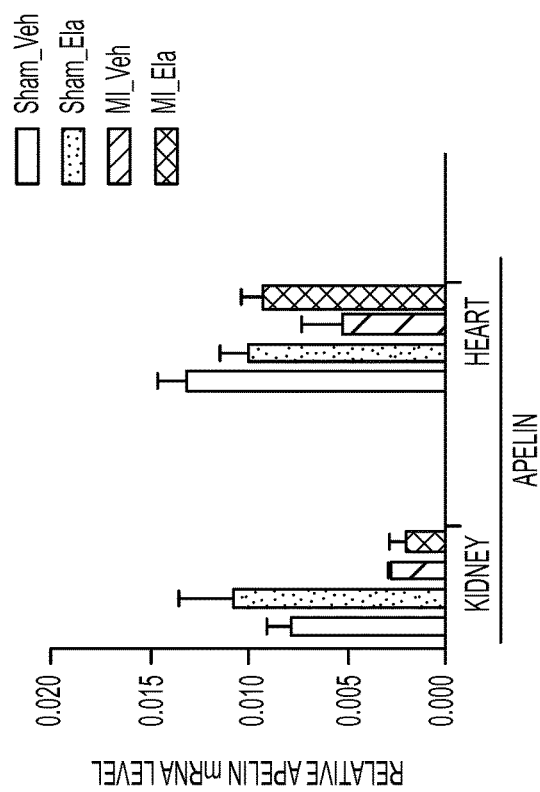

Coronary artery ligation (CAL) is a well-used procedure to create a mouse model of acute myocardial infarction (MI) and heart failure (HF). It was investigated whether ELA would have cardioprotective effects in C57/BL mice at the age of 14-16 months. ELA or vehicle (PBS) was infused to the groups of CAL or sham op mice simultaneously started from the procedure for 5 weeks. Echocardiography was conducted to access heart function before the procedure (baseline), and at 1 week and 5 weeks post-MI. As expected, MI resulted in left ventricular dilation (i.e. remodeling) and contractile dysfunction, as indicated by an increase of the left ventricle chamber size (LVDs and LVDd) and a decrease of left ventricle ejection fraction (LVEF) and fractional shortening (FS_LVD) (see Table 1 and FIG. 7A-7C).

sham operation. qPCRs were conducted for ELA, apelin and/or APJ. Kidney ELA mRNA level was decreased to 50% in low salt group and up 30% in high salt group compared to mice on normal Chow diet (FIG. 10). ELA mRNA was detectable in the mouse heart, but was significantly lower than in the kidney. ELA mRNA level was significantly lower in MI mice compare to age- and sex-matched mice with sham operations when infused either vehicle or ELA. (FIG. 11). Apelin expression is about 100-fold lower than ELA in kidney and is significant decreased in mice with MI. No different was found between MI and sham control mice but

|  | VEH | | ELA | |
|---|---|---|---|---|
|  | Baseline | Week 5 | Baseline | Week 5 |
| BW (g) | 29.29 ± 1.20 | 29.35 ± 0.70 | 32.40 ± 1.76 | 32.73 ± 1.38 |
| HR (bpm) | 420.22 ± 33.01 | 447.83 ± 31.50 | 474.75 ± 27.24 | 505.14 ± 12.73 |
| LVDs (mm) | 2.58 ± 0.13 | 3.95 ± 0.30** | 2.68 ± 0.11 | 3.47 ± 0.16* |
| LVDd (mm) | 3.83 ± 0.14 | 4.69 ± 0.25** | 3.87 ± 0.20 | 4.48 ± 0.17* |
| LVPWs (mm) | 1.07 ± 0.09 | 0.89 ± 0.06 | 1.01 ± 0.04 | 0.97 ± 0.04 |
| LVPWd (mm) | 0.78 ± 0.09 | 0.68 ± 0.05 | 0.70 ± 0.03 | 0.75 ± 0.05 |
| IVSs (mm) | 1.16 ± 0.08 | 0.81 ± 0.11 | 0.99 ± 0.04 | 0.96 ± 0.11 |
| IVSd (mm) | 0.74 ± 0.06 | 0.61 ± 0.09 | 0.61 ± 0.05 | 0.73 ± 0.07 |
| FS_LVD (%) | 32.56 ± 2.23 | 16.19 ± 1.83*** | 29.65 ± 4.16 | 22.68 ± 1.21** |
| FS_LVPW (%) | 28.54 ± 3.81 | 23.39 ± 2.54 | 30.36 ± 3.65 | 22.46 ± 4.49 |
| LVEF (%) | 61.10 ± 3.15 | 33.91 ± 3.58** | 61.84 ± 7.39 | 45.65 ± 2.16* |

Notably, ELA significantly mitigated the degree of left ventricular dilation and contractile dysfunction (Table 1 and FIG. 7A-7C). There was no statistical difference in heart performance in the sham op animals between the vehicle and ELA treatment. Three of nine control mice died, whereas one of eight ELA-treated mice died during the one-month of experimental period, although there was no statistical difference between the two groups, probably because of small sample size studied. These results clearly show that ELA has cardioprotective effects on progression of heart failure after acute MI.

Example 9

Figures 8A, 8B:
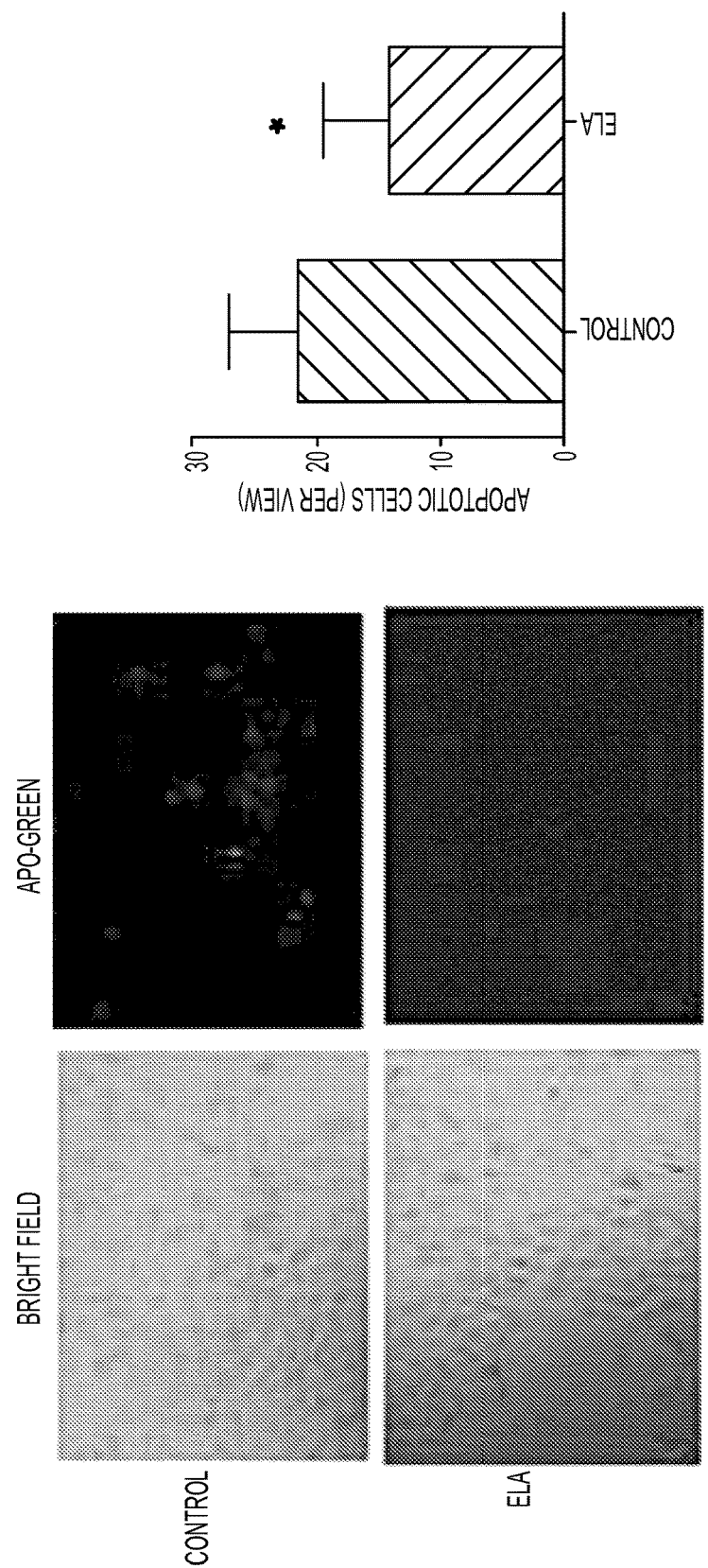
FIG. 8A-8B are photographs and bar graphs illustrating ELA decreasing hypoxia-induced cardiomyocyte apoptosis.
Figure 9:
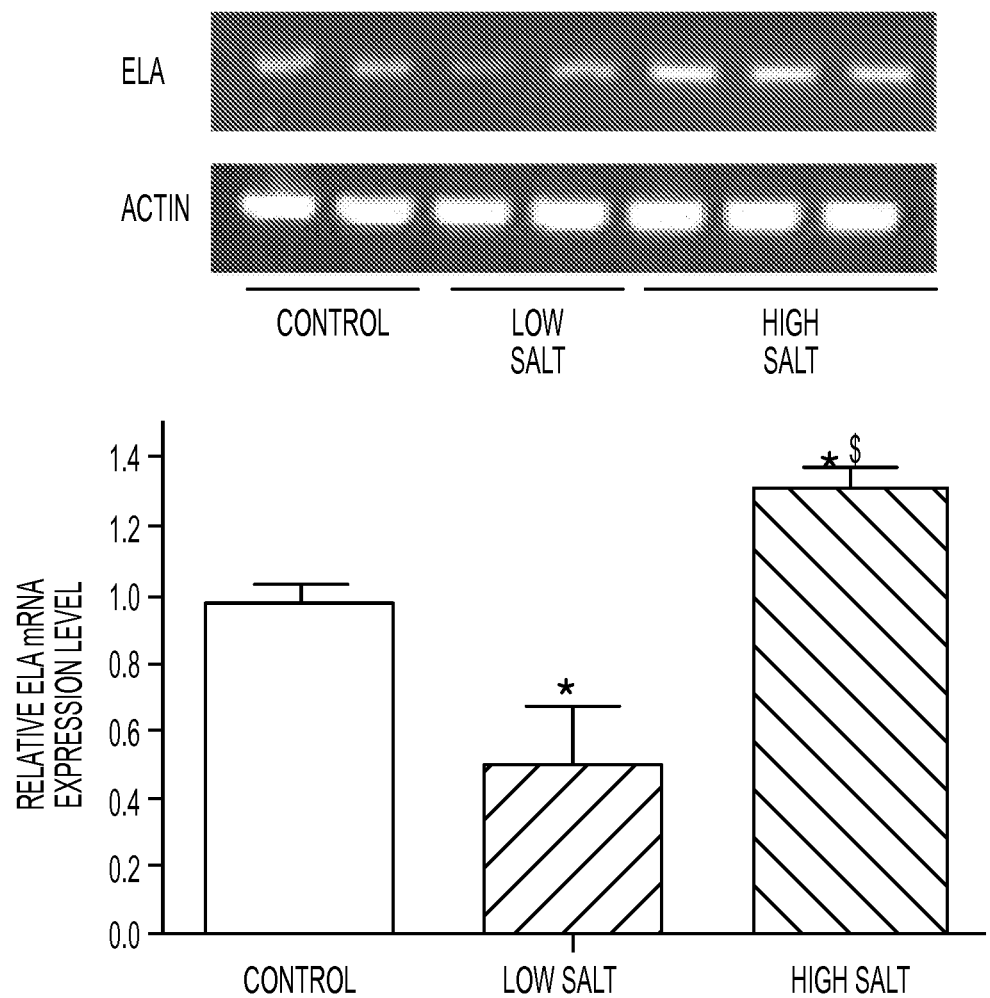
FIG. 9 is a bar graph illustrating ELA mRNA expression in mouse kidney on low or high salt diet measured by regular RT-PCR (upper panel) or qPCR (lower panel).

ELA is Anti-apoptotic in Human Cardiomyocytes Differentiated from Human Pluripotent Stem Cells Cellular mechanisms of cardioprotection in MI include the less cell death due to necrosis and apopotosis, increased angiogenesis and reduced fibrosis. It was found that activation of ELA-APJ signaling is proangiogenic by stimulating the tubule formation in human umbilical vein endothelial cells (HUVEC). Apelin is reported to protect against glucose deprivation-induced apoptosis in rat neonatal cardiomyocytes and to increase Akt and mTOR phosphorylation. We studied possible anti-apoptotic activities of ELA in cardiomyocytes under hypoxia, derived from differentiation of human pluripotent stem cells. TUNEL assay shows that treatment of the human cardiomyocytes with ELA (0.5 μM) significantly reduced the number of cells stained (FIG. 8A-FIG. 8B). Thus, ELA is protective against hypoxia-induced apoptosis in vitro.

Example 10

Regulation of ELA mRNA in Mice

Figure 12:
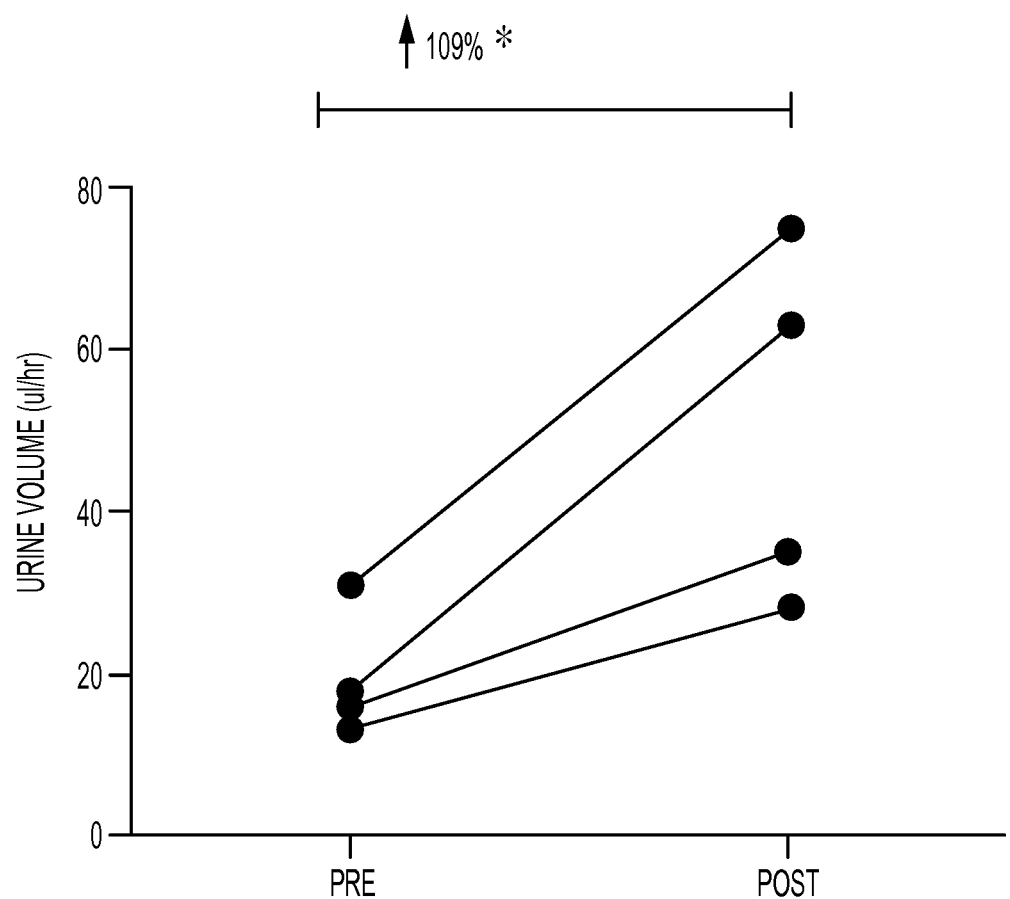
FIG. 12 is a graph illustrating increase of diuresis in mice after administration of ELA-32.

Kidney RNAs were extracted from mouse kidney under normal chow, low or high sodium diets (sodium 0.30%, 0.11% and 3.15% respectively), and from mouse with MI or APJ tended to decrease in the ELA-treated mice (FIG. 12A-12B).

Example 11

ELA Improves Diuresis in Mice

Figure 13:
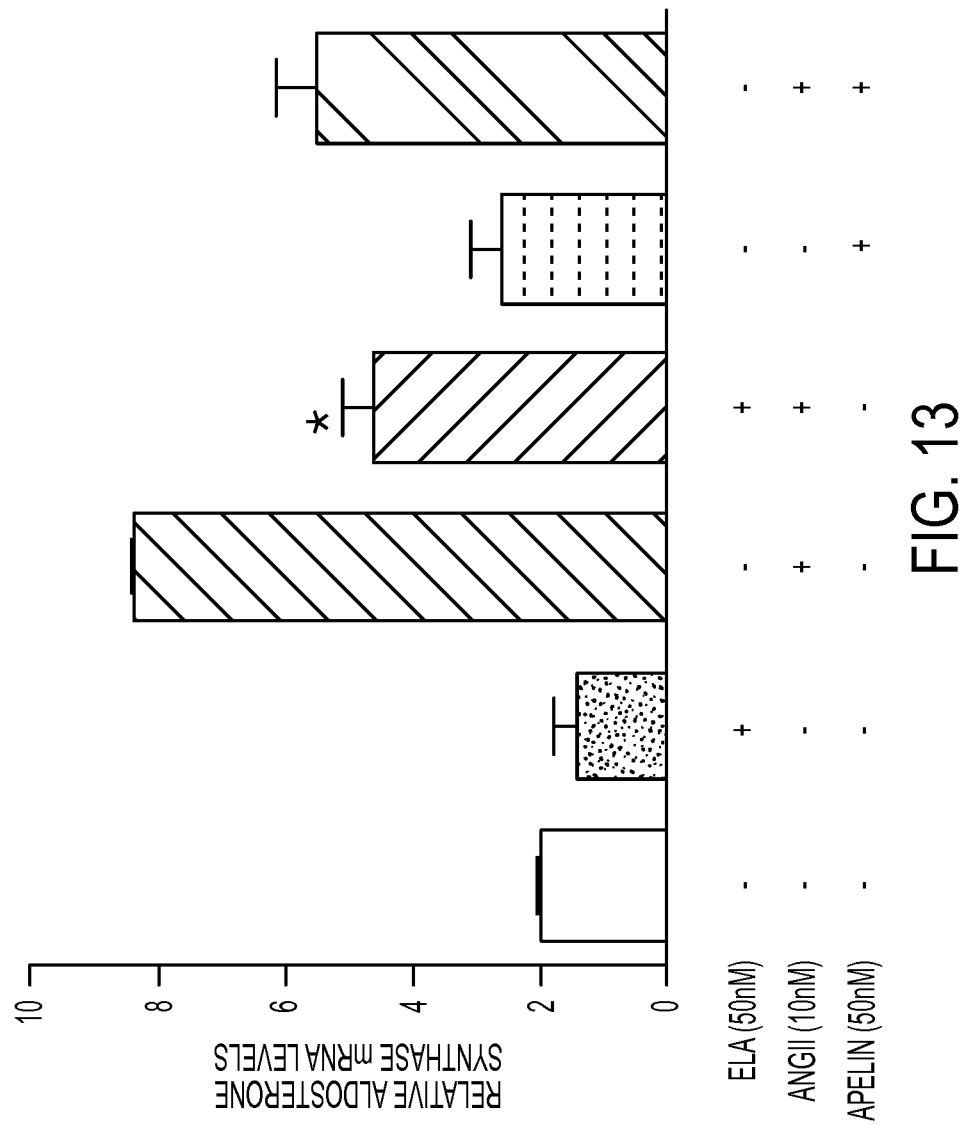
FIG. 13 is a bar graph illustrating ELA-32 suppression of angiotensin II-induced aldosterone synthase expression.

Four male C57/BL6 mice aged from 10 to 12 weeks were anesthetized with pentobarbital and then placed on a heated table to maintain body temperature and tracheotomized. Catheters were inserted into the external jugular veins for infusing normal saline to replace fluid loss and anesthesia, and into carotid artery for measuring blood pressure and heart rates. Urine was collected via a suprapubic cystostomy (PE-50-flanged end). After a 30-min stabilization period, urine was collected for a period of one hour as a baseline volume. Next, ELA was by injection intravenously (200 nmol/kg in 100 ul saline in one minute) and urine was collected for a period of additional one hour. As shown in FIG. 13, urine volume was increased by about one fold after ELA administration (p<0.05).

Figure 14:
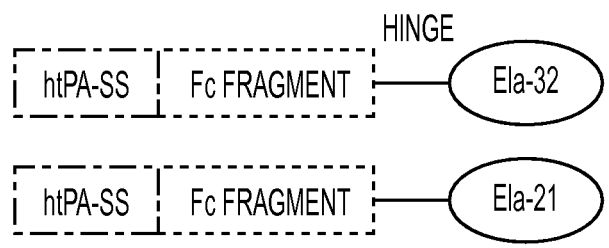
FIG. 14 is a schematic design of Fc-ELA-32 and Fc-ELA-21 constructs.

Human HAC15 cells, a line of adrenal cortical carcinoma, were treated with ELA, apelin-13 and angiotensin II alone or in combination. FIG. 14 shows that ELA significantly suppressed the Ang II-induced gene expression of aldosterone synthase. These results indicate that ELA may exert anti-heart activity by reducing aldosterone level.

Example 12

ELA-Fc Fusion Protein Mitigates Heart Damage Induced by MI

A fusion protein consisting of, from N- to C-terminus, the human tissue plasminogen secretion signal (htPA-SS), human immunoglobulin Fc domain (a well-used fusion protein carrier), and ELA-32 or ELA-21 (FIG. 15) in an expression vector was designed.

Figure 16B:
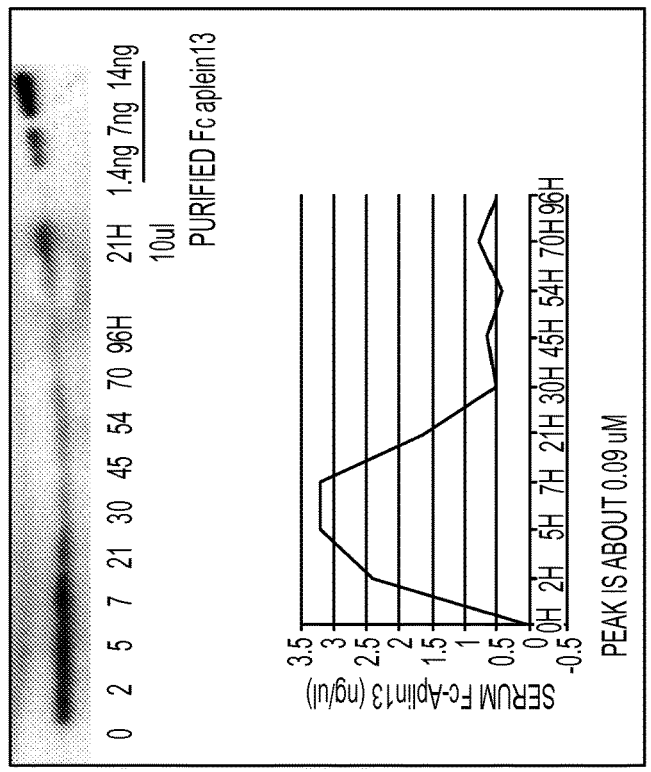
FIG. 16A-16B are graphs showing pharmacokinetics of Fc-ELA-32 and Fc-Apelin-13
Figure 16A:
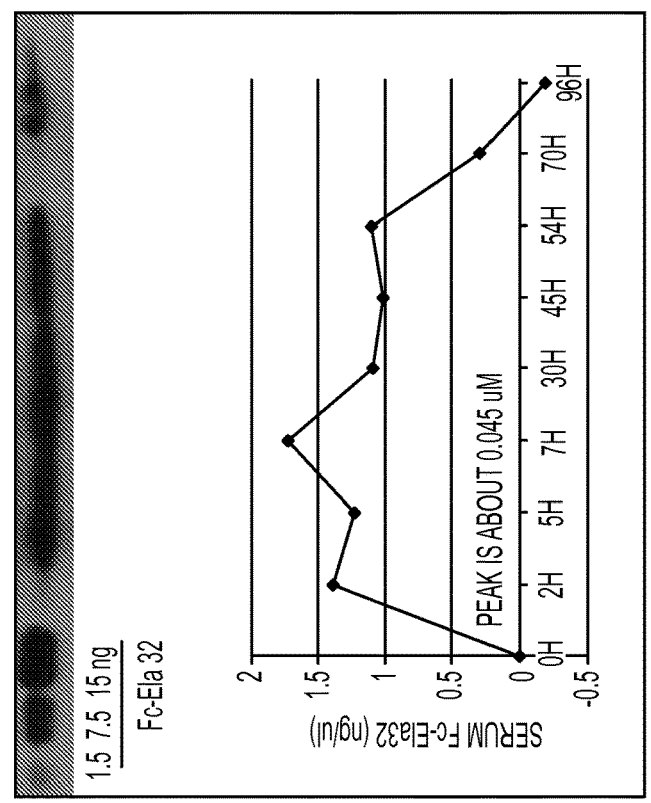
Figure 17:
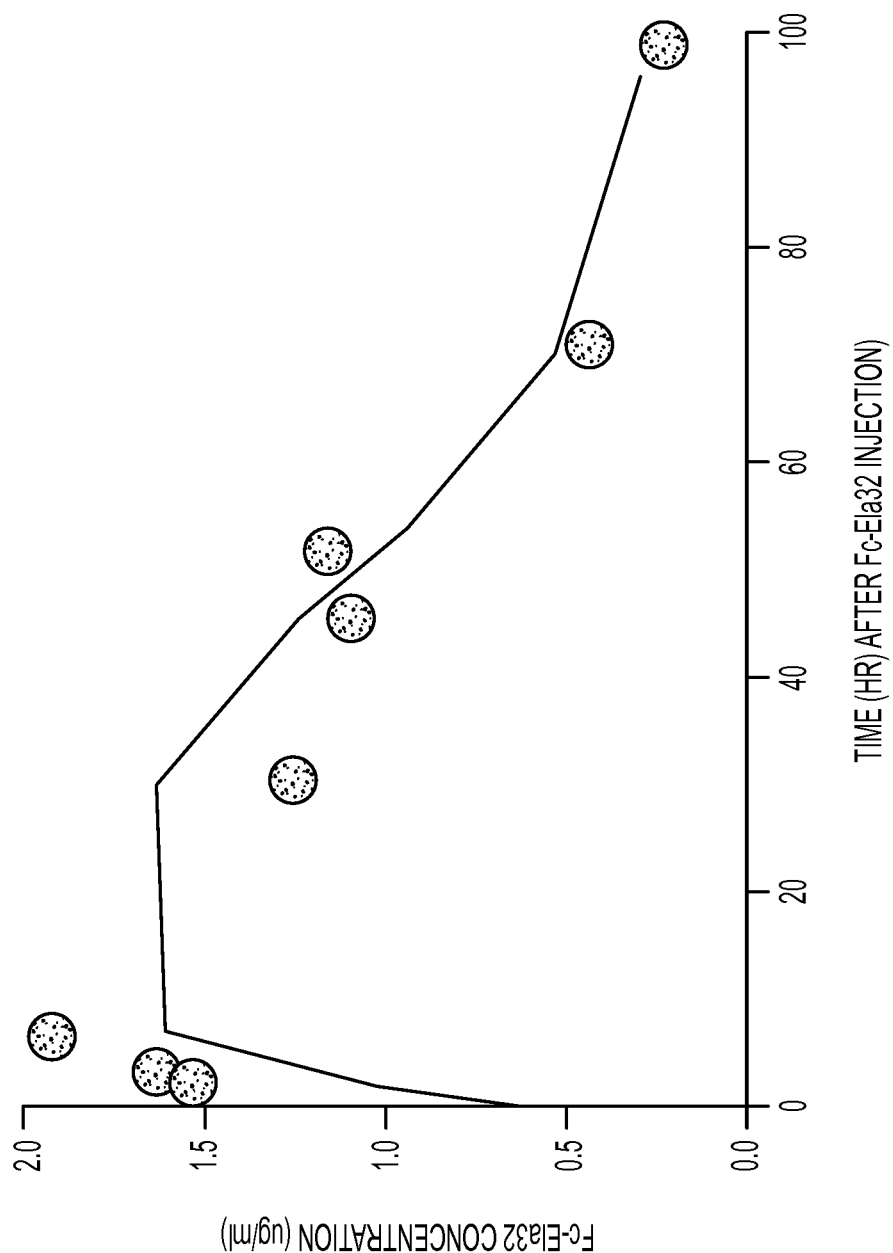
FIG. 17 is a bar graph showing serum levels of Fc-ELA-32 after subcutaneous injection.
Figure 18B:
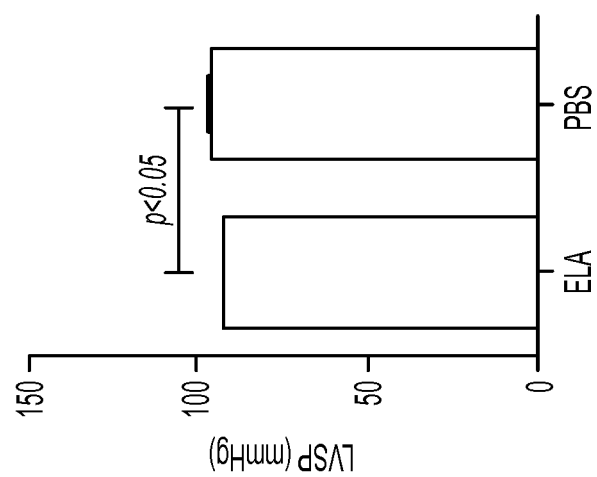
FIG. 18A-18B are bar graphs illustrating reduction in LVEDP in MI-induced heart failure in rats after administration of Fc-ELA-32.
Figure 18A:
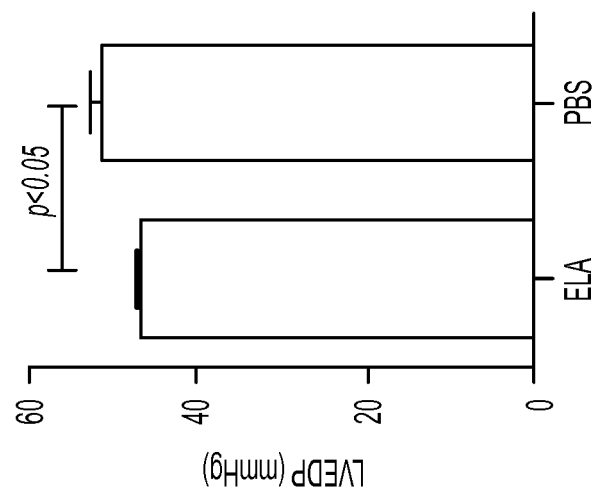

The respective vector was introduced into HEK293 cells to produce the fusion protein in supernatant for purification by Protein A affinity chromatography and the resulting fusion protein was used for functional studied in cells and in animals. As depicted in FIG. 16A-16C, treatment of the HEK293 cells over-expressing Apelin receptor (APJ)-EGFP with Fc-32 (0.2 μM) or Fc-21 (0.2 μM) for 30 min caused translocation or endocytosis of the receptor into cytoplasm, indicating an APJ activation by the ligand. Next, Fc-32 was administered into a mouse subcutaneously and collected blood for serum level measurement by Western blotting. Pharmacokinetic data for Fc-ELA-32 and Fc-Apelin were shown in FIG. 17A-17C. In FIG. 18, Fc-ELA-32 acutely elevated 2 hours after subcutaneous administration and lasted up to 72 hours at a level above 0.5 μg/ml.

It was studied whether Fc-ELA fusion proteins have cardioprotective activities in heart failure caused by myocardial infarction (MI) in rats. MI was inflicted by standard left anterior descending coronary artery ligation (CAL) in Sprague-Dawley rats (8-weeks old, male). One week post-operation, recombined Fc-ELA-32 protein was administrated by subcutaneous injection at the dosage of 300 μg/kg bodyweight/day for two weeks. Phosphate-buffered saline (PBS) was used as the control. One week after the administration or at the end of the four weeks of MI, cardiac performance was evaluated by a pressure transducer which was inserted retrograde from the right carotid artery to the left ventricle cavity. Heart tissue samples were taken and fixed with 4% paraformaldehyde for 24 hours and then embedded in paraffin and sectioned for histopathologic examination.

Figure 19B:
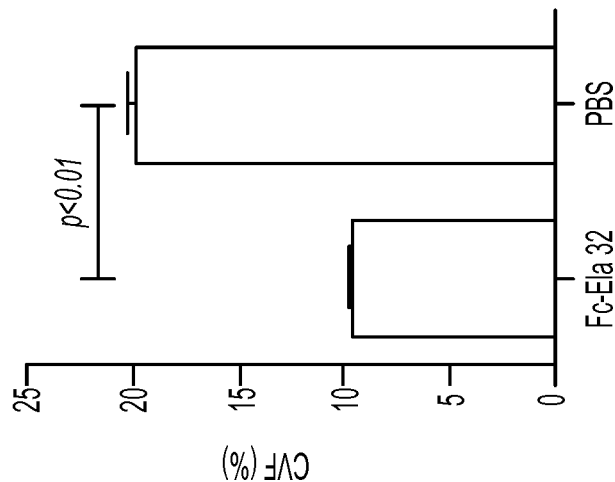
FIG. 19A-19B are photographs and a bar graph showing suppression of fibrosis of infarcted heart after administration of Fc-ELA-32.
Figure 19A:
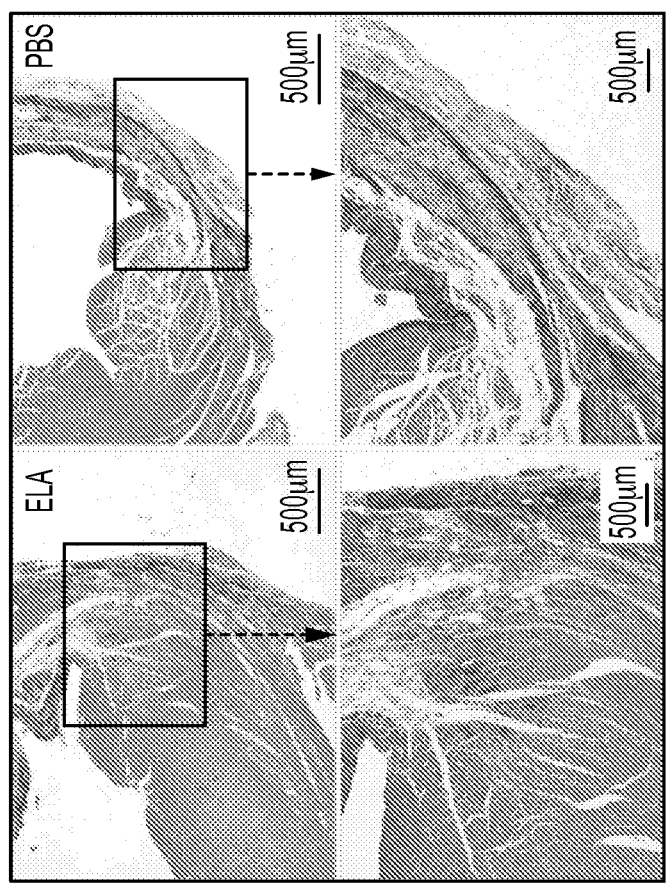

Following myocardial infarction (MI), LVEDP can be elevated in association with larger infarct size and increased circulatory volume. FIG. 19A-19B shows that Fc-ELA-32 administration decreased LVEDP, indicating an improvement of the dysfunctional heart.

Example 13

ELA Reduces Heart Fibrosis

Apoptosis was assessed by terminal deoxynucleotidyl transferase-mediated dUTP nick end labeling (TUNEL) and caspase-3 activity assay. The TUNEL staining and methyl green counterstaining were performed using TdT-FragEL apoptosis detection kits (Calbiochem, San Diego, Calif.). TUNEL-positive nuclei in the LV free wall were counted within a 4-mm$^2$ square of field. The number was averaged over four randomly selected fields per section and five sections per heart.

Figure 20B:
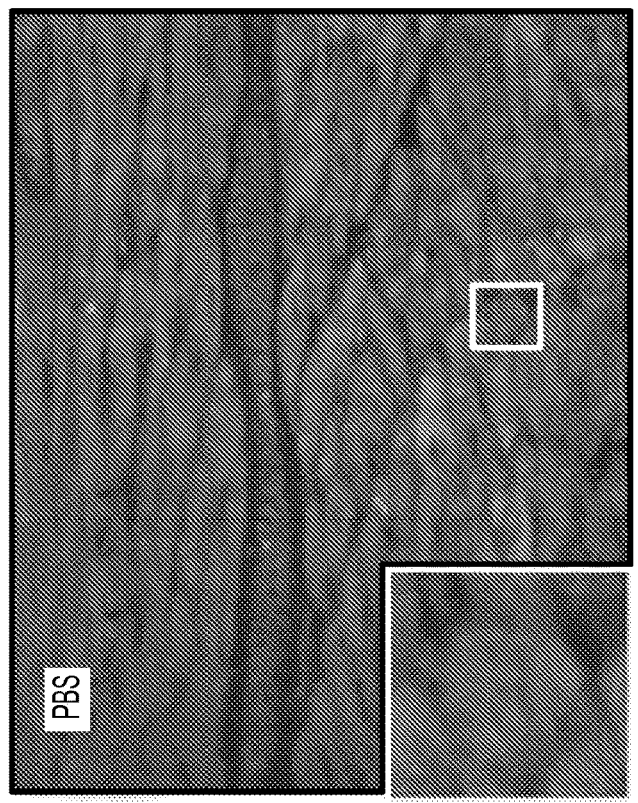
FIG. 20A-20B are photographs showing that administration of Fc-ELA-32 increases cardiomyocyte proliferation.
Figure 20A:
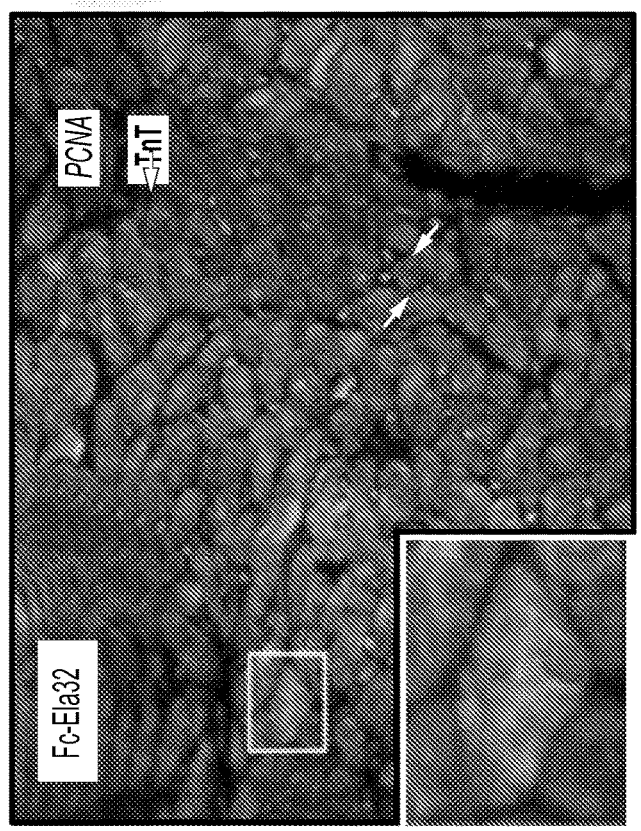

Masson staining which specifically stains collagens in blue was conducted on tissue sections of the infarcted heart area. Collagen volume fraction (CVF) is calculated by dividing of the blue stained area, which scattered between the surviving myocytes and around the blood vessels by the total area. As shown in FIG. 20A-20B, CVF was significantly decreased by 50% in Fc-ELA-32-treated than the control heart, indicating that Fc-ELA suppresses fibrosis of the infarcted heart.

Example 14

ELA Increases Cardiomyocyte Proliferation and Reduces Apoptosis

Figure 21B:
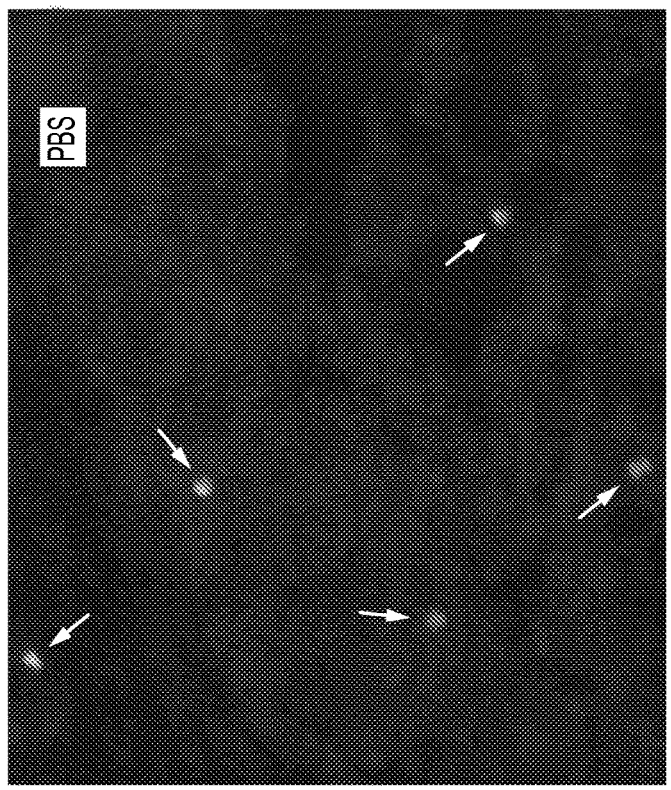
FIG. 21A-21B are photographs showing reduction of cardiomyocyte apoptosis after administration of Fc-ELA-32.
Figure 21A:

To understand mechanism of cardioprotective effect in MI heart, we conducted immunofluorescent staining in the heart tissue slides to examine cardiomyocyte responses to ELA treatment. To examine cardiomyocyte proliferation, the tissue sections were stained with both mouse monoclonal antibody against proliferating cell nuclear antigen (PCNA), a marker of cell proliferation (DNA synthesis and repair) and rabbit polyclonal antibody against troponin-T, a cardiomyocyte marker. As revealed in FIG. 21A-FIG. 21B, more cardiomyocytes in the mice treated with Fc-ELA-32 were stained by PCNA, compared to the control rats, indicating that ELA can increase cardiomyocyte proliferation near the infarct region.

Figure 22A:
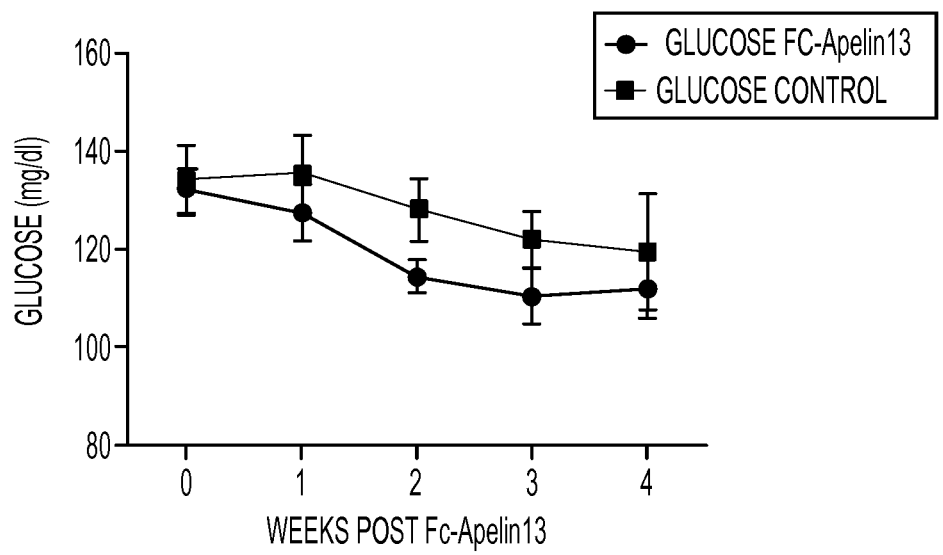
FIG. 22A-22B are graphs showing that administration of Fc-Apelin-13 lowers glucose in diet-induced obese mice.
Figure 22B:
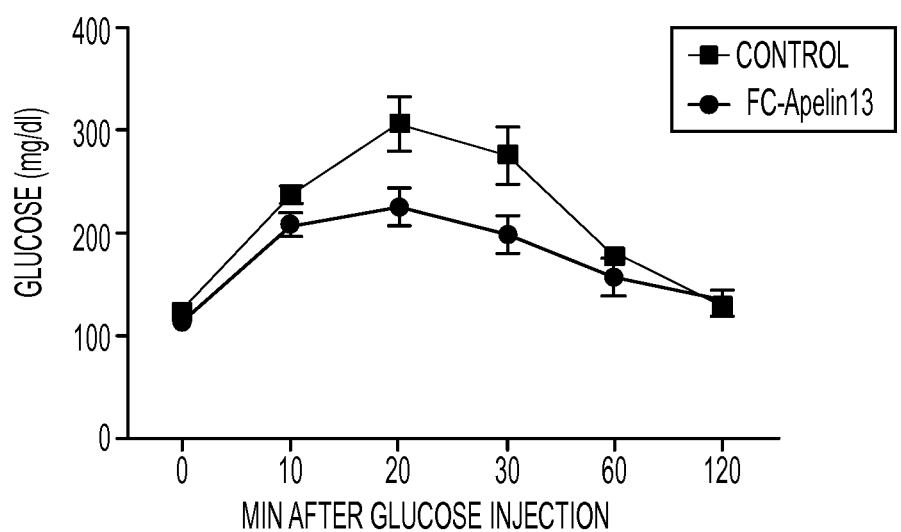
Figure 23:
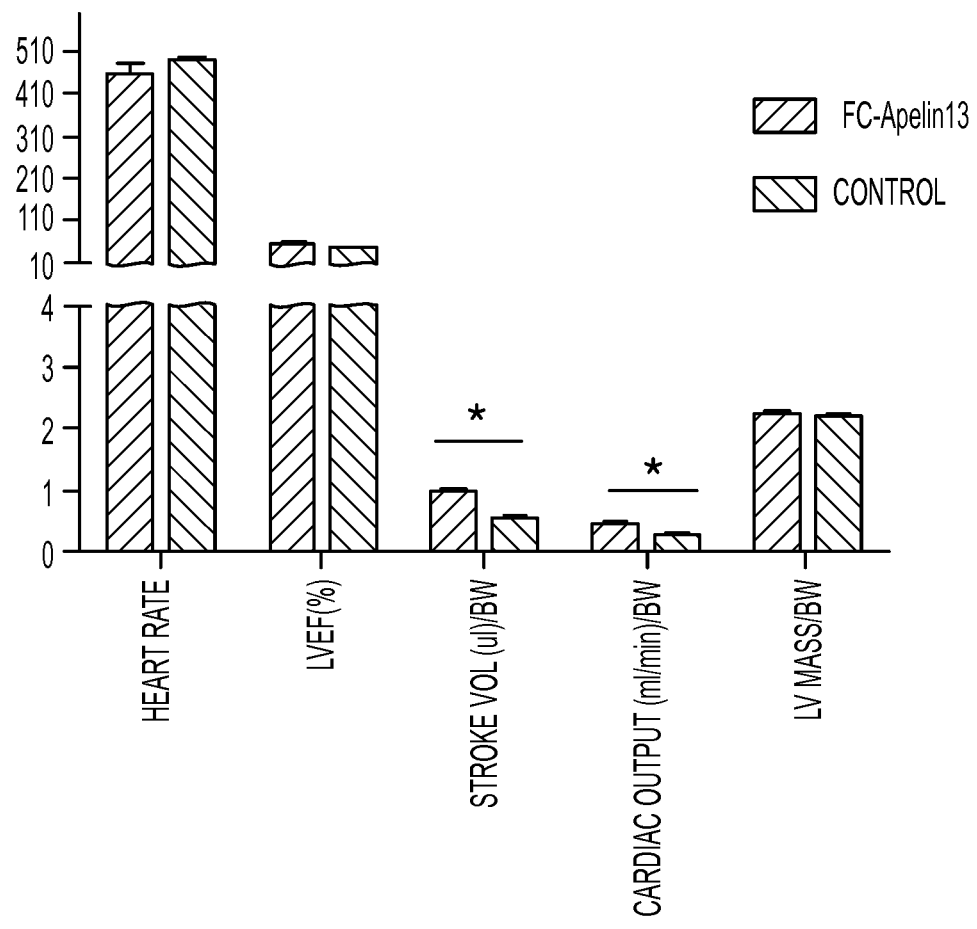
FIG. 23 is a graph showing improvement in heart performance after administration of Fc-Apelin-13 in diet-induced obese mice.

Terminal deoxynucleotidyl transferase dUTP nick end labeling (TUNEL) is a method for detecting DNA fragmentation by labeling the terminal end of nucleic acids and is well used for measuring cell apoptosis. Heart sections were incubated in the 20 μg/ml proteinase K under 37° C. for 30 min, and then incubated in the TUNEL detection buffer for 60 min. As a result, apoptotic cells were labeled by green fluorescence. FIG. 22A-22B shows that ELA-treated heart has much less green-labeled cells, indicating that ELA treatment protects against MI-induced cardiomyocyte apoptosis.

REFERENCES

All references cited herein are hereby incorporated by reference in their entirety.
1. O'Dowd, B. F., Heiber, M., Chan, A., Heng, H. H., Tm., L. C., Kennedy, J. L., Shi, X., Petronis, A., George, S. R., and Nguyen, T. 1993. A human gene that shows identity with the gene encoding the angiotensin receptor is located on chromosome 11. Ge1 1e 136:355-360.
2. Tatemoto, K., Hosoya, M., Habata, Y., Fujii, R., Kakegawa, T., Zou, M. X., Kawamata, Y., Fukusumi, S., Hinuma, S., Kitada, C., et al. 1998. Isolation and characterization of a novel endogenous peptide ligand for the human APJ receptor. Biochem Blophys Res Comm 1111 251:471-476.
3. Hamada, J., Kimura, J, Ishida, J., Kohda, T., Morishita, S., Ichihara, S., and Fukamizu, A. 2008. Evaluation of novel cyclic analogues of apelin. J Mol Med 22:547-552.
4. D'Aniello, C., Lonardo, E., Iaconis, S., Guardiola, O., Liguoro, A. M., Liguori, G. L., Autiero, M., Carmeliet, P., and Minchiotti, G. 2009. G protein-coupled receptor APJ and its ligand apelin act downstream of Cripto to specify embryonic stem cells toward the cardiac lineage through extracellular signal-regulated kinase/p70S6 kinase signaling pathway. Circ Res 105:231-238.
5. Medhurst, A. D., Jennings, C. A., Robbins, M. J., Davis, R. P., Ellis, C., Winborn, K. Y., Lawrie, K. W., Hervieu, G., Riley, G., Bolaky, J. E., et al. 2003. Pharmacolognl and immunohistochemical characterization of the APJ receptor and its endogenous ligand apelin. Neurochem 84:11162-1172.
6. Tatemoto, K., Takayama, K., Zou, M. X., Kumaki, I., Zhang, W., Kumano, K., and Fujimiya, M. 2001. The novel peptide apelin lowers blood pressure via a nitric oxide-dependent mechanism. Regul Pepi 99:87-92.
7. Ishida, J., Hashimoto, T., Hashimoto, Y., Nishiwaki, S., Jguchi, T., Harada, S., Sugaya, T., Matsuzaki, H., Yamamoto, R., Shiota, N., et al. 2004. Regulatory roles for APJ, a seven-transmembrane receptor related to angiotensin-type lreceptor in blood pressure in vivo. J Biol Chem 279:26274-26279.
8. Ching, S. C., Ho, L., Tian, J., and Reversade, B. 2013. ELABELA: a hormone essential for heart development signals via the apelin receptor. Dev Cell 27:672-680.

9. Pauli, A., Norris, M. L., Valen, E., Chew, G. L., Gagnon, J. A., Zimmerman, S., Mitchell, A., Ma, J., Dubrulle, J., Reyon, D., et al. 2014. Toddler an embryonic signal that promotes cell movement via Apelin receptors. Science 343:1248636.
10. Thorsell, A., Tapocik, J. D., Liu, K., Zook, M., Bell, L., Flanigan, M., Patnaik, S., Marugan, J., Damadzic, R., Dehdashti, S. J., et al. 2013. A novel brain penetrant NPS receptor antagonist, NCGC00185684, blocks alcohol-induced ERK-phosphorylation in the central amygdala and decreases operant alcohol self-administration in rats. J Neurosci 33:10132-10142.
11. Dong, Y., Wu, Y., Wu, M, Wang, S., Zhang, J., Xie, Z., Xu, J., Song, P., Wilson, K., Zhao, Z., et al. 2009. Activation of protease calpain by oxidized and glycated LDL increases the degradation of endothelial nitric oxide synthase. J Cell Mo/Med 13:2899-2910.
12. Dong, Y., Zhang, M., Wang, S., Liang, B., Zhao, Z., Liu, C., Wu, M., Choi, H. C., Lyons, T. J., and Zou, M. H. 2010. Activation of AMP-activated protein kinase inhibits oxidized LDL-triggered endoplasmic reticulum stress in vivo. Diabetes 59:1386-1396.
13. O'Carroll, A. M., Lolait, S. J., Harris, L. E., and Pope, G. R. 2013. The apelin receptor APJ: journey from an orphan to a multifaceted regulator of homeostasis. J Endocrinol 219:R13-35.
14. Zhong, J. C., Yu, X. Y., Huang, Y., Yung, L. M., Lau, C. W., and Lin, S. G. 2007. Apelin modulates aortic vascular tone via endothelial nitric oxide synthase phosphorylation pathway in diabetic mice. Cardiovasc Res 74:388-395.
15. Hosoya, M., Kawamata, Y., Fukusumi, S., Fujii, R., Habata, Y., Hinuma, S., Kjtada, C., Honda, S., Kurokawa, T., Onda, H., et al. 2000. Molecular and functional characteristics of APJ. Tissue distribution of mRNA and interaction with the endogenous ligand apelin. J Biol Chem 275: 21061-21067.
16. Szokodi, I., Tavi, P., Foldes, G., Voutilainen-Myllyla, S., Jives, M., Tokola, H., Pikkarniinen, S., Piuhola, J., Rysa, J., Toth, M., et al. 2002. Apelin, the novel endogenous ligand of the orphan receptor APJ, reg111lates cardiac contractility. Cfrc Res 91:434-440.
17. Kasai, A., Shintani, N., Oda, M., Kakuda, M., Hashimoto, H., Matsuda, T., Hinuma, S., and Baba, A. 2004. Apelin is a novel angiogenic factor in retinal endothelial cells. Biochem Biophys Res Commun 325: 395-400.
18. Kalin, R. E., Kretz, M. P., Meyer, A. M., Kispert, A., Heppner, F. L., and Brandli, A. W.2007. Paracrine and autocrine mechanisms of apelin signaling govern embryonic and tumor angiogenesis. Dev Biol. 305:599-614.
19. Ashley, E. A., Powers, J., Chen, M., Kundu, R., Finsterbach, T., Caffarelli, Deng, A., Eichhorn, J., Mahajan, R., Agrawal, R., et al. 2005. The endogenous peptide apelin potently improves cardiac contractility and reduces cardiac loading in vivo. Cardiovasc Res 65:73-82.
20. Perjes, A., Skoumal, R., Tenhunen, O., Konyi, A., Simon, M., Horvatlh, I. G., Kerkela, R., Ruskoaho, H., and Szokodi, I.2014. Apelin increases cardiac contractility via protein kinase Cepsilon- and extracellular signal-regulated kinase-dependent mechanisms. PLoS 011e 9:e93473.
21. Lee, D. K., Saldivia, V. R., Nguyen, T., Cheng, R., George, S. R., and O'Dowd, B. F. 2005. Modification of the terminal residue of apelin-13 antagonizes its hypotensive action. Endocronology 146:231-236.
22. Pisarenko, O. I., Pelogeykina, Y. A., Bespalova Zh, D., Serebryakova, L. I., Sidorova, M. V., Az'muko, A. A., Khatri, D. N., Studneva, I. M., Pal'keeva, M. E., Tskitishvili, O. V., et al. 2012. Limitation of myocardial infarction by a structural analog of the peptide apclin-12. Dok/Biol Sci 443:65-67.
23. Kleinz, M. J., and Baxter, G. F. 2008. Apelin reduces myocardial reperfusion injury independently of PI3K/Akt and P70S6 kinase. Regul Pepi 146:271-277.
24. Jia, Y. X., Pan, C. S., Zhang, J. Geng, B., Zhao, J., Gcrns, H., Yang, J., Chang, J. K., Tang, C. S., and Qi, Y. F. 2006. Apelin protects myocardial injury induced by isoproterenol in rats. Regul Pepi 133:147-154.
25. Zeng, H., He, X., Hou, X., Li, L., and Chen, J. X. 2014. Apelin gene therapy increases myocardial vascular density and ameliorates diabetic cardiomyopathy via upregulation of sirtuin 3. Am J Physlol Heart Circ Physiol 306:H585-597.
26. Li, L., Zeng, H., Hou, X., He, X., and Chen, J. X.2013. Myocardial injection of apelin-overexpressing bone marrow cells improves cardiac repair via upregulation of Sirt3 after myocardial infarction. PLoS 011e 8:e71041.
27. Wang, W., McKinnie, S. M., Patel, V. B., Haddad, G., Wang, Z., Zhabyeyev, P., Das, S. K., Basu, R., McLean, B., Kandalam, V. 2013. Loss of Apelin exacerbates myocardial infarction adverse remodeling and ischemia-reperfusion injury: therapeutic potential of synthetic Apelin analogues. J Am Heart Assoc 2:e000249.
28. Maguire, J. J., K Jeinz, M. J., Pitkin, S. L., and Davenport, A. P.2009. (Pyrlapelin (1)-13 identified as the predominant apelin isoform in the human heart: vasoactive mechanisms and inotropic action in disease. Hypertension 54:598-604.
29. Katugampola, S. D., Maguire, J. J., Matthewson, S. R., and Davenport, A. P.2001. ((125)1]-(Pyr(1))Apelin-13 is a novel radio ligand for localizing the APJ orphan receptor in human and rat tissues with evidence for a vasoconstrictor role in man. Br J Pharmacol 132:1255-1260.
30. Kang, Y., Kim, J., Anderson, J. P., Wu, J., Gleim, S. R., Kundu, R. K., McLean, D. L., Kim, J. D., Park, H., Jin, S. W., et al. 2013. Apelin-APJ signaling is a critical regulator of endothelial MEF2 activation in cardiovascular development. Circ Res 113:22-31.
31. Charo, D. N., Ho, M., Fajardo, G., Kawana, M., Kundu, R. K., Sheikh, A. Y., Finsterbach, T. P., Leeper, N. J., Ernst, K. V., Chen, M. M., et al. 2009. Endogenous regulation of cardiovascular function by apelin-APJ. Am J Physiol Heart Circ Physiol 297:H1904-1913.
32. Kuba, K., Zhang, L., Imai, Y., Arab, S., Chen, M., Maekawa, Y., Leschnik, M., Leibbrandt, A., Markovic, M., Schwaighofer, J., et al. 2007. Impaired heart contractility in Apelin gene-deficient mice associated with aging and pressure overload. Gire Res 101:e32-42.
33. Scimia, M. C., Blass, B. E., and Koch, W. J. 2014. Apelin receptor: its responsiveness to stretch mechanisms and its potential for cardiovascular therapy. Expert Rev Cardiovasc Tiier 12:733-741.
34. Roberts, E. M., Newson, M. J., Pope, G. R., Landgraf, R., Lolait, S. J., and O'Carroll, A. M. 2009. Abnormal fluid homeostasis in apelin receptor knockout mice. J Endocrinol 202:453-462.
35. Houser S R, Margulies K B, Murphy A M, Spinale F G, Francis G S, Prabhu S D, Rockman H A, Kass D A, Molkentin J D, Sussman M A, et al. Animal models of heart failure: a scientific statement from the American Heart Association. *Circulation research*. 2012; 111(1): 131-50.

36. Falcao-Pires I, Ladeiras-Lopes R, and Leite-Moreira A F. The apelinergic system: a promising therapeutic target. *Expert opinion on therapeutic targets.* 2010; 14(6):633-45.
37. Ladeiras-Lopes R, Ferreira-Martins J, and Leite-Moreira A F. The apelinergic system: the role played in human physiology and pathology and potential therapeutic applications. *Arquivos brasileiros de cardiologia.* 2008; 90(5): 343-9.
38. Yu X H, Tang Z B, Liu L J, Qian H, Tang S L, Zhang D W, Tian G P, and Tang C K. Apelin and its receptor APJ in cardiovascular diseases. *Clinica chimica acta; international journal of clinical chemistry.* 2014; 428(1-8.
39. Charles C J. Update on apelin peptides as putative targets for cardiovascular drug discovery. *Expert opinion on drug discovery.* 2011; 6(6):633-44.
40. Chng S C, Ho L, Tian J, and Reversade B. ELABELA: a hormone essential for heart development signals via the apelin receptor. *Developmental cell.* 2013; 27(6):672-80.
41. Pauli A, Norris M L, Valen E, Chew G L, Gagnon J A, Zimmerman S, Mitchell A, Ma J, Dubrulle J, Reyon D, et al. Toddler: an embryonic signal that promotes cell movement via Apelin receptors. *Science.* 2014; 343(6172): 1248636.
42. Wang Z, Yu D, Wang M, Wang Q, Kouznetsova J, Yang R, Qian K, Wu W, Shuldiner A, Sztalryd C, et al. ELAbELA-Apelin Receptor Signaling Pathway is Functional in Mammalian Systems. *Scientific reports.* 2015; 5(8170.
43. Chun H J, Ali Z A, Kojima Y, Kundu R K, Sheikh A Y, Agrawal R, Zheng L, Leeper N J, Pearl N E, Patterson A J, et al. Apelin signaling antagonizes Ang II effects in mouse models of atherosclerosis. *The Journal of clinical investigation.* 2008; 118(10):3343-54.
44. Mielniczuk L M, Lamas G A, Flaker G C, Mitchell G, Smith S C, Gersh B J, Solomon S D, Moye L A, Rouleau J L, Rutherford J D, et al. Left ventricular end-diastolic pressure and risk of subsequent heart failure in patients following an acute myocardial infarction. *Congestive heart failure.* 2007; 13(4):209-14.
45. Conrad C H, Brooks W W, Hayes J A, Sen S, Robinson K G, and Bing O H. Myocardial fibrosis and stiffness with hypertrophy and heart failure in the spontaneously hypertensive rat. *Circulation.* 1995; 91(1):161-70.
46. Iles L, Pfluger H, Phrommintikul A, Cherayath J, Aksit P, Gupta S N, Kaye D M, and Taylor A J. Evaluation of diffuse myocardial fibrosis in heart failure with cardiac magnetic resonance contrast-enhanced T1 mapping. *Journal of the American College of Cardiology.* 2008; 52(19): 1574-80.
47. Schwarz F, Mall G, Zebe H, Blickle J, Derks H, Manthey J, and Kubler W. Quantitative morphologic findings of the myocardium in idiopathic dilated cardiomyopathy. *The American journal of cardiology.* 1983; 51(3):501-6.
48. Konstantinidis K, WhELAn R S, and Kitsis R N. Mechanisms of cell death in heart disease. *Arteriosclerosis, thrombosis, and vascular biology.* 2012; 32(7): 1552-62.
49. Whelan R S, Kaplinskiy V, and Kitsis R N. Cell death in the pathogenesis of heart disease: mechanisms and significance. *Annual review of physiology.* 2010; 72:19-44.

What is claimed is:

1. A method of treating a subject suffering from a cardiac condition or having a risk factor for developing a cardiac condition, comprising administering to the subject an effective amount of a peptide in a pharmaceutically acceptable form selected from the group consisting of: SEQ ID NO:2 (ELA-21); and a fragment, variant, or derivative of ELA-21 that is at least 95% identical to ELA-21.

2. A method of treating a subject suffering from a cardiac condition or having a risk factor for developing a cardiac condition, comprising administering to the subject an effective amount of a peptide in a pharmaceutically acceptable form selected from the group consisting of: SEQ ID NO:5; and a fusion of Fc with a fragment, variant, or derivative of ELA-21 that is at least 95% identical to ELA-21.

3. A method for treating a subject suffering from a cardiac condition or having a risk factor for developing a cardiac condition comprising:
   (i) identifying a subject suffering from a cardiac condition or having a risk factor for developing a cardiac condition; (ii) measuring an amount of a peptide of SEQ ID NO: 1, or a peptide of SEQ ID NO: 2, or a peptide of SEQ ID NO: 3, in the bloodstream of the subject suffering from a cardiac condition or having a risk factor for developing a cardiac condition; (iii) measuring an amount of a peptide of SEQ ID NO: 1, or a peptide of SEQ ID NO: 2, or a peptide of SEQ ID NO: 3, in the bloodstream of a normal control subject; (iv) comparing the amounts of the peptide of SEQ ID NO: 1, or SEQ ID NO: 2, or SEQ ID NO: 3, in the subject suffering from a cardiac condition or having a risk factor for developing a cardiac condition and that in the normal control subject; and (v) treating the subject with an effective amount of a peptide in a pharmaceutically acceptable form,
   wherein the peptide is selected from the group consisting of: SEQ ID NO:2 (ELA-21); and a fragment, variant, or derivative of ELA-21 that is at least 95% identical to ELA-21.

4. A method for treating a subject suffering from a cardiac condition or having a risk factor for developing a cardiac condition comprising:
   (i) identifying a subject a subject suffering from a cardiac condition or having a risk factor for developing a cardiac condition; (ii) measuring an amount of a peptide of SEQ ID NO: 1, or a peptide of SEQ ID NO: 2, or a peptide of SEQ ID NO: 3, in the bloodstream of the subject suffering from a cardiac condition or having a risk factor for developing a cardiac condition; (iii) measuring an amount of a peptide of SEQ ID NO: 1, or a peptide of SEQ ID NO: 2, or a peptide of SEQ ID NO: 3, in the bloodstream of a normal control subject; (iv) comparing the amounts of the peptide of SEQ ID NO: 1, or SEQ ID NO: 2, or SEQ ID NO: 3, in the subject suffering from a cardiac condition or having a risk factor for developing a cardiac condition and that in the normal control subject; and (v) treating the subject with an effective amount of a peptide in a pharmaceutically acceptable form,
wherein the peptide is selected from the group consisting of: SEQ ID NO:5; and an Fc fusion with a fragment, variant, or derivative of ELA-21 that is at least 95% identical to ELA-21.

5. The method of claim 1, wherein the cardiac condition or risk factor for the cardiac condition is selected from the group consisting of: acute decompensated heart failure (ADHF), angina, arrhythmia, atherosclerosis, atrial fibrillation, Brugada syndrome, cardiac insufficiency, cardiomyocyte apoptosis, cardiovascular disease, carditis, constricted blood vessels, cardiomyopathy, chronic heart failure, congestive heart failure, damaged blood vessels, diabetes, elevated left ventricular end-diastolic pressure, electrolyte disorder, endocarditis, fibrosis, fluid retention, heart failure, high blood sugar, hyperlipidemia, hypertension, hypoxia-induced cardiomyocyte apoptosis, ischemia, hypertrophic cardiomyopathy, kidney disease, idiopathic cardiomyopathy, leaky blood vessels, lack of vascular endothelial cells, low ejection fraction, metabolic syndrome, myocardial infarction, myocardial infarction-induced cardiomyocyte apoptosis, myocardial-induced heart failure, myocardial-induced fibrosis, palpitations, peripheral arterial disease, obesity, pulmonary hypertension, reduced cardiac function, Raynaud's disease, rheumatic heart disease restenosis, stroke, ventricular tachycardia, and heart transplant.

6. The method of claim 2, wherein the cardiac condition or risk factor for the cardiac condition is selected from the group consisting of: acute decompensated heart failure (ADHF), angina, arrhythmia, atherosclerosis, atrial fibrillation, Brugada syndrome, cardiac insufficiency, cardiomyocyte apoptosis, cardiovascular disease, carditis, constricted blood vessels, cardiomyopathy, chronic heart failure, congestive heart failure, damaged blood vessels, diabetes, elevated left ventricular end-diastolic pressure, electrolyte disorder, endocarditis, fibrosis, fluid retention, heart failure, high blood sugar, hyperlipidemia, hypertension, hypoxia-induced cardiomyocyte apoptosis, ischemia, hypertrophic cardiomyopathy, kidney disease, idiopathic cardiomyopathy, leaky blood vessels, lack of vascular endothelial cells, low ejection fraction, metabolic syndrome, myocardial infarction, myocardial infarction-induced cardiomyocyte apoptosis, myocardial-induced heart failure, myocardial-induced fibrosis, palpitations, peripheral arterial disease, obesity, pulmonary hypertension, reduced cardiac function, Raynaud's disease, rheumatic heart disease restenosis, stroke, ventricular tachycardia, and heart transplant.

7. The method of claim 1, comprising further administering a therapeutic agent selected from the group consisting of: an angiotensin converting enzyme (ACE) inhibitor, an aldosterone antagonist, an angiotensin receptor blocker, a beta-blocker, a calcium channel blocker, a cholesterol lowering drug, a digoxin, a diuretic, a glucose lowering drug, potassium or magnesium, a vasopressin antagonist, and warfarin.

8. The method of claim 2, comprising further administering a therapeutic agent selected from the group consisting of: an angiotensin converting enzyme (ACE) inhibitor, an aldosterone antagonist, an angiotensin receptor blocker, a beta-blocker, a calcium channel blocker, a cholesterol lowering drug, a digoxin, a diuretic, a glucose lowering drug, potassium or magnesium, a vasopressin antagonist, and warfarin.

9. The method of claim 1, wherein the subject is a human.

10. The method of claim 2, wherein the subject is a human.

\* \* \* \* \*